US012593959B2

(12) United States Patent
Kato et al.

(10) Patent No.: US 12,593,959 B2
(45) Date of Patent: Apr. 7, 2026

(54) ENDOSCOPE TREATMENT TOOL

(71) Applicant: OLYMPUS MEDICAL SYSTEMS CORP., Tokyo (JP)

(72) Inventors: Hiromasa Kato, Tokyo (JP); Yusuke Shiota, Machida (JP); Kotaro Yamada, Tachikawa (JP)

(73) Assignee: Olympus Medical Systems Corp., Tokyo (JP)

( * ) Notice: Subject to any disclaimer, the term of this patent is extended or adjusted under 35 U.S.C. 154(b) by 586 days.

(21) Appl. No.: 17/974,178

(22) Filed: Oct. 26, 2022

(65) Prior Publication Data

US 2023/0133233 A1     May 4, 2023

Related U.S. Application Data

(60) Provisional application No. 63/273,179, filed on Oct. 29, 2021, provisional application No. 63/273,174, filed on Oct. 29, 2021.

(51) Int. Cl.
    *A61B 1/00*        (2006.01)
    *A61B 17/00*       (2006.01)

(52) U.S. Cl.
    CPC .............................. *A61B 1/00064* (2013.01); *A61B 2017/00296* (2013.01); *A61B 2218/002* (2013.01)

(58) Field of Classification Search
    CPC ................ A61B 18/14; A61B 18/1492; A61B 2018/00601; A61B 2018/00946;
           (Continued)

(56) References Cited

U.S. PATENT DOCUMENTS

| | | | |
|---|---|---|---|
| 2004/0172018 A1* | 9/2004 | Okada ................ | A61B 18/1402 |
| | | | 606/46 |
| 2016/0008063 A1* | 1/2016 | Wake ................. | A61B 17/3203 |
| | | | 606/49 |

(Continued)

FOREIGN PATENT DOCUMENTS

| | | |
|---|---|---|
| CN | 108272503 A | 7/2018 |
| JP | H08-155038 A | 6/1996 |

(Continued)

OTHER PUBLICATIONS

Office Action dated May 1, 2025, issued in corresponding Chinese Patent Application No. 202211327696.X.

(Continued)

*Primary Examiner* — Sarah A Long
(74) *Attorney, Agent, or Firm* — Morgan, Lewis & Bockius LLP

(57)         ABSTRACT

An endoscope treatment tool includes a sheath and an incision device. The sheath includes a distal end portion having a first channel. The first channel extends internal to the distal end portion between a distal opening at a distal end surface of the distal end portion and a proximal opening at a main flow chamber. The incision device is inserted in the first channel and includes a second channel extending between a distal end of the incision device and a proximal end of the incision device. The endoscope treatment tool is switchable between a first mode and a second mode. In the first mode, a first path for fluid is formed between the main flow chamber and the first channel. In the second mode, a second path for fluid is formed between the main flow chamber and the second channel.

13 Claims, 26 Drawing Sheets

(58) Field of Classification Search
    CPC ..... A61B 2017/00296; A61B 1/00064; A61M
                                    5/1407; A61M 5/19
    See application file for complete search history.

(56)                    References Cited

U.S. PATENT DOCUMENTS

2021/0113260 A1* 4/2021 Tang .................. A61M 5/1407
2022/0338926 A1 10/2022 Nakamura et al.

FOREIGN PATENT DOCUMENTS

| | | |
|---|---|---|
| JP | 2009-233093 A | 10/2009 |
| JP | 2021-512731 A | 5/2021 |
| WO | 2021/140609 A1 | 7/2021 |

OTHER PUBLICATIONS

Office Action dated Feb. 17, 2026, issued in corresponding Japanese
Patent Application No. 2022-128010.

\* cited by examiner

ENDOSCOPE TREATMENT TOOL

RELATED APPLICATION DATA

This application is based on and claims priority under 35 U.S.C. § 119 to U.S. Provisional Application Nos. 63/273,174 and 63/273,179, each of which was filed on Oct. 29, 2021. The entire contents of each of these applications are incorporated herein by reference.

FIELD OF THE DISCLOSURE

The present disclosure relates to an endoscope treatment tool.

BACKGROUND

An endoscope treatment tool has been known conventionally, the treatment tool including an insertion portion inserted into a body cavity via an endoscope and being for incision of a site (hereinafter, referred to as a target site) to be treated in body tissue by means of high frequency electric current (see, for example, Specification of Chinese Patent Application Publication No. 108272503).

The insertion portion of the endoscope treatment tool described in Specification of Chinese Patent Application Publication No. 108272503 includes: a sheath having a first hole at a distal end of the sheath, the first hole connecting the interior and the exterior to each other; and an incision portion that protrudes outside the sheath from the first hole and makes an incision in the target site by passage of the high frequency electric current. This incision portion has a second hole provided therein, the second hole penetrating the incision portion from near a proximal end of the incision portion to a distal end of the incision portion. This endoscope treatment tool is configured to be switched between: a first mode where liquid is passed to flow into the body cavity from a clearance between an inner surface of the first hole and an outer surface of the incision portion; and a second mode where the liquid is passed to flow into the body cavity from a second hole.

SUMMARY

In some embodiments, an endoscope treatment tool includes a sheath and an incision device. The sheath includes a distal end portion having a first channel. The first channel extends internal to the distal end portion between a distal opening at a distal end surface of the distal end portion and a proximal opening at a main flow chamber. The incision device is inserted in the first channel and includes a second channel extending between a distal end of the incision device and a proximal end of the incision device. The endoscope treatment tool is switchable between a first mode and a second mode. The endoscope treatment tool is in the first mode when the incision device is in a first position and the endoscope treatment tool is in the second mode when the incision device is in a second position. In the first mode, a first path for fluid is formed between the main flow chamber and the first channel. In the second mode, a second path for fluid is formed between the main flow chamber and the second channel.

DETAILED DESCRIPTION

Modes for implementing the disclosure (hereinafter, embodiments) will be described hereinafter while reference is made to the drawings. The disclosure is not limited by the embodiments described hereinafter. Furthermore, any portions that are the same will be assigned with the same reference sign, throughout the drawings.

First Embodiment

Figure 1:
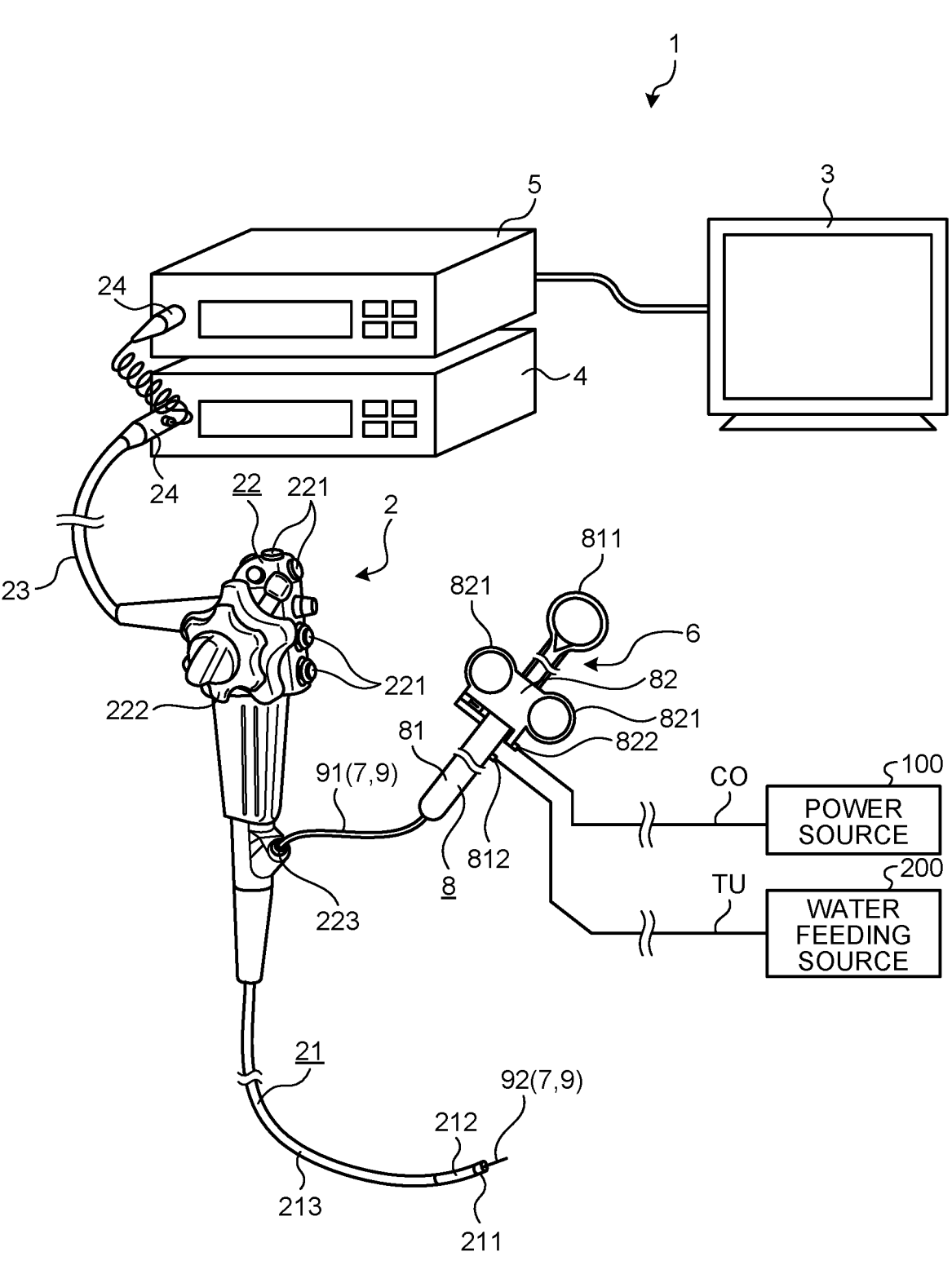
FIG. 1 is a diagram illustrating an endoscope system according to a first embodiment.

Configuration of Endoscope System
FIG. 1 is a diagram illustrating an endoscope system 1 according to a first embodiment.

The endoscope system 1 is a system that is used in the medical field and that is for observation of the interior of a body cavity and for application of high frequency energy to a site to be treated (hereinafter, referred to as a target site) in body tissue in the body cavity and treatment of the target site thereby. The treatment that is able to be executed by means of the endoscope system 1 according to the first embodiment is treatment, such as coagulation (sealing) of the target site, or incision of the target site. As illustrated in FIG. 1, this endoscope system 1 includes an endoscope 2, a display device 3, a light source device 4, a control device 5, and an endoscope treatment tool 6.

Part of the endoscope 2 is inserted into a body cavity, and the endoscope 2 captures a subject image reflected from the interior of the body cavity and outputs an image signal generated by the capturing. As illustrated in FIG. 1, this endoscope 2 includes an endoscope insertion unit 21, an endoscope operating unit 22, a universal cord 23, and a connector unit 24.

At least part of the endoscope insertion unit 21 has flexibility and the endoscope insertion unit 21 is a portion to be inserted into the body cavity. This endoscope insertion unit 21 includes, as illustrated in FIG. 1, a distal end unit 211, a bending portion 212, and a flexible tube 213.

The distal end unit 211 is provided at a distal end of the endoscope insertion unit 21. This distal end unit 211 has, provided therein, an illumination optical system, an imaging optical system, and an imaging unit, although specific illustration thereof has been omitted.

The illumination optical system faces one end of a light guide (not illustrated in the drawings) laid in the endoscope insertion unit 21, and light that has been transmitted through the light guide is emitted from the distal end of the endoscope insertion unit 21 into a body cavity.

The imaging optical system receives light (a subject image) that has been emitted into the body cavity from the illumination optical system and reflected from the interior of the body cavity, and forms the subject image on an imaging surface of an imaging element included in the imaging unit.

The imaging unit includes the imaging element, such as a charge coupled device (CCD) or a complementary metal oxide semiconductor (CMOS), captures the subject image formed by the imaging optical system, and outputs an image signal generated by the capturing.

The bending portion 212 is connected to the distal end unit 211 near a proximal end of the distal end unit 211 (near the endoscope operating unit 22). This bending portion 212 has a configuration with plural bending pieces connected to each other and is bendable, although specific illustration thereof has been omitted.

The flexible tube 213 is connected to the bending portion 212 near a proximal end (near the endoscope operating unit 22) of the bending portion 212, is elongated, and has flexibility.

The endoscope operating unit 22 is connected to a proximal end portion of the endoscope insertion unit 21. The endoscope operating unit 22 receives various operations for the endoscope 2. This endoscope operating unit 22 has, as illustrated in FIG. 1, provided therein, plural operating members 221, a bending knob 222, and an insertion opening 223.

The plural operating members 221 include, for example, buttons that receive various operations.

The bending knob 222 is configured to be rotatable according to a user operation. By rotating, the bending knob 222 causes a bending mechanism (not illustrated in the drawings) to operate, the bending mechanism being, for example, a wire provided in the endoscope insertion unit 21 and made of metal or resin. The bending portion 212 is thereby bent.

The insertion opening 223 is an insertion opening that communicates with a duct (not illustrated in the drawings)

extending from the distal end to near a proximal end (near the endoscope operating unit 22) of the endoscope insertion unit 21, the insertion opening being for insertion of, for example, a treatment tool insertion portion 7 of the endoscope treatment tool 6, into the duct, from the outside.

The universal cord 23 is a cord that extends from the endoscope operating unit 22, in a direction different from an extending direction of the endoscope insertion unit 21 and has, provided therein, for example, the light guide described above and a signal line for transmission of the image signal described above.

The connector unit 24 is provided at an end portion of the universal cord 23 and is detachably connected to the light source device 4 and the control device 5.

The display device 3 is, for example, a liquid crystal display (LCD) or an electroluminescence (EL) display, and displays a predetermined image, under control by the control device 5.

The light source device 4 emits illumination light. The illumination light emitted from the light source device 4 is emitted into a body cavity from the distal end of the endoscope insertion unit 21 after passing through the connector unit 24, the universal cord 23, the endoscope operating unit 22, the light guide laid in the endoscope insertion unit 21, and the illumination optical system.

The control device 5 includes, for example, a central processing unit (CPU) or a field-programmable gate array (FPGA), and integrally controls operation of the display device 3 and the light source device 4.

For example, the control device 5 performs predetermined processing of an image signal input through the signal line mentioned above from the imaging unit described above and generates an endoscopic image. The control device 5 then controls operation of the display device 3 and causes the display device 3 to display the endoscopic image, for example.

In this first embodiment, the light source device 4 and the control device 5 are configured to be separately bodied, but may be integrally provided in a single casing.

Configuration of Endoscope Treatment Tool

The endoscope treatment tool 6 is a treatment tool used in, for example, endoscopic submucosal dissection (ESD). This treatment tool 6 for an endoscope includes, as illustrated in FIG. 1, the treatment tool insertion portion 7 and a treatment tool operating unit 8.

As illustrated in FIG. 1, the treatment tool insertion portion 7 is a portion that protrudes from the distal end of the endoscope insertion unit 21 by passing through the duct in the endoscope insertion unit 21 from the insertion opening 223 and that is to be inserted into a body cavity, and the treatment tool insertion portion 7 corresponds to an insertion portion.

A detailed configuration of the treatment tool insertion portion 7 will be described in a later section, "Configuration of Treatment Tool Insertion Portion". Furthermore, a "distal end" referred to hereinafter means one end of the treatment tool insertion portion 7, the one end being in an insertion direction in which the treatment tool insertion portion 7 is inserted, and a "proximal end" referred to hereinafter means the other end of the treatment tool insertion portion 7, the other end being in a direction opposite to the insertion direction.

The treatment tool operating unit 8 is connected to a proximal end portion of the treatment tool insertion portion 7 (a portion near the proximal end of the treatment tool insertion portion 7 with respect to the insertion direction). The treatment tool operating unit 8 receives an operation on the endoscope treatment tool 6. This treatment tool operating unit 8 includes, as illustrated in FIG. 1, an operating unit main body 81 and a slider 82.

The operating unit main body 81 has an elongated shape, and a proximal end portion of a sheath 9 included in the treatment tool insertion portion 7 and described later is fixed to the operating unit main body 81. Furthermore, a ring 811 is provided at a proximal end portion of the operating unit main body 81, the ring 811 being for an operator, such as an operating surgeon, to place the operator's finger, as illustrated in FIG. 1. In addition, a water feeding port 812 is provided in the operating unit main body 81, the water feeding port 812 being where a tube TU is connected to. Saline solution is supplied from a water feeding source 200, such as a pump, to the water feeding port 812 via the tube TU.

This saline solution corresponds to fluid. The fluid is not necessarily saline solution, and any other liquid, or gas, such as air, may be adopted as the fluid.

The slider 82 is attached to the operating unit main body 81 so that the slider 82 is movable along a longitudinal direction of the operating unit main body 81 according to an operation performed by an operator, such as an operating surgeon. As illustrated in FIG. 1, this slider 82 has a pair of rings 821 for the operator, such as the operating surgeon, to place the operator's finger/fingers on. Furthermore, a plug 822 where a power source cord CO is connected to is provided in the slider 82. The plug 822 is electrically connected to a power source 100 via the power source cord CO.

Configuration of Treatment Tool Insertion Portion

Figure 2:
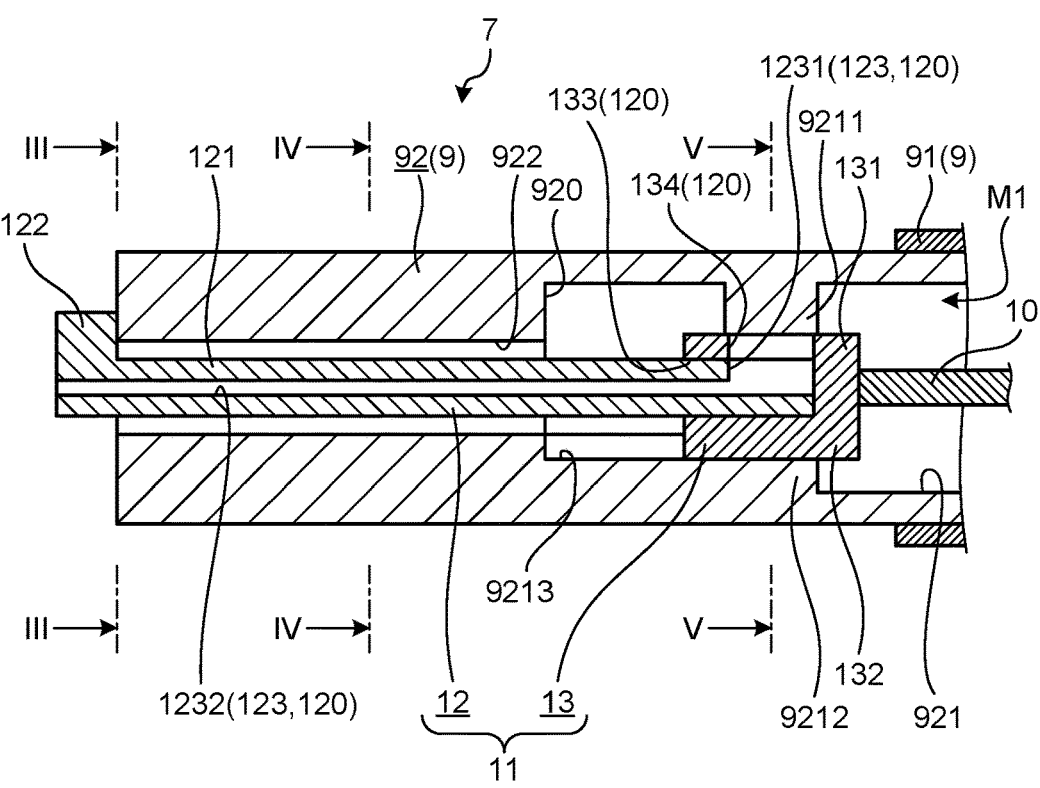
FIG. 2 is a diagram illustrating a configuration of a treatment tool insertion portion.
Figure 3:
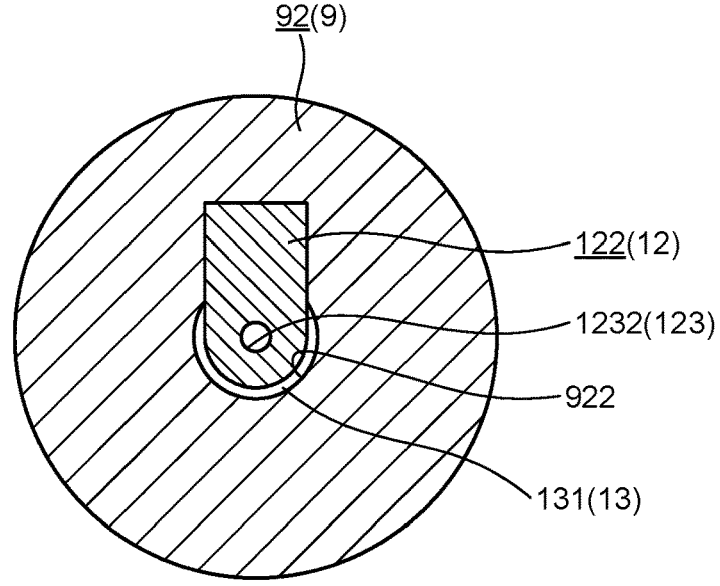
FIG. 3 is a diagram illustrating the configuration of the treatment tool insertion portion.
Figure 4:
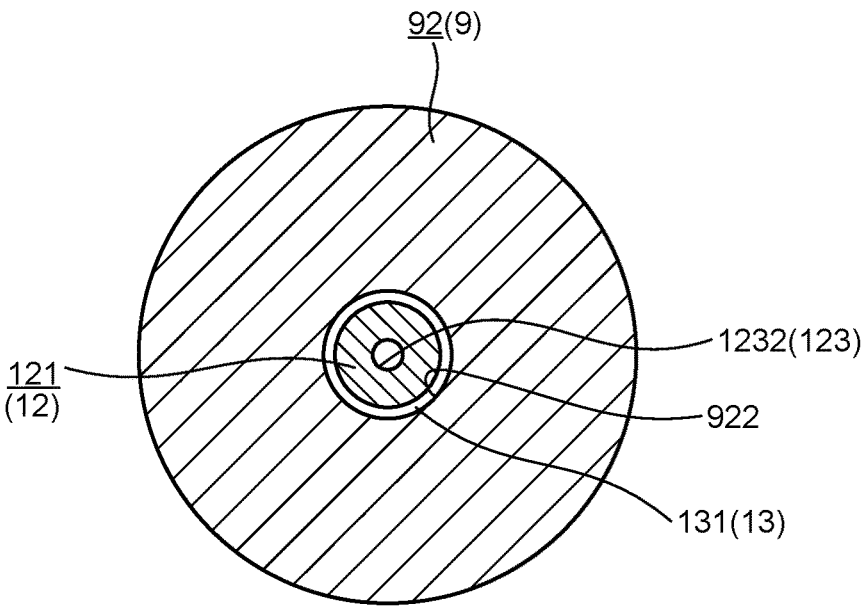
FIG. 4 is a diagram illustrating the configuration of the treatment tool insertion portion.
Figure 5:
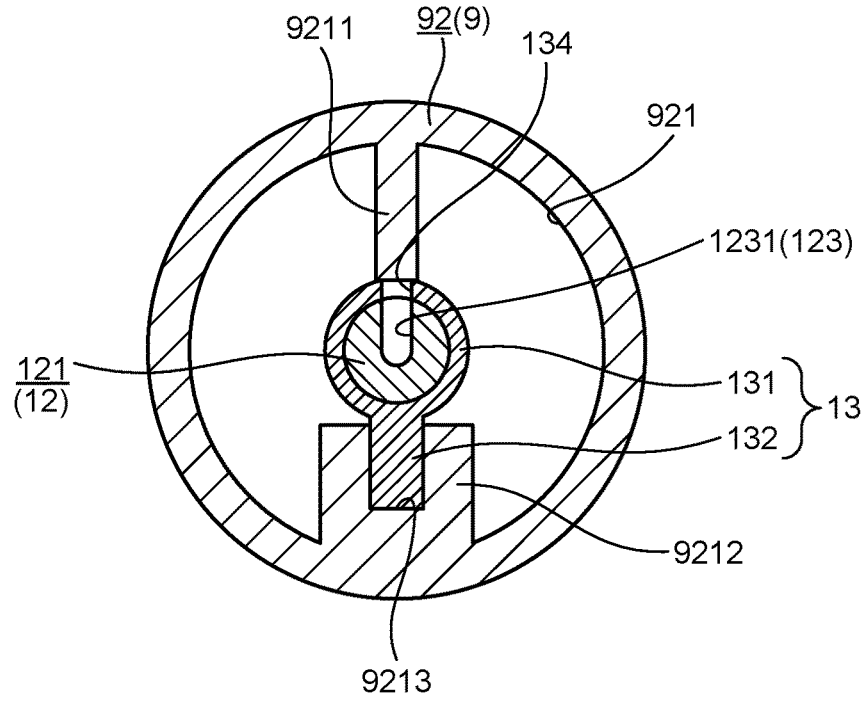
FIG. 5 is a diagram illustrating the configuration of the treatment tool insertion portion.

FIG. 2 to FIG. 5 are diagrams each illustrating a configuration of the treatment tool insertion portion 7. Specifically, FIG. 2 is a sectional view of a distal end portion of the treatment tool insertion portion 7, the sectional view being taken upon a plane including a central axis of the treatment tool insertion portion 7. FIG. 3 is a sectional view of the treatment tool insertion portion 7, the sectional view being taken at a position of a line III-III illustrated in FIG. 2. FIG. 4 is a sectional view of the treatment tool insertion portion 7, the sectional view being taken at a position of a line IV-IV illustrated in FIG. 2. FIG. 5 is a sectional view of the treatment tool insertion portion 7, the sectional view being taken at a position of a line V-V illustrated in FIG. 2.

As illustrated in FIG. 1 to FIG. 5, the treatment tool insertion portion 7 includes the sheath 9, a wire 10 (FIG. 2), and an incision portion 11 (FIG. 2). The incision portion 11 may correspond to an incision device.

The sheath 9 is a portion forming an outer surface of the treatment tool insertion portion 7. This sheath 9 includes, as illustrated in FIG. 1 and FIG. 2, a sheath main body 91 and a distal end member 92.

The sheath main body 91 is a cylindrical member formed of, for example, a resin material and having insulation and flexibility. A proximal end portion of the sheath main body 91 is fixed to the operating unit main body 81. The interior of the sheath main body 91 communicates with the water feeding port 812.

The distal end member 92 has a cylindrical shape with a bottom, and closes a distal end portion of the sheath main body 91, in a posture where a bottom portion 920 thereof is oriented in a distal direction (leftward in FIG. 2). This distal end member 92 may be formed of a member made of ceramic, a resin material, or rubber, for example, and having electric insulation, or may be formed of a member having an insulation coating, for example, such as metal, on a surface thereof. The distal end member 92 may be formed of a single part or may be formed of a combination of plural parts.

First and second wall portions 9211 and 9212 are provided on an inner peripheral surface 921 of the distal end member 92, as illustrated in FIG. 2 and FIG. 5.

The first wall portion 9211 is a wall protruding toward a central axis of the distal end member 92 from the inner peripheral surface 921 and extending along the central axis, as illustrated in FIG. 2 and FIG. 5.

The second wall portion 9212 is a wall protruding toward the central axis of the distal end member 92 from the inner peripheral surface 921 and extending along the central axis to the bottom portion 920 of the distal end member 92, as illustrated in FIG. 2 and FIG. 5. Furthermore, as illustrated in FIG. 2 and FIG. 5, a groove portion 9213 extending over the entire length of the second wall portion 9212 is provided in the second wall portion 9212.

The interior of the sheath main body 91 and the interior of the distal end member 92 described above function as a main flow channel M1 (FIG. 2), the main flow channel M1 being where saline solution supplied from the water feeding source 200 flows through via the tube TU and the water feeding port 812. The main flow channel M1 may correspond to a main flow chamber.

Furthermore, a first hole 922 that provides communication between the bottom portion 920 and a distal end of the distal end member 92 is provided in the bottom portion 920 of the distal end member 92, as illustrated in FIG. 2 to FIG. 4, and this first hole 922 is open in the bottom portion 920 and at the distal end of the distal end member 92. This bottom portion 920 corresponds to a distal end portion of a sheath. The first hole 922 may correspond to a first channel.

The first hole 922 has a circular cross-section and extends linearly along the central axis of the distal end member 92. The dimension of the inner diameter of the first hole 922 is set smaller than the dimension of the inner diameter of the inner peripheral surface 921, as illustrated in FIG. 2. The first hole 922 may preferably be positioned on the central axis of the distal end member 92.

The wire 10 is formed of an electrically conducting material, such as metal, and is inserted in the sheath 9. A proximal end portion of the wire 10 is fixed to the slider 82. That is, according to an operation on the slider 82 by an operator, such as an operating surgeon, the wire 10 advances or retracts in the sheath 9. Furthermore, the wire 10 is electrically connected to the plug 822.

The incision portion 11 is formed of an electrically conducting material, such as metal, and is fixed to a distal end portion of the wire 10. Furthermore, the incision portion 11 is inserted in the first hole 922. That is, together with the wire 10, the incision portion 11 advances or retracts in the sheath 9 (the first hole 922) according to an operation on the slider 82 by an operator, such as an operating surgeon. The incision portion 11 is translatable in the first hole 922 between a proximal position and a distal position. Furthermore, a distal end portion of the incision portion 11 protrudes outside the distal end member 92 from the first hole 922. High frequency electric current is passed to the incision portion 11 via the power source cord CO, the plug 822, and the wire 10, and an incision is thereby made in a target site in a body cavity. This incision portion 11 includes a knife 12, as illustrated in FIG. 2 to FIG. 5.

The knife 12 is a portion that protrudes outside from the distal end member 92 from the first hole 922 and as illustrated in FIG. 2, is formed of a so-called hook knife. This knife 12 includes a knife main body 121 and a projecting portion 122.

The knife main body 121 is positioned on the central axis of the distal end member 92 and is formed of a cylindrical member extending linearly along the central axis. The dimension of the outer diameter of the knife main body 121 is set smaller than the dimension of the inner diameter of the first hole 922, as illustrated in FIG. 2 and FIG. 4.

The projecting portion 122 is a portion provided at a distal end of the knife main body 121 and bent by approximately 90° relatively to the knife main body 121, upward in FIG. 2.

The knife 12 described above has a knife hole 123 provided therein, as illustrated in FIG. 2, the knife hole 123 penetrating the knife 12 from near a proximal end to a distal end of the knife 12. This knife hole 123 includes an inflow hole 1231 and an outflow hole 1232.

The inflow hole 1231 is a hole extending toward a central axis of the knife main body 121 from above in FIG. 2 and FIG. 5 at a proximal end portion of the knife main body 121.

The outflow hole 1232 is a hole positioned on the central axis of the knife main body 121 and extending linearly along the central axis. The outflow hole 1232 communicates with the exterior of the knife 12 through the projecting portion 122 near a distal end of the outflow hole 1232 and communicates with the outflow hole 1232 near a proximal end of the outflow hole 1232.

A connector 13 is provided near the proximal end of the knife 12, as illustrated in FIG. 2 to FIG. 5.

The connector 13 is a member that connects the knife 12 and the wire 10 to each other. This connector 13 includes a cylindrical portion 131 and a rotation restricting portion 132.

The cylindrical portion 131 is formed of a cylindrical member extending linearly along the central axis of the distal end member 92. The dimension of the outer diameter of the cylindrical portion 131 is set slightly smaller than the dimension of the distance between the first wall portion 9211 and the second wall portion 9212 and larger than the dimension of the inner diameter of the first hole 922, as illustrated in FIG. 5. The cylindrical portion 131 may preferably be positioned on the central axis of the distal end member 92.

The cylindrical portion 131 has a fitting hole 133 provided therein, the fitting hole 133 extending from a distal end face toward a proximal end (rightward in FIG. 2) of the cylindrical portion 131 and being where the knife main body 121 is fitted into, as illustrated in FIG. 2. Furthermore, the cylindrical portion 131 has a communicating hole 134 provided therein, the communicating hole 134 extending toward a central axis of the cylindrical portion 131 from an outer peripheral surface of the cylindrical portion 131 and communicating with the inflow hole 1231, as illustrated in FIG. 2 and FIG. 5.

The knife hole 123, fitting hole 133, and communicating hole 134 described above are open on an outer peripheral surface of the incision portion 11 near a proximal end of the incision portion 11 and correspond to a second hole 120 (FIG. 2). The second hole 120 may correspond to a second channel.

The rotation restricting portion 132 is a projection protruding from the outer peripheral surface of the cylindrical portion 131 and is inserted in the groove portion 9213, as illustrated in FIG. 2 and FIG. 5. The rotation restricting portion 132 stays continually inserted in the groove portion 9213 when the incision portion 11 is advancing and retracting in the sheath 9 according to operations on the slider 82 by an operator, such as an operating surgeon. The rotation restricting portion 132 restricts rotation of the knife 12 and the wire 10 about the central axis.

The second wall portion 9212 (the groove portion 9213) and the rotation restricting portion 132 described above correspond to a rotation restricting structure.

Operation of Endoscope Treatment Tool Operation of the above described treatment tool 6 for an endoscope will be described next. A flow of ESD will be described hereinafter as an example for convenience of explanation.

Figure 6:
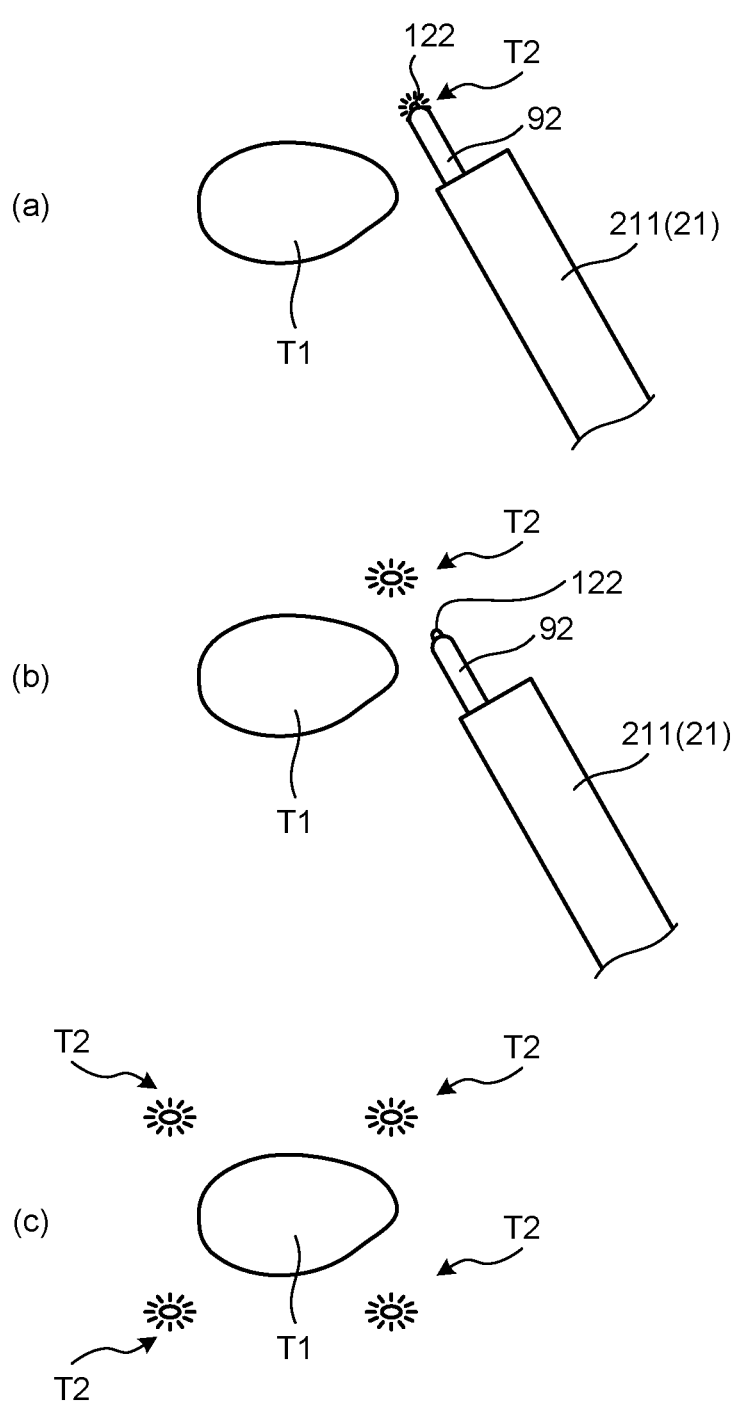
FIG. 6 is a diagram illustrating operation of an endoscope treatment tool.
Figure 7:
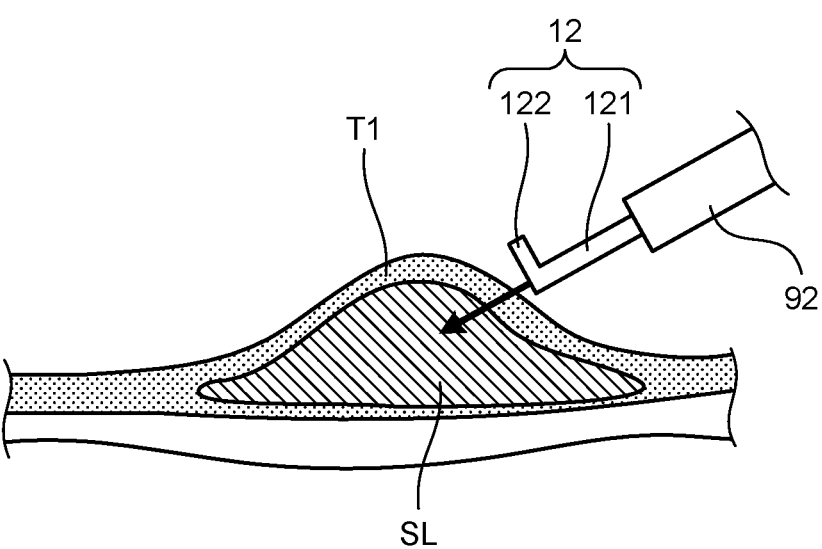
FIG. 7 is a diagram illustrating operation of the endoscope treatment tool.
Figure 8:
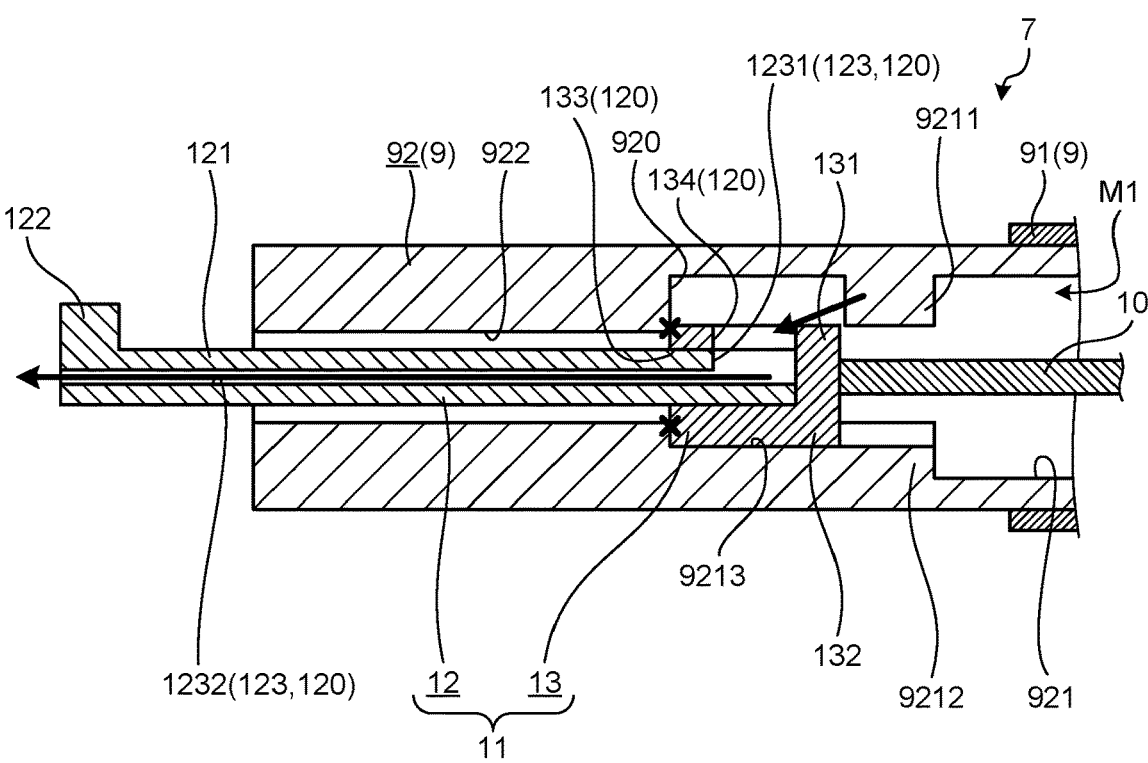
FIG. 8 is a diagram illustrating operation of the endoscope treatment tool.
Figure 9:
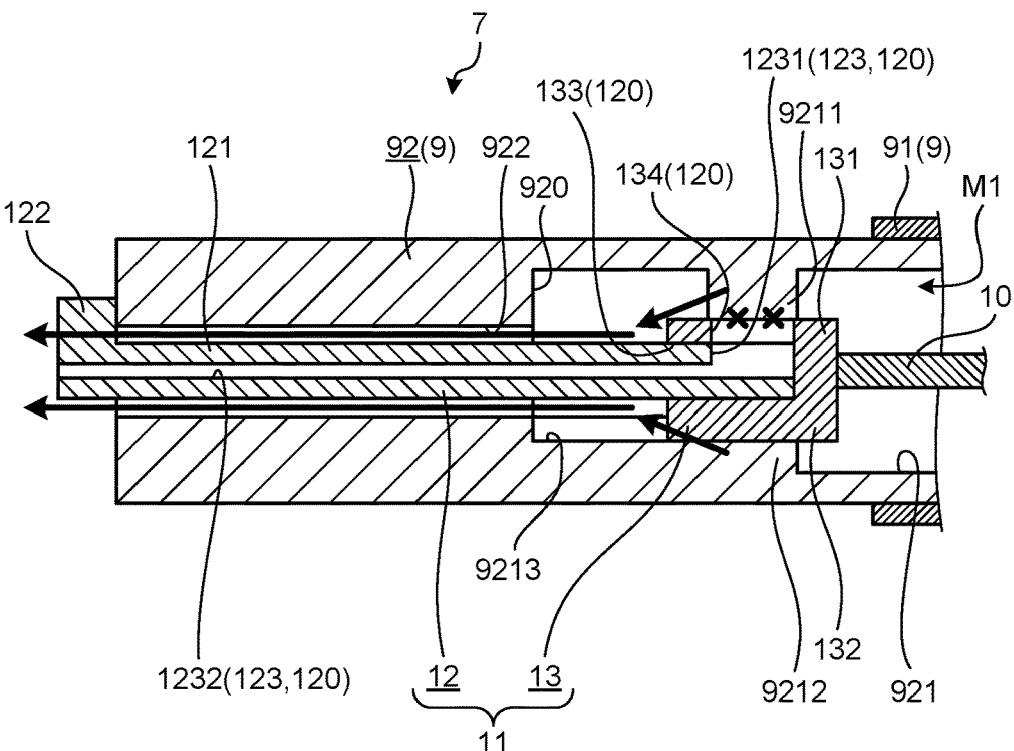
FIG. 9 is a diagram illustrating operation of the endoscope treatment tool.

FIG. 6 to FIG. 9 are diagrams illustrating the operation of the endoscope treatment tool 6. Specifically, FIG. 6 is a diagram illustrating a marking process in ESD. FIG. 7 is a diagram illustrating a local injection process in ESD. FIG. 8 and FIG. 9 are sectional views corresponding to FIG. 2.

Firstly, an operator, such as an operating surgeon, inserts the endoscope insertion unit 21 into a body cavity and moves the distal end of the endoscope insertion unit 21 to near a target site T1 (FIG. 6).

Subsequently, the operator, such as an operator surgeon, performs a first operation of retracting the slider 82 toward the operator (toward the ring 811). The projecting portion 122 is thereby brought into a state where the projecting portion 122 is in contact with the distal end of the distal end member 92 and only the projecting portion 122 has protruded outside the distal end member 92 from the first hole 922. The operator, such as an operating surgeon, inserts the treatment tool insertion portion 7 into the duct in the endoscope insertion unit 21 from the insertion opening 223 and causes the treatment tool insertion portion 7 to protrude from the distal end of the endoscope insertion unit 21.

Subsequently, as described hereinafter, an operator, such as an operating surgeon, performs a marking process.

That is, the operator, such as an operating surgeon, operates an operating unit (not illustrated in the drawings), such as a foot switch, to pass high frequency electric current to the knife 12 from the power source 100 while maintaining the state where only the projecting portion 122 has protruded outside the distal end member 92 from the first hole 922 through the first operation on the slider 82. The operator, such as an operating surgeon, then presses the projecting portion 122 against body tissue around the target site T1 as illustrated at (a) in FIG. 6. The body tissue that has come into contact with the projecting portion 122 is thereby cauterized. That is, as illustrated at (a) in FIG. 6 and (b) in FIG. 6, a mark T2 is formed at the cauterized site.

The operator, such as an operating surgeon, repeats the above described operation a plural number of times, to form marks T2, as illustrated at (c) in FIG. 6, the number of marks T2 being a number that allows the outline of the target site T1 to be perceived. Thereafter, the operator, such as an operating surgeon, ends passing the high frequency electric current to the knife 12 from the power source 100.

Subsequently, an operator, such as an operating surgeon, performs a local injection process, as described hereinafter.

That is, the operator, such as an operating surgeon, performs a second operation of advancing the slider 82. The knife 12 thereby protrudes from a distal end of the sheath 9 (the distal end member 92) by the maximum protruding length, as illustrated in FIG. 8. In this state, the connector 13 is in contact with the bottom portion 920 (a peripheral edge portion of an opening) of the distal end member 92. The opening of the first hole 922 is thereby closed by the connector 13, as indicated by marks, "x", in FIG. 8, the opening being near a proximal end of the first hole 922. That is, the connector 13 corresponds to a second closing portion, the second closing portion enabling the opening of the first hole 922 to be closed, the opening being near the proximal end of the first hole 922. By contrast, the communicating hole 134 is positioned at a position displaced from a position opposite to the first wall portion 9211. That is, the position of the communicating hole 134 is displaced from the position of the first wall portion 9211 along a longitudinal axis direction of the sheath 9. The communicating hole 134 is thereby in communication with the main flow channel M1.

Furthermore, an operator, such as an operating surgeon, operates an operating unit (not illustrated in the drawings), such as a foot switch, to supply saline solution from the water feeding source 200, while maintaining the state where the knife 12 has protruded from the distal end of the sheath 9 by the maximum protruding length through the second operation on the slider 82. The saline solution supplied from the water feeding source 200 is discharged from the distal end of the knife 12 after following a flow channel through the communicating hole 134, the inflow hole 1231, and the outflow hole 1232, from the main flow channel M1, as indicated by arrows in FIG. 8. The discharged saline solution SL is injected below the target site T1 by the force of the current of the saline solution SL (FIG. 7). The target site T1 then floats up from other tissue, such as a submucosal layer below the target site T1.

Subsequently, an operator, such as an operating surgeon, performs an incision process, as described hereinafter.

That is, the operator, such as an operating surgeon, operates an operating unit (not illustrated in the drawings), such as a foot switch, to pass high frequency electric current to the knife 12 from the power source 100 while maintaining the state where the knife 12 has protruded from the distal end of the sheath 9 (the distal end member 92) by the maximum protruding length through the second operation on the slider 82. The operator, such as an operating surgeon, moves the projecting portion 122 along the periphery of the target site T1 in a state where the projecting portion 122 has been stuck into the body tissue to make an incision along the entire periphery of the target site T1, while seeing the marks T2. Thereafter, by exfoliation, for example, of the submucosal layer for a mucosal layer including the target site T1 incised along its entire periphery, the target site T1 is removed.

The ESD is completed by the above processes. When performing irrigation of the surgical site in the above described processes of the ESD, an operator, such as an operating surgeon, performs the following operation.

The operator, such as an operating surgeon, sets the state where only the projecting portion 122 has protruded outside the distal end member 92 from the first hole 922 through the first operation on the slider 82, that is, a state where the projecting portion 122 has protruded from the first hole 922 and the knife main body 121 has been positioned in the first hole 922. In this state, as illustrated in FIG. 5 and FIG. 9, the communicating hole 134 is positioned at a position opposite to the first wall portion 9211. That is, the position of the communicating hole 134 is aligned with the position of the first wall portion 9211, in a longitudinal axis direction of the sheath 9. In this state, the first wall portion 9211 is in contact with the outer peripheral surface (a peripheral edge portion of an opening) of the cylindrical portion 131 and the communicating hole 134 (the opening of the second hole 120, the opening being near a proximal end of the second hole 120) is thereby closed by the first wall portion 9211 as indicated by the marks, "x", in FIG. 9. That is, the first wall portion 9211 corresponds to a first closing portion, the first closing portion being arranged in the sheath 9 and enabling the opening of the incision portion 11 to be closed, the opening being near the proximal end of the incision portion 11. By contrast, the first hole 922 is released from the closure by the connector 13 and is in communication with the main flow channel M1.

Subsequently, an operator, such as an operating surgeon, operates an operating unit (not illustrated in the drawings), such as a foot switch, to cause saline solution to be supplied from the water feeding source 200. The saline solution supplied from the water feeding source 200 is thereby discharged from the distal end of the sheath 9 (the distal end member 92) and supplied to the surgical site in the body cavity, after following a flow channel through the first hole 922 from the main flow channel M1, as indicated by arrows in FIG. 9. An opening between an inner peripheral surface of the first hole 922 and an outer peripheral surface of the knife main body 121 has an area larger than that of an opening of the outflow hole 1232. Therefore, the surgical site is irrigated with the saline solution discharged from the distal end of the sheath 9 (the distal end member 92).

As described above, in this first embodiment, the main flow channel M1 is capable of communicating with each of the first hole 922 and the second hole 120, near the distal end of the sheath 9 (the distal end member 92). Furthermore, in this configuration, switching between a first mode and a second mode is enabled by advancement and retraction of the incision portion 11 according to operations on the slider 82 by an operator, such as an operating surgeon. The first mode is set by movement of the incision portion 11 toward the proximal end of the sheath 9 and is a mode where saline solution is passed to flow into a body cavity by the main flow channel M1 and the first hole 922 communicating with each other. More specifically, the first mode is a state where the main flow channel M1 and the first hole 922 are in communication with each other, and the opening of the incision portion 11 is closed by the first wall portion 9211, the opening being near the proximal end of the incision portion 11. The second mode is set by movement of the incision portion 11 toward the distal end of the sheath 9 and is a mode where saline solution is passed to flow into the body cavity by the main flow channel M1 and the second hole 120 communicating with each other. More specifically, the second mode is a state where the main flow channel M1 and the second hole 120 are in communication with each other and the opening of the first hole 922 is closed by the connector 13, the opening being near the proximal end of the first hole 922.

The above described first embodiment has the following effects.

The main flow channel M in the endoscope treatment tool 6, according to the first embodiment, is capable of communicating with each of the first and second holes 922 and 120 near the distal end of the sheath 9 (the distal end member 92). In other words, a flow channel where saline solution is to flow through in the treatment tool insertion portion 7 includes a single flow channel (the main flow channel M1) from near the proximal end of the treatment tool insertion portion 7 to near the distal end of the treatment tool insertion portion 7 and branches into two (the first and second holes 922 and 120) near the distal end of the sheath 9 (the distal end member 92).

Furthermore, an operator, such as an operating surgeon, is able to switch the endoscope treatment tool 6, according to the first embodiment, between the first and second modes by performing the first and second operations on the slider 82, the first and second operations being uncomplicated operations. Therefore, each of the local injection process and another process in ESD is able to be executed by means of the mere single treatment tool 6 for an endoscope without change of treatment tools between the local injection process and the other process.

Therefore, the endoscope treatment tool 6, according to the first embodiment, enables improvement in user-friendliness.

Furthermore, the rotating restricting structure (the second wall portion 9212 (the groove portion 9213) and the rotation restricting portion 132) that restricts rotation of the incision portion 11 about the central axis is provided between the incision portion 11 and the sheath 9 in the endoscope treatment tool 6, according to the first embodiment. Therefore, a so-called hook knife that needs to avoid rotating about the central axis is able to be adopted as the knife 12.

Second Embodiment

A second embodiment will be described next.

In the following description, any component that is the same as that of the above described first embodiment will be assigned with the same reference sign, and detailed description thereof will be omitted or simplified.

The distal end portion of the treatment tool insertion portion 7 of the endoscope treatment tool 6, described above with respect to the first embodiment, is differently configured in an endoscope treatment tool 6, according to the second embodiment. For convenience of explanation, a treatment tool insertion portion according to the second embodiment will hereinafter be referred to as a treatment tool insertion portion 7A.

Figure 10:
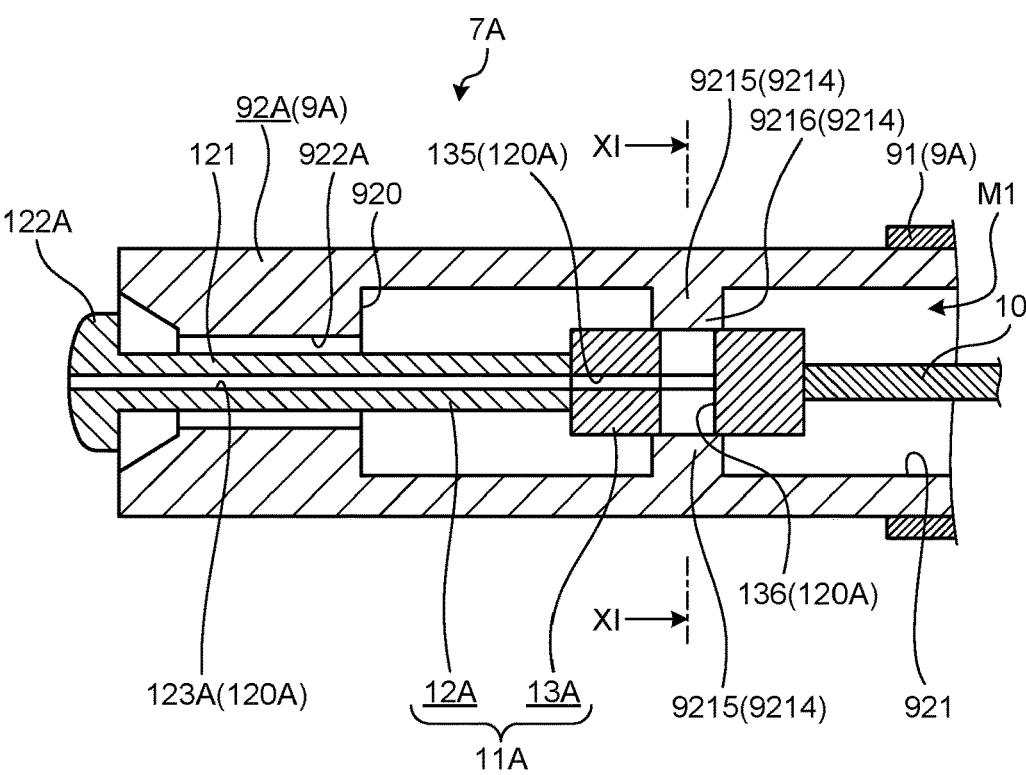
FIG. 10 is a diagram illustrating a configuration of a treatment tool insertion portion according to a second embodiment.
Figure 11:
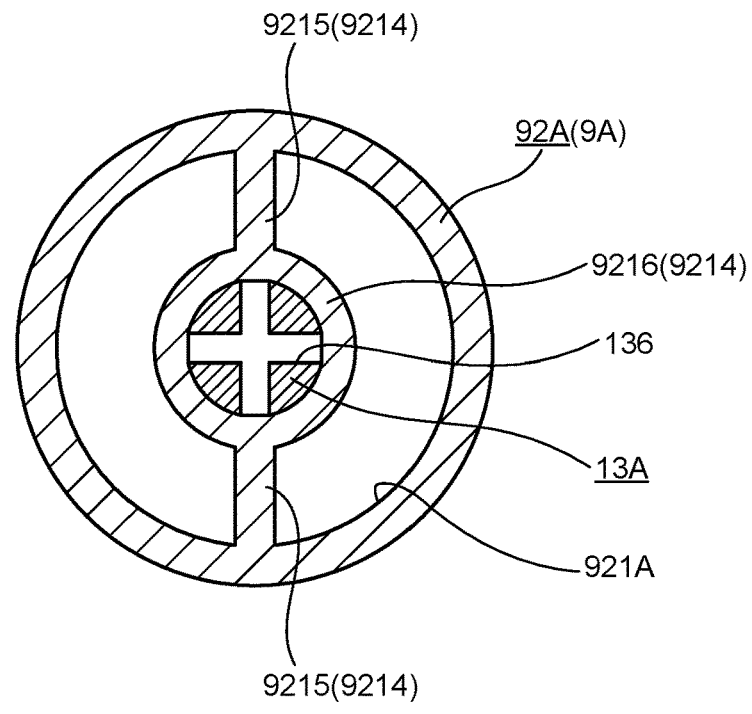
FIG. 11 is a diagram illustrating the configuration of the treatment tool insertion portion according to the second embodiment.

FIG. 10 and FIG. 11 are diagrams illustrating a configuration of the treatment tool insertion portion 7A according to the second embodiment. Specifically, FIG. 10 is a sectional view corresponding to FIG. 2. FIG. 11 is a sectional view of the treatment tool insertion portion 7A at a position of a line XI-XI illustrated in FIG. 10.

The sheath 9 and the incision portion 11 of the treatment tool insertion portion 7 described above with respect to the first embodiment are differently configured in the treatment tool insertion portion 7A, as illustrated in FIG. 10 and FIG. 11. For convenience of explanation, a sheath and an incision portion according to the second embodiment will hereinafter be referred to as a sheath 9A and an incision portion 11A, respectively.

As illustrated in FIG. 10 and FIG. 11, the distal end member 92 of the sheath 9 described above with respect to the first embodiment is differently shaped in the sheath 9A. For convenience of explanation, a distal end member according to the second embodiment will hereinafter be referred to as a distal end member 92A.

The distal end member 92A may be formed of a single part or may be formed of a combination of plural parts.

As illustrated in FIG. 10 and FIG. 11, a third wall portion 9214 is provided in the distal end member 92A, instead of the first and second wall portions 9211 and 9212 of the distal end member 92 described above with respect to the first embodiment.

As illustrated in FIG. 10 and FIG. 11, the third wall portion 9214 includes a pair of supporting portions 9215 and a ring portion 9216.

As illustrated in FIG. 10 and FIG. 11, each of the pair of supporting portions 9215 protrudes linearly toward a central axis of the distal end member 92A from an inner peripheral surface 921.

The ring portion 9216 has a ring shape having an axis that is the same as the central axis of the distal end member 92A and an outer peripheral surface of the ring portion 9216 is connected to tips of the pair of supporting portions 9215, as illustrated in FIG. 11.

Furthermore, as illustrated in FIG. 10, the first hole 922 in the distal end member 92 described above with respect to the first embodiment is differently shaped in the distal end member 92A. For convenience of explanation, a first hole according to the second embodiment will hereinafter be referred to as a first hole 922A.

The first hole 922A has a circular cross-section and extends linearly along the central axis of the distal end member 92A. Furthermore, as illustrated in FIG. 10, a distal end portion of the first hole 922A increases in diameter toward a distal end of the first hole 922A. The dimension of the inner diameter of a proximal end portion of the first hole 922A is set smaller than the dimension of the inner diameter of the inner peripheral surface 921. Furthermore, the dimension of the inner diameter of the first hole 922A is set larger than the dimension of the outer diameter of a knife main body 121. The first hole 922A may preferably be positioned on the central axis of the distal end member 92A.

As illustrated in FIG. 10 and FIG. 11, the knife 12 and the connector 13 of the incision portion 11 described above with respect to the first embodiment are differently shaped in the incision portion 11A, as illustrated in FIG. 10 and FIG. 11. For convenience of explanation, a knife and a connector according to the second embodiment will hereinafter be referred to as a knife 12A and a connector 13A, respectively.

As illustrated in FIG. 10, the projecting portion 122 of the knife 12 described above with respect to the first embodiment is differently shaped in the knife 12A. For convenience of explanation, a projecting portion according to the second embodiment will hereinafter be referred to as a projecting portion 122A.

The projecting portion 122A has a disk shape having an axis that is the same as a central axis of the knife main body 121. The dimension of the outer diameter of the projecting portion 122A is set smaller than the dimension of the inner diameter of the distal end portion of the first hole 922A, as illustrated in FIG. 10.

Furthermore, as illustrated in FIG. 10, the knife hole 123 in the knife 12 described above with respect to the first embodiment is differently shaped in the knife 12A. For convenience of explanation, a knife hole according to the second embodiment will hereinafter be referred to as a knife hole 123A.

As illustrated in FIG. 10, the knife hole 123A is positioned on the central axis of the knife main body 121 and linearly penetrates the knife main body 121 from a proximal end of the knife main body 121 to a distal end face of the projecting portion 122A, along the central axis.

The connector 13A is formed of a cylindrical member extending linearly along the central axis of the distal end member 92A. The dimension of the outer diameter of the connector 13A is set slightly smaller than the dimension of the inner diameter of the ring portion 9216 (FIG. 11) and larger than the dimension of the inner diameter of the proximal end portion of the first hole 922A. Furthermore, as illustrated in FIG. 10 and FIG. 11, first and second communicating holes 135 and 136 are provided in the connector 13A. The connector 13A may preferably be positioned on the central axis of the distal end member 92A.

The first communicating hole 135 extends linearly along the central axis from a distal end of the connector 13A toward a proximal end of the connector 13A, as illustrated in FIG. 10. In a state where the connector 13A and the knife main body 121 have been connected to each other, the first communicating hole 135 is in communication with the knife hole 123A. The first communicating hole 135 may preferably be positioned on a central axis of the connector 13A.

The second communicating hole 136 is a cross-shaped hole that communicates with the first communicating hole 135 and communicates with an opening on an outer peripheral surface of the connector 13A.

The above described knife hole 123A and first and second communicating holes 135 and 136 are open on the outer peripheral surface of the incision portion 11A, the outer peripheral surface being near a proximal end of the incision portion 11A, and correspond to a second hole 120A (FIG. 10).

Operation of the endoscope treatment tool 6, according to the second embodiment, will be described next. For convenience of explanation, a flow of ESD will hereinafter be described as an example, similarly to the above described first embodiment.

Figure 12:
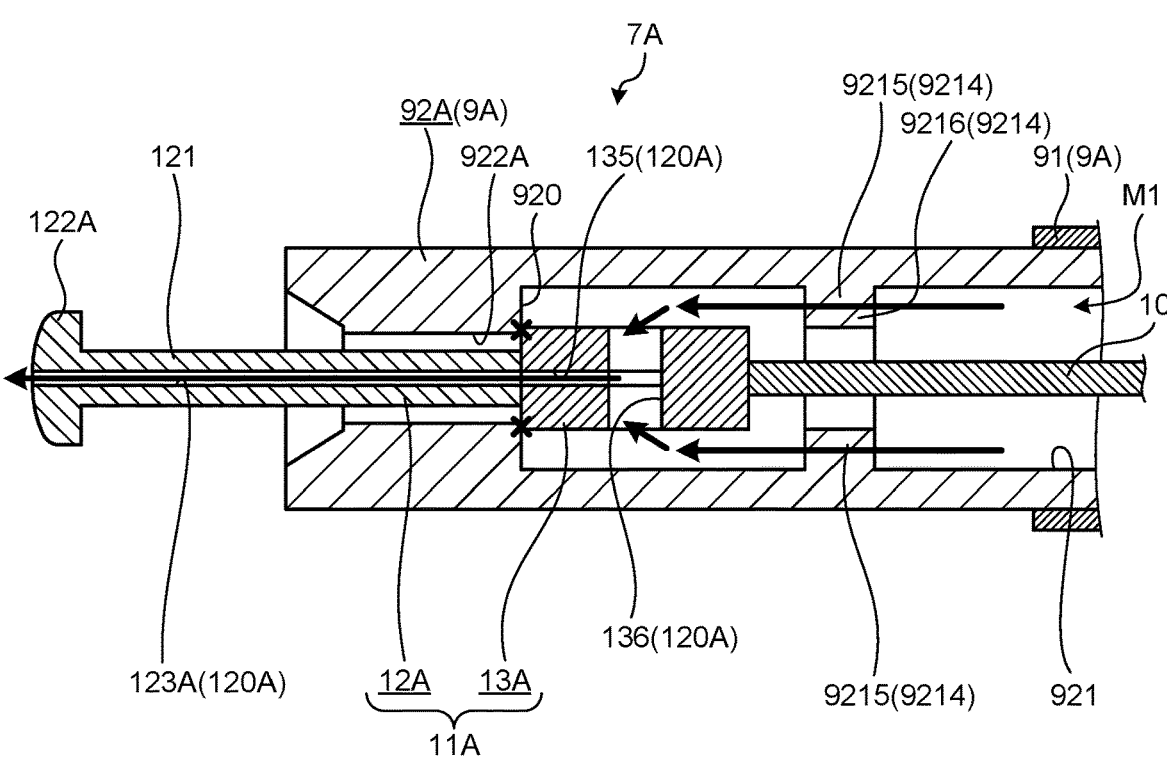
FIG. 12 is a diagram illustrating operation of an endoscope treatment tool.
Figure 13:
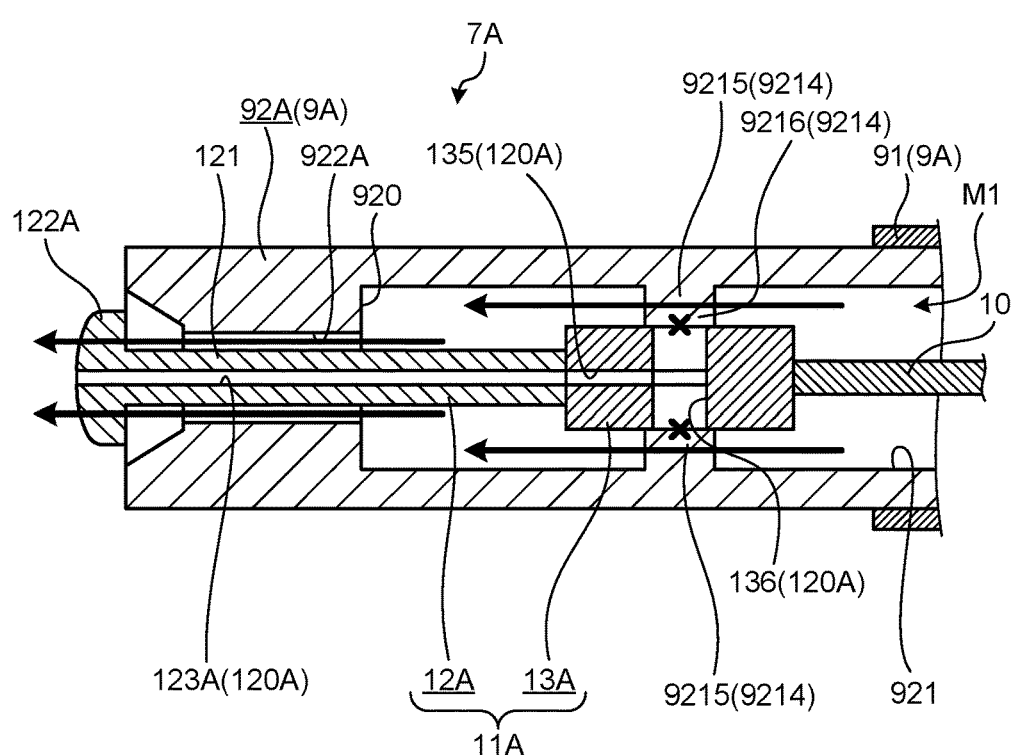
FIG. 13 is a diagram illustrating operation of the endoscope treatment tool.

FIG. 12 and FIG. 13 are diagrams illustrating the operation of the endoscope treatment tool 6. Specifically, FIG. 12 and FIG. 13 are sectional views corresponding to FIG. 10.

In this second embodiment, an operator, such as an operating surgeon, performs a local injection process as described below.

That is, the operator, such as an operating surgeon, sets a state where the knife 12A has protruded from a distal end of the sheath 9A (the distal end member 92A) by the maximum protruding length, by performing a second operation on the slider 82. In this state, the connector 13A is in contact with a bottom portion 920 (a peripheral edge portion of an opening) of the distal end member 92A. The opening of the first hole 922A is thereby closed by the connector 13A, as indicated by the marks, "x", in FIG. 12, the opening being near a proximal end of the first hole 922A. That is, the connector 13A corresponds to a second closing portion, the second closing portion enabling the opening of the first hole 922A to be closed, the opening being near the proximal end of the first hole 922A. Furthermore, the connector 13A is positioned in a distal direction from the ring portion 9216. That is, the second communicating hole 136 is not closed by an inner peripheral surface of the ring portion 9216 and is in communication with a main flow channel M1.

Subsequently, an operator, such as an operating surgeon, operates an operating unit (not illustrated in the drawings), such as a foot switch, to cause saline solution to be supplied from the water feeding source 200, while maintaining the state where the knife 12A has protruded from the distal end of the sheath 9A by the maximum protruding length through the second operation on the slider 82. The saline solution supplied from the water feeding source 200 is thereby discharged from a distal end of the knife 12A after following a flow channel through the first and second communicating holes 135 and 136 and the knife hole 123A, from the main flow channel M1, as indicated by arrows in FIG. 12. The discharged saline solution is injected below a target site T1. The target site T1 then floats up from other tissue, such as a submucosal layer below the target site T1.

A marking process and an incision process are similar to those of the first embodiment described above, and description thereof will thus be omitted.

Furthermore, when performing irrigation of the surgical site in the processes of ESD, an operator, such as an operating surgeon, performs the following operation.

The operator, such as an operating surgeon, sets a state where only the projecting portion 122A has protruded outside the distal end member 92A from the first hole 922A, by performing a first operation on the slider 82. In this state, as illustrated in FIG. 11 and FIG. 13, the connector 13A is inserted in the ring portion 9216 and the second communicating hole 136 is positioned at a position opposite to the inner peripheral surface of the ring portion 9216. That is, the inner peripheral surface of the ring portion 9216 comes into contact with the outer peripheral surface (a peripheral edge portion of an opening) of the connector 13A, and the second communicating hole 136 (an opening of the second hole 120A, the opening being near a proximal end of the second hole 120A) is thereby closed by the inner peripheral surface of the ring portion 9216, as indicated by the marks, "x", in FIG. 13. That is, the ring portion 9216 corresponds to a first closing portion, the first closing portion being arranged in the sheath 9A and enabling the opening of the incision portion 11A to be closed, the opening being near the proximal end of the incision portion 11A. By contrast, the first hole 922A is released from the closure by the connector 13A and is in communication with the main flow channel M1.

Subsequently, an operator, such as an operating surgeon, causes saline solution to be supplied from the water feeding source 200, by operating an operating unit (not illustrated in the drawings), such as a foot switch, while maintaining the state where only the projecting portion 122A has protruded outside the distal end member 92A from the first hole 922A through the first operation on the slider 82. The saline solution supplied from the water feeding source 200 is thereby discharged from the distal end of the sheath 9A and supplied to the surgical site in a body cavity, after following a flow channel through the first hole 922A from the main flow channel M1, as indicated by arrows in FIG. 13. An opening between an inner peripheral surface of the first hole 922A and an outer peripheral surface of the knife main body 121 has an area larger than that of an opening of the knife hole 123A. Therefore, the surgical site is irrigated with the saline solution discharged from the distal end of the sheath 9A (the distal end member 92A).

As described above, similarly to the above described first embodiment, in this second embodiment also, the main flow channel M1 is capable of communicating with each of the first hole 922A and the second hole 120A, near the distal end of the sheath 9A (the distal end member 92A). Furthermore, in this configuration, switching between a first mode and a second mode is enabled by advancement and retraction of the incision portion 11A according to operations on the slider 82 by an operator, such as an operating surgeon. The first mode is set by movement of the incision portion 11A toward a proximal end of the sheath 9A and is a mode where saline solution is passed to flow into a body cavity by the main flow channel M1 and the first hole 922A communicating with each other. More specifically, the first mode is a state where the main flow channel M1 and the first hole 922A are in communication with each other and the opening of the incision portion 11A is closed by the ring portion 9216, the opening being near the proximal end of the incision portion 11A. The second mode is set by movement of the incision portion 11A toward the distal end of the sheath 9A and is a mode where saline solution is passed to flow into the body cavity by the main flow channel M1 and the second hole 120A communicating with each other. More specifically, the second mode is a state where the main flow channel M1 and the second hole 120A are in communication with each other and the opening of the first hole 922A is closed by the connector 13A, the opening being near the proximal end of the first hole 922A.

In a case where the treatment tool insertion portion 7A according to the second embodiment described above is adopted also, effects similar to those of the above described first embodiment are achieved.

Modified Example of Second Embodiment

Figure 14:
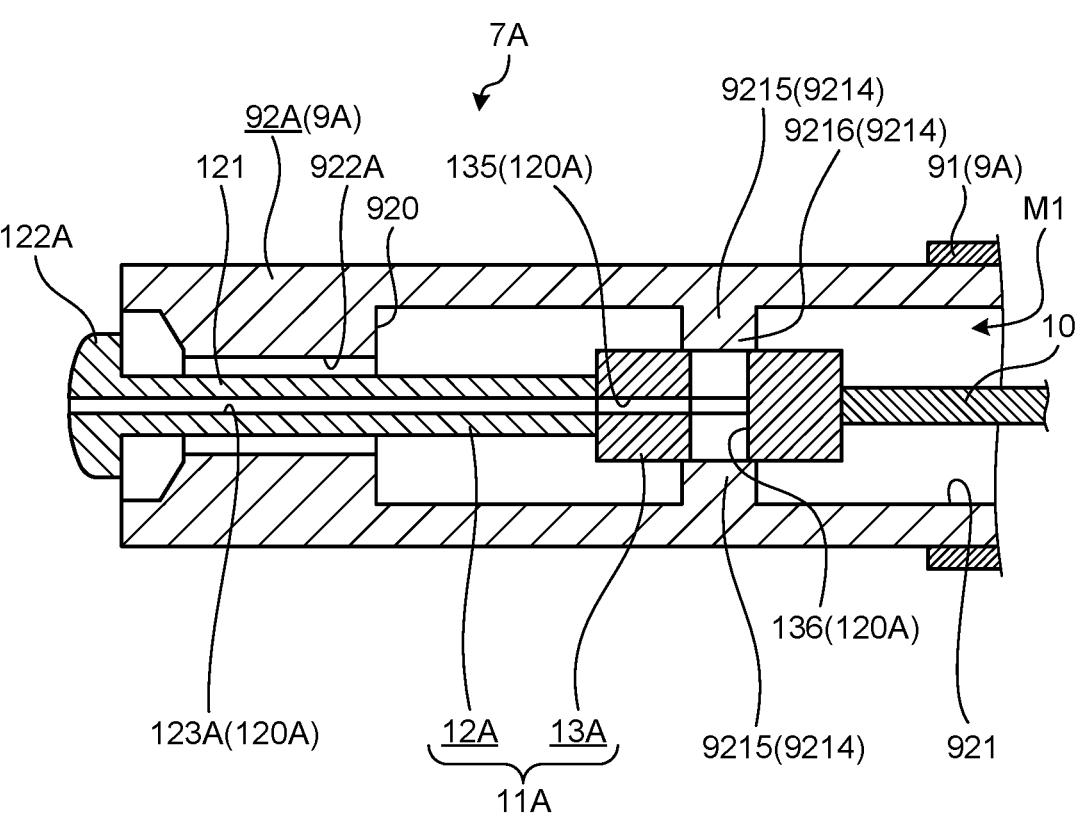
FIG. 14 is a diagram illustrating a modified example of the second embodiment.

FIG. 14 is a diagram illustrating a modified example of the second embodiment. Specifically, FIG. 14 is a sectional view corresponding to FIG. 10.

The distal end portion of the first hole 922A in the above described second embodiment may be configured to have a shape illustrated in FIG. 14. Specifically, a distal end portion of a first hole 922A according to the modified example illustrated in FIG. 14 linearly extends toward a distal end thereof along a central axis of a distal end member 92A, in a state of having the same diameter dimension after increasing in diameter toward the distal end.

Third Embodiment

A third embodiment will be described next.

In the following description, any component that is the same as that of the above described first embodiment will be assigned with the same reference sign, and detailed description thereof will be omitted or simplified.

The distal end portion of the treatment tool insertion portion 7 of the endoscope treatment tool 6, described above with respect to the first embodiment, is differently configured in an endoscope treatment tool 6, according to the third embodiment. For convenience of explanation, a treatment tool insertion portion according to the third embodiment will hereinafter be referred to as a treatment tool insertion portion 7B.

Figure 15:
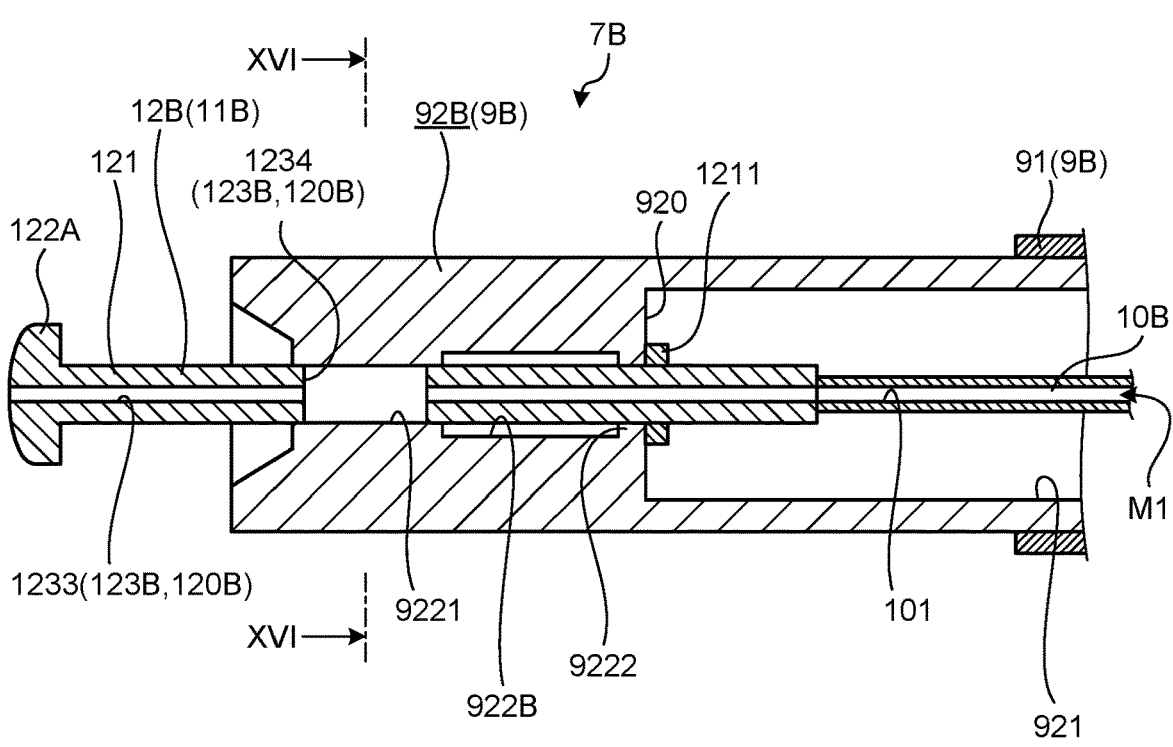
FIG. 15 is a diagram illustrating a configuration of a treatment tool insertion portion according to a third embodiment.
Figure 16:
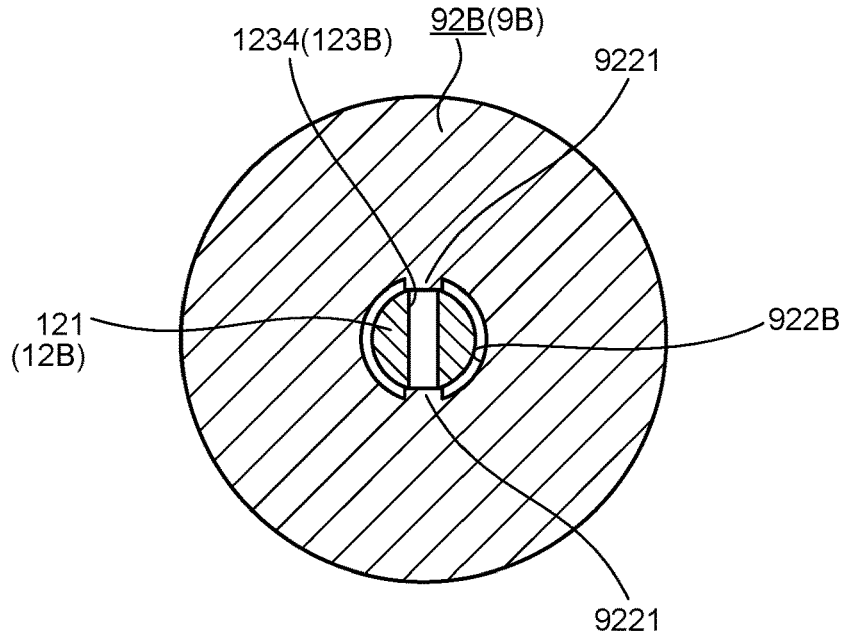
FIG. 16 is a diagram illustrating the configuration of the treatment tool insertion portion according to the third embodiment.

FIG. 15 and FIG. 16 are diagrams illustrating a configuration of the treatment tool insertion portion 7B according to the third embodiment. Specifically, FIG. 15 is a sectional view corresponding to FIG. 2. FIG. 16 is a sectional view of the treatment tool insertion portion 7B at a position of a line XVI-XVI illustrated in FIG. 15.

The sheath 9, the wire 10, and the incision portion 11, of the treatment tool insertion portion 7 described above with respect to the first embodiment are differently configured in the treatment tool insertion portion 7B, as illustrated in FIG. 15 and FIG. 16. For convenience of explanation, a sheath, a wire, and an incision portion, according to the third embodiment, will hereinafter be referred to as a sheath 9B, a wire 10B, and an incision portion 11B, respectively.

As illustrated in FIG. 15 and FIG. 16, the distal end member 92 of the sheath 9 described above with respect to the first embodiment is differently shaped in the sheath 9B. For convenience of explanation, a distal end member according to the third embodiment will hereinafter be referred to as a distal end member 92B.

The distal end member 92B may be formed of a single part or may be formed of a combination of plural parts.

As illustrated in FIG. 15, the first and second wall portions 9211 and 9212 of the distal end member 92 described above with respect to the first embodiment are omitted from the distal end member 92B, as illustrated in FIG. 15.

Furthermore, as illustrated in FIG. 15 and FIG. 16, the first hole 922 in the distal end member 92 described above with respect to the first embodiment is differently shaped in the distal end member 92B. For convenience of explanation, a first hole according to the third embodiment will hereinafter be referred to as a first hole 922B.

The first hole 922B has a circular cross-section and extends linearly along a central axis of the distal end member 92B. Furthermore, as illustrated in FIG. 15, a distal end portion of the first hole 922B increases in diameter toward a distal end of the first hole 922B. The dimension of the inner diameter of a proximal end portion of the first hole 922B is set smaller than the dimension of the inner diameter of an inner peripheral surface 921. Furthermore, the dimension of the inner diameter of the distal end portion of the first hole 922B is set larger than the dimension of the outer diameter of a projecting portion 122A. In addition, the dimension of the inner diameter of the first hole 922B is set larger than the dimension of the outer diameter of a knife main body 121. The first hole 922B may preferably be positioned on the central axis of the distal end member 92B.

Furthermore, a pair of fourth wall portions 9221 (FIG. 15 and FIG. 16) and a fifth wall portion 9222 (FIG. 15) are provided on an inner surface of the first hole 922B.

As illustrated in FIG. 15 and FIG. 16, the pair of fourth wall portions 9221 are walls each protruding toward a central axis of the first hole 922B from upper and lower portions in FIG. 15 and FIG. 16 on the inner surface of the first hole 922B, the upper and inner portions being opposite to each other. The dimension of the distance between tips of the pair of fourth wall portions 9221 is set slightly larger than the dimension of the outer diameter of the knife main body 121.

The fifth wall portion 9222 is a ring-shaped wall having the same axis as the central axis of the first hole 922B. The dimension of the inner diameter of the fifth wall portion 9222 is set slightly larger than the dimension of the outer diameter of the knife main body 121.

As illustrated in FIG. 15, the wire 10B is differently shaped from the wire 10 described above with respect to the first embodiment and has a cylindrical shape. Furthermore, a through hole 101 in the wire 10B communicates with the water feeding port 812. The through hole 101 functions as a main flow channel M1, the main flow channel M1 being where saline solution supplied from the water feeding source 200 flows through via the tube TU and the water feeding port 812.

As illustrated in FIG. 15 and FIG. 16, the connector 13 of the incision portion 11 described above with respect to the first embodiment is omitted, and the knife 12 of the incision portion 11 is differently shaped, in the incision portion 11B. For convenience of explanation, a knife according to the third embodiment will hereinafter be referred to as a knife 12B.

As illustrated in FIG. 15, the knife 12B has an outer shape that is the same as that of the knife 12A described above with respect to the second embodiment. That is, the knife 12B includes the knife main body 121 and the projecting portion 122A. The knife main body 121 is directly connected to the wire 10B. In this third embodiment, a proximal end portion of an outer peripheral surface of the knife main body 121 has an abutting portion 1211 provided thereon, the abutting portion 1211 protruding from the outer peripheral surface, extending over the entire periphery of the knife main body 121, and being ring-shaped, the entire periphery being along a circumferential direction and about a central axis of the knife main body 121.

Furthermore, as illustrated in FIG. 15, the knife hole 123A in the knife 12A described above with respect to the second embodiment is differently shaped in the knife 12B. For convenience of explanation, a knife hole according to the third embodiment will hereinafter be referred to as a knife hole 123B.

The knife hole 123B includes a second hole main body 1233 (FIG. 15) and a communicating hole 1234 (FIG. 15 and FIG. 16).

As illustrated in FIG. 15, the second hole main body 1233 is positioned on the central axis of the knife main body 121 and linearly penetrates the knife main body 121 from a proximal end of the knife main body 121 to a distal end face of the projecting portion 122A. In a state where the knife main body 121 and the wire 10B have been connected to each other, the second hole main body 1233 is in communication with the through hole 101.

The communicating hole 1234 is an I-shaped hole that is positioned at an approximately central portion of the longitudinal length of the knife main body 121, communicates with the second hole main body 1233, extends along a vertical direction (a radial direction of the knife main body 121) in FIG. 15 and FIG. 16, and is open on the outer peripheral surface of the knife main body 121.

The knife hole 123B described above corresponds to a second hole 120B (FIG. 15).

Operation of an endoscope treatment tool 6, according to the third embodiment, will be described next. For convenience of explanation, a flow of ESD will hereinafter be described as an example, similarly to the above described first embodiment.

Figure 17:
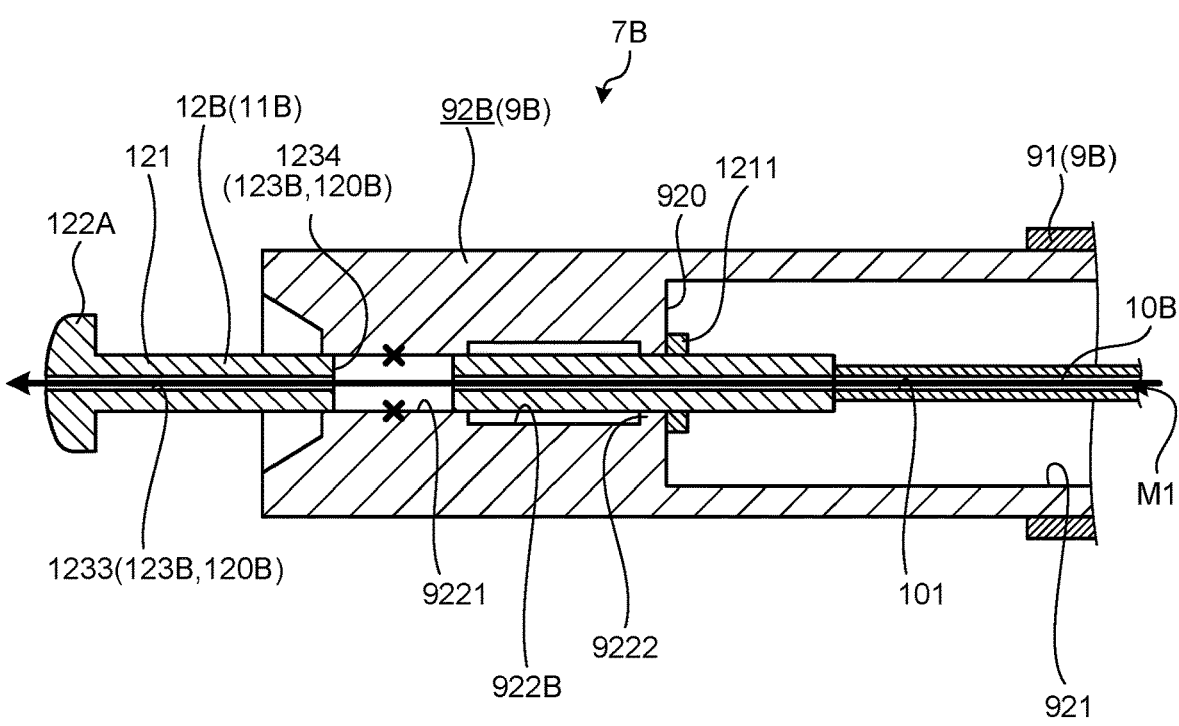
FIG. 17 is a diagram illustrating operation of an endoscope treatment tool.
Figure 18:
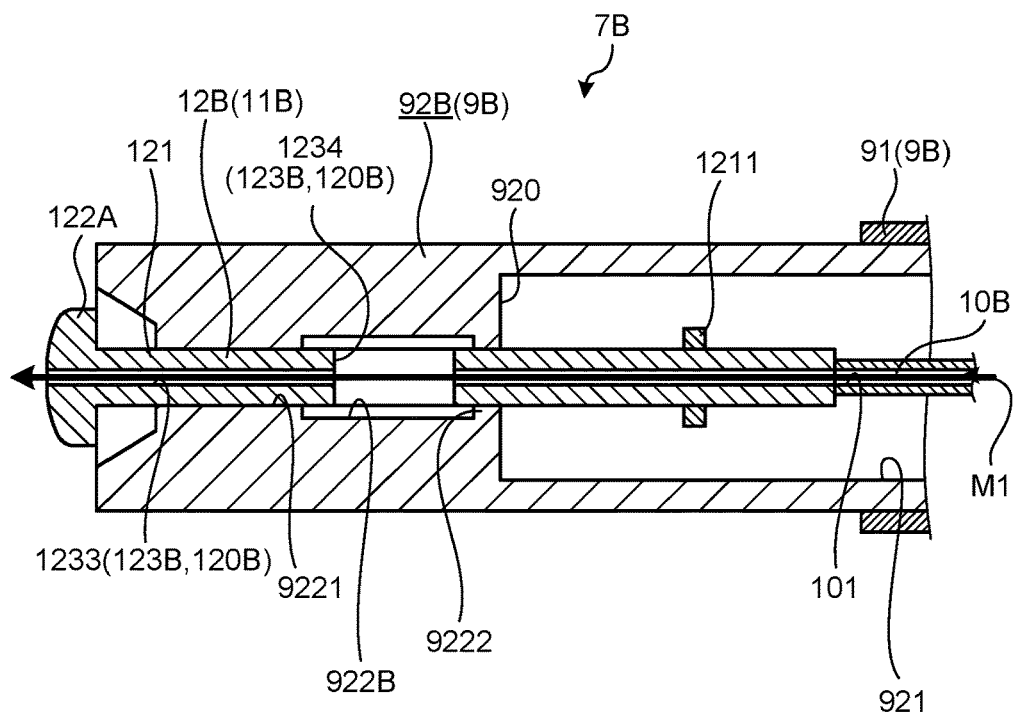
FIG. 18 is a diagram illustrating operation of the endoscope treatment tool.

FIG. 17 and FIG. 18 are diagrams illustrating the operation of the endoscope treatment tool 6. Specifically, FIG. 17 and FIG. 18 are sectional views corresponding to FIG. 15.

In this third embodiment, an operator, such as an operating surgeon, performs a local injection process as described below.

That is, the operator, such as an operating surgeon, sets a state where the knife 12B has protruded from a distal end of the sheath 9B (the distal end member 92B) by the maximum protruding length, by performing a second operation on the slider 82. In this state, the abutting portion 1211 is in contact with a bottom portion 920 (a peripheral edge portion of an opening) of the distal end member 92B. The knife 12B is thereby restricted from moving to a distal end. Furthermore, the communicating hole 1234 is positioned at a position opposite to the pair of fourth wall portions 9221. In this state, the pair of fourth wall portions 9221 are in contact with the outer peripheral surface (the peripheral edge portion of the opening) of the knife main body 121 and a flow channel between the first hole 922B and the communicating hole 1234 is thereby blocked by the pair of fourth wall portions 9221 as indicated by the marks, "x", in FIG. 17.

Subsequently, an operator, such as an operating surgeon, operates an operating unit (not illustrated in the drawings), such as a foot switch, to cause saline solution to be supplied from the water feeding source 200, while maintaining the state where the knife 12B has protruded from the distal end of the sheath 9B by the maximum protruding length through the second operation on the slider 82. The saline solution supplied from the water feeding source 200 is thereby discharged from a distal end of the knife 12B after following a flow channel through the knife hole 123B from the main flow channel M1, as indicated by an arrow in FIG. 17. The discharged saline solution is injected below a target site T1 by the force of the current of the saline solution. The target site T1 then floats up from other tissue, such as a submucosal layer below the target site T1.

A marking process and an incision process are similar to those of the first embodiment described above, and description thereof will thus be omitted.

Furthermore, when performing irrigation of the surgical site in the processes of the ESD, an operator, such as an operating surgeon, performs the following operation.

The operator, such as an operating surgeon, sets a state where only the projecting portion 122A has protruded outside the distal end member 92B from the first hole 922B, by performing a first operation on the slider 82. In this state, the communicating hole 1234 is positioned at a position displaced from the position opposite to the pair of fourth wall portions 9221, as illustrated in FIG. 18. The communicating hole 1234 is thereby in communication with the first hole 922B.

Subsequently, an operator, such as an operating surgeon, causes saline solution to be supplied from the water feeding source 200, by operating an operating unit (not illustrated in the drawings), such as a foot switch, while maintaining the state where only the projecting portion 122A has protruded outside the distal end member 92B from the first hole 922B through the first operation on the slider 82. The saline solution supplied from the water feeding source 200 is thereby discharged from the distal end of the knife 12B after following the flow channel through the knife hole 123B from the main flow channel M1 as indicated by an arrow in FIG. 18, and discharged from the distal end of the sheath 9B after following a flow channel through the knife hole 123B, communicating hole 1234, and first hole 922B, from the main flow channel M1, to be supplied to the surgical site. The saline solution that has followed the main flow channel M1 is discharged from both the knife hole 123B and the first hole 922B. Therefore, the surgical site is irrigated with the saline solution discharged from both the knife hole 123B and the first hole 922B.

As described above, similarly to the above described first embodiment, in this third embodiment also, the main flow channel M1 is capable of communicating with each of the first hole 922B and the second hole 120B, near the distal end of the sheath 9B (the distal end member 92B). Furthermore, in this configuration, switching between a first mode and a second mode is enabled by advancement and retraction of the incision portion 11B according to operations on the slider 82 by an operator, such as an operating surgeon. The first mode is set by movement of the incision portion 11B toward a proximal end of the sheath 9B and is a mode where saline solution is passed to flow into a body cavity by the main flow channel M1 communicating with the first hole 922B and the second hole 120B. The second mode is set by movement of the incision portion 11B toward the distal end of the sheath 9B and is a mode where saline solution is passed to flow into the body cavity by the main flow channel M1 communicating with the second hole 120B.

In a case where the treatment tool insertion portion 7B according to the third embodiment described above is adopted also, effects similar to those of the above described first embodiment are achieved.

Fourth Embodiment

A fourth embodiment will be described next.

In the following description, any component that is the same as that of the above described first embodiment will be assigned with the same reference sign, and detailed description thereof will be omitted or simplified.

The distal end portion of the treatment tool insertion portion 7 in the endoscope treatment tool 6, described above with respect to the first embodiment, is differently configured in an endoscope treatment tool 6, according to the fourth embodiment. For convenience of explanation, a treatment tool insertion portion according to the fourth embodiment will hereinafter be referred to as a treatment tool insertion portion 7C.

Figure 19:
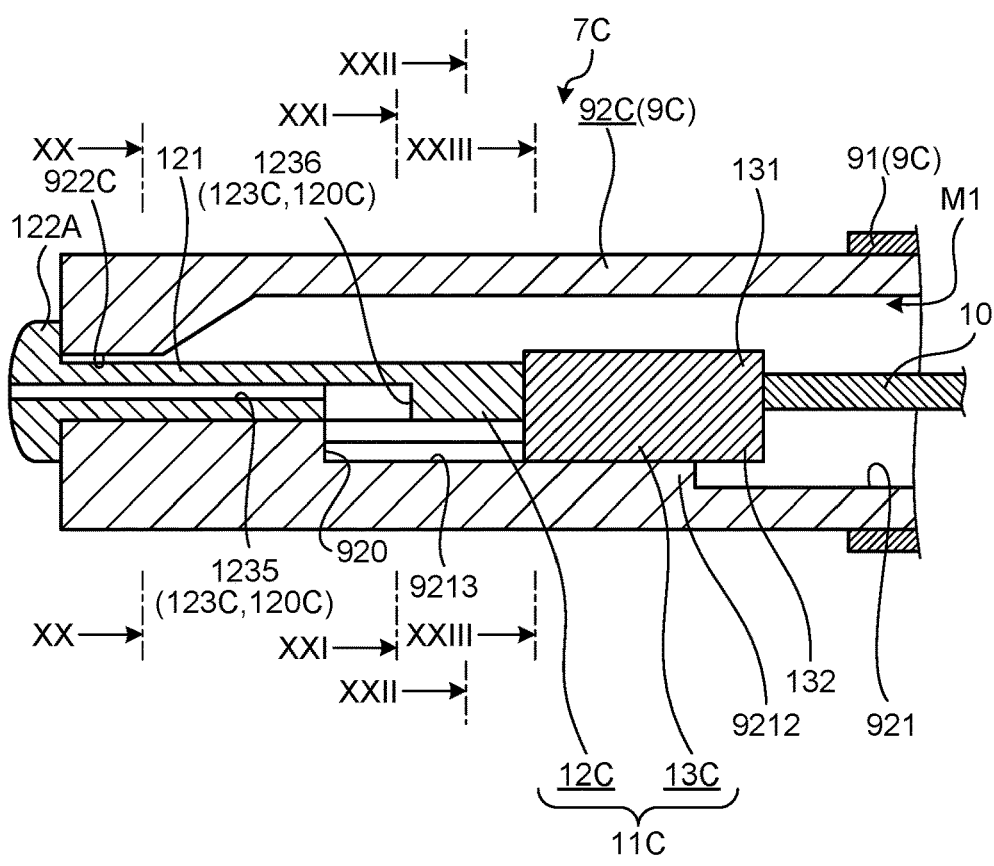
FIG. 19 is a diagram illustrating a configuration of a treatment tool insertion portion according to a fourth embodiment.
Figure 20:
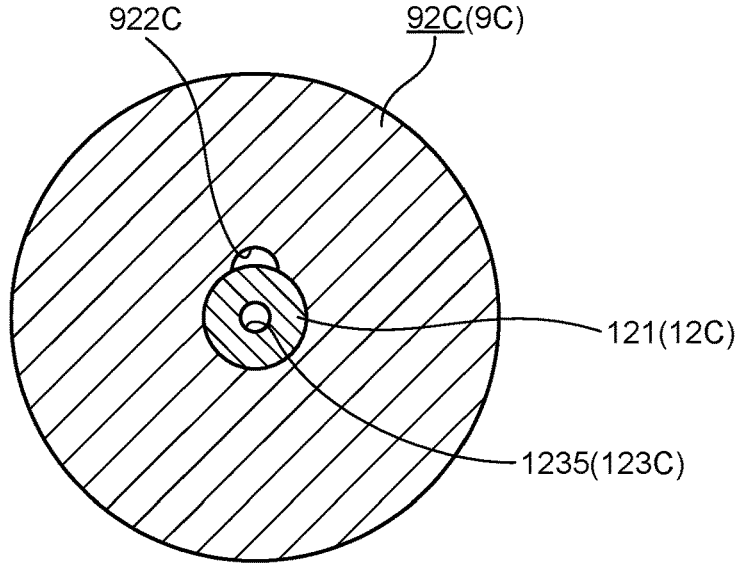
FIG. 20 is a diagram illustrating the configuration of the treatment tool insertion portion according to the fourth embodiment.
Figure 21:
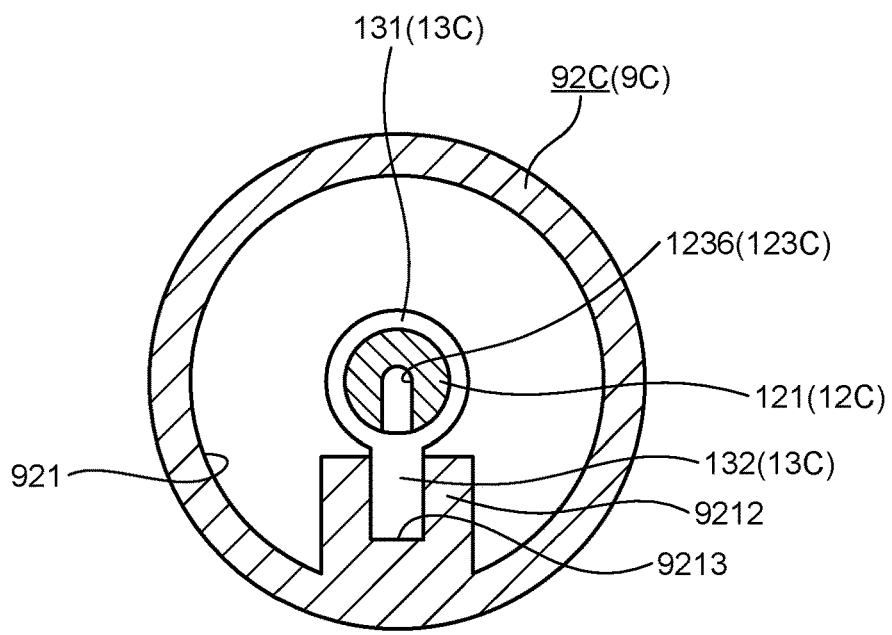
FIG. 21 is a diagram illustrating the configuration of the treatment tool insertion portion according to the fourth embodiment.
Figure 22:
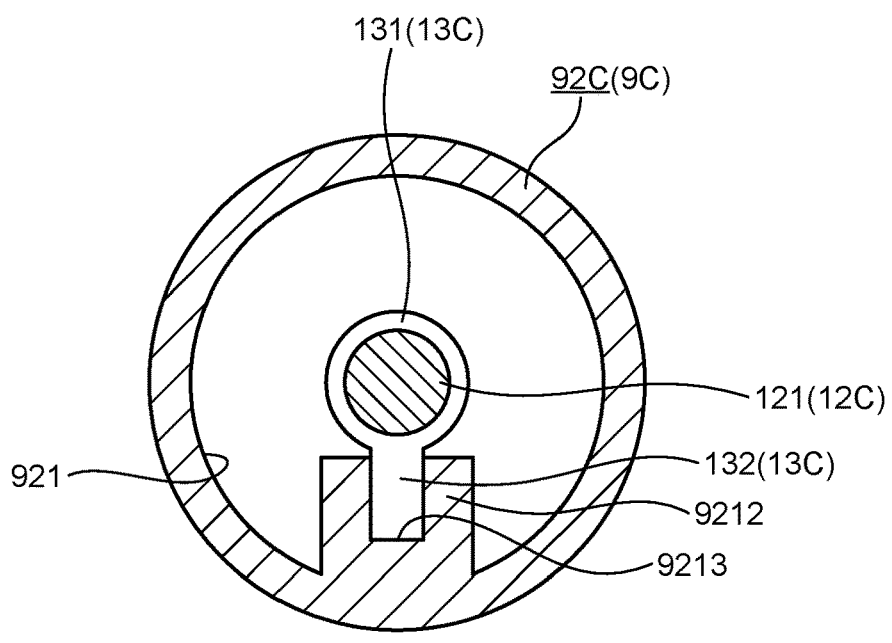
FIG. 22 is a diagram illustrating the configuration of the treatment tool insertion portion according to the fourth embodiment.
Figure 23:
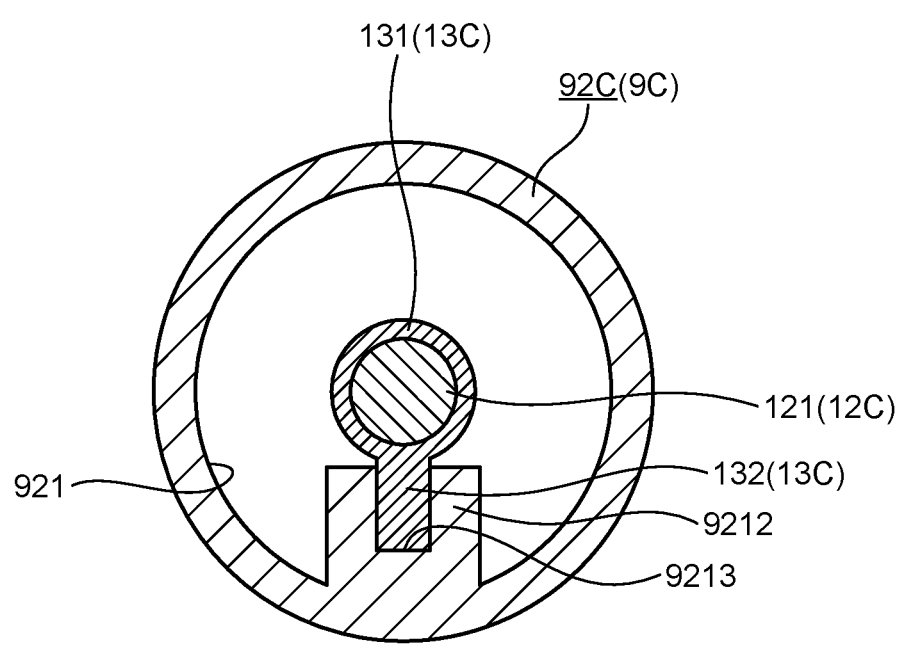
FIG. 23 is a diagram illustrating the configuration of the treatment tool insertion portion according to the fourth embodiment.

FIG. 19 to FIG. 23 are diagrams illustrating a configuration of the treatment tool insertion portion 7C according to the fourth embodiment. Specifically, FIG. 19 is a sectional view corresponding to FIG. 2. FIG. 20 is a sectional view of the treatment tool insertion portion 7C at a position of a line XX-XX illustrated in FIG. 19. FIG. 21 is a sectional view of the treatment tool insertion portion 7C at a position of a line XXI-XXI illustrated in FIG. 19. FIG. 22 is a sectional view of the treatment tool insertion portion 7C at a position of a line XXII-XXII illustrated in FIG. 19. FIG. 23 is a sectional view of the treatment tool insertion portion 7C at a position of a line XXIII-XXIII illustrated in FIG. 19.

The sheath 9 and the incision portion 11 of the treatment tool insertion portion 7 described above with respect to the first embodiment are differently configured in the treatment tool insertion portion 7C, as illustrated in FIG. 19 to FIG. 23. For convenience of explanation, a sheath and an incision portion according to the fourth embodiment will hereinafter be referred to as a sheath 9C and an incision portion 11C, respectively.

As illustrated in FIG. 19 to FIG. 23, the distal end member 92 of the sheath 9 described above with respect to the first embodiment is differently shaped in the sheath 9C. For convenience of explanation, a distal end member according to the third embodiment will hereinafter be referred to as a distal end member 92C.

The distal end member 92C may be formed of a single part or may be formed of a combination of plural parts.

The first wall portion 9211 of the distal end member 92 described above with respect to the first embodiment is omitted from the distal end member 92C, as illustrated in FIG. 19.

Furthermore, as illustrated in FIG. 19 and FIG. 20, the first hole 922 in the distal end member 92 described above with respect to the first embodiment is differently shaped in the distal end member 92C. For convenience of explanation, a first hole according to the fourth embodiment will hereinafter be referred to as a first hole 922C.

The upper shape of the first hole 922C in FIG. 19 and FIG. 20 is different from that of the first hole 922 described above with respect to the first embodiment. Specifically, an upper portion of the first hole 922C has a predetermined clearance from a knife main body 121, and the first hole 922C (an inner peripheral surface of the distal end member 92C) extends in a radial direction and communicates with a main flow channel M1.

As illustrated in FIG. 19 to FIG. 23, the knife 12 and the connector 13 of the incision portion 11 described above with respect to the first embodiment are differently shaped in the incision portion 11C. For convenience of explanation, a knife and a connector according to the fourth embodiment will hereinafter be referred to as a knife 12C and a connector 13C, respectively.

As illustrated in FIG. 19, the knife 12C has an outer shape that is the same as the knife 12A described above with respect to the second embodiment. That is, the knife 12C includes the knife main body 121 and a projecting portion 122A.

Furthermore, as illustrated in FIG. 19, the knife hole 123A in the knife 12A described above with respect to the second embodiment is differently shaped in the knife 12C. For convenience of explanation, a knife hole according to the fourth embodiment will hereinafter be referred to as a knife hole 123C.

The knife hole 123C includes a second hole main body 1235 (FIG. 19 and FIG. 20) and a communicating hole 1236 (FIG. 19 and FIG. 21).

The second hole main body 1235 extends linearly along a central axis of the knife main body 121 from a distal end face of the projecting portion 122A, in a proximal direction, as illustrated in FIG. 19. The second hole main body 1235 may preferably positioned on the central axis of the knife main body 121.

As illustrated in FIG. 19 and FIG. 21, the communicating hole 1236 communicates with a proximal end portion of the second hole main body 1235, extends toward an outer peripheral surface of the knife main body 121 in FIG. 19 and FIG. 21, and is open on the outer peripheral surface of the knife main body 121.

The knife hole 123C described above is open on an outer peripheral surface of the incision portion 11C, the outer peripheral surface being near a proximal end of the incision portion 11C, and corresponds to a second hole 120C (FIG. 19).

As illustrated in FIG. 19 and FIG. 21 to FIG. 23, the communicating hole 134 in the connector 13 described above with respect to the first embodiment is omitted from the connector 13C. For convenience of explanation, illustration of a fitting hole 133 is omitted in FIG. 19 and FIG. 21 to FIG. 23.

Operation of an endoscope treatment tool 6, according to the fourth embodiment, will be described next. For convenience of explanation, a flow of ESD will hereinafter be described as an example, similarly to the above described first embodiment.

Figure 24:
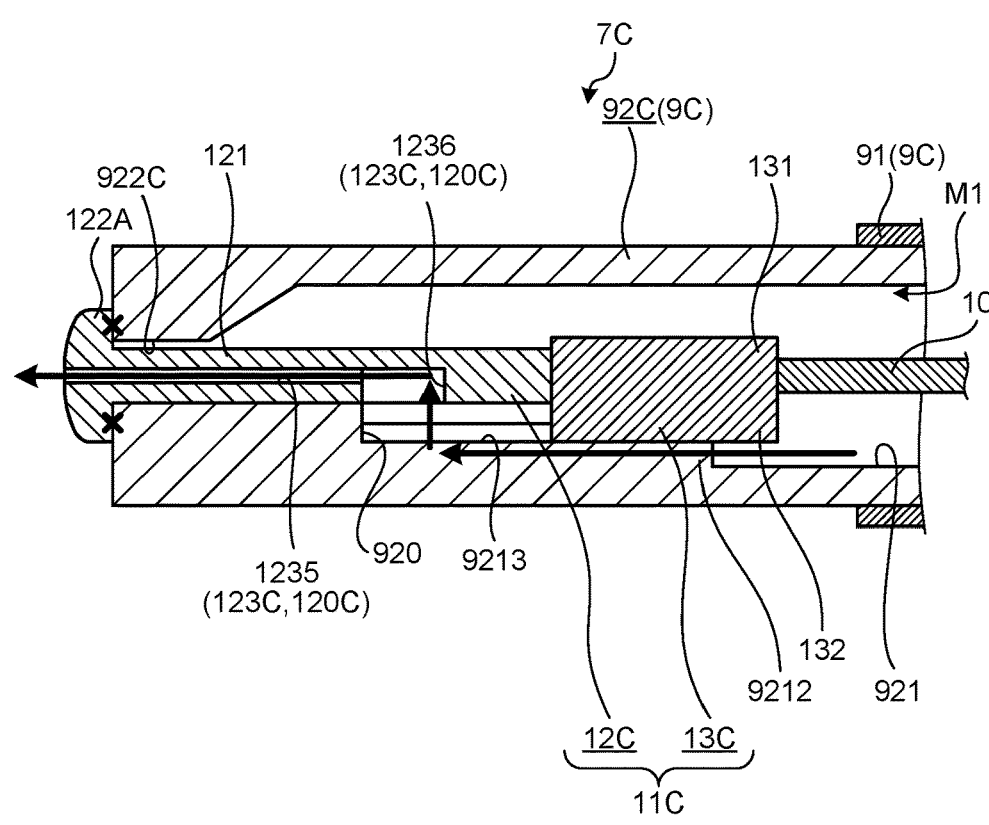
FIG. 24 is a diagram illustrating operation of an endoscope treatment tool.
Figure 25:
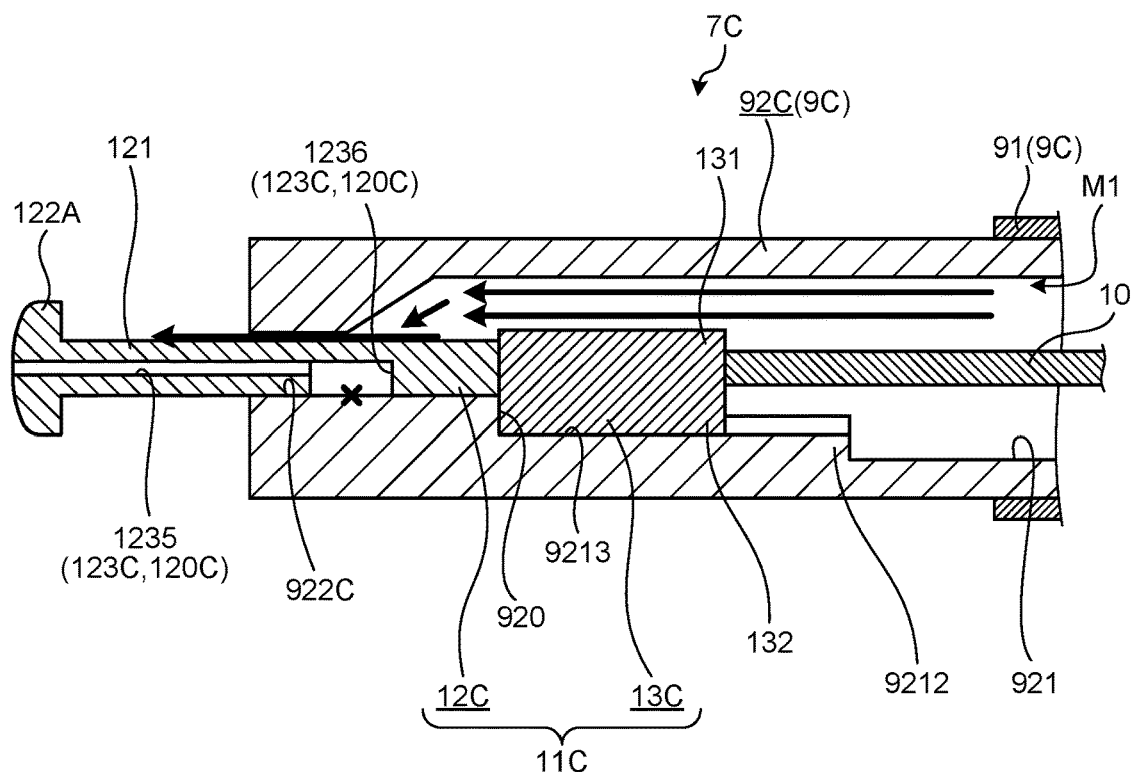
FIG. 25 is a diagram illustrating operation of the endoscope treatment tool.

FIG. 24 and FIG. 25 are diagrams illustrating the operation of the endoscope treatment tool 6. Specifically, FIG. 24 and FIG. 25 are sectional views corresponding to FIG. 19.

In this fourth embodiment, an operator, such as an operating surgeon, performs a local injection process as described below.

That is, the operator, such as an operating surgeon, sets a state where only the projecting portion 122A has protruded outside the distal end member 92C from the first hole 922C, that is, a state where the projecting portion 122A has protruded from the first hole 922C and the knife main body 121 has been positioned in the first hole 922C, by performing a first operation on the slider 82. In this state, as illustrated in FIG. 24, the communicating hole 1236 is positioned at a position separate from an inner surface of the first hole 922C and a clearance is generated. The communicating hole 1236 is thereby in communication with the main flow channel M1 via this clearance. By contrast, as indicated by the marks, "x", in FIG. 24, the projecting portion 122A is in contact with a distal end of the sheath 9C (the distal end member 92C) and the first hole 922C is thus closed near a distal end of the first hole 922C by the projecting portion 122A. That is, the projecting portion 122A corresponds to a second closing portion, the second closing portion enabling an opening of the first hole 922C to be closed, the opening being near the distal end of the first hole 922C.

Subsequently, an operator, such as an operating surgeon, causes saline solution to be supplied from the water feeding source 200, by operating an operating unit (not illustrated in the drawings), such as a foot switch, while maintaining the state where only the projecting portion 122A has protruded outside the distal end member 92C from the first hole 922C through the first operation on the slider 82. The saline solution supplied from the water feeding source 200 is thereby discharged from a distal end of the knife 12C after following a flow channel through the communicating hole 1236 and the second hole main body 1235, from the main flow channel M1, as indicted by arrows in FIG. 24. The discharged saline solution is injected below a target site T1 by the force of the current of the saline solution. The target site T1 then floats up from other tissue, such as a submucosal layer below the target site T1.

A marking process and an incision process are similar to those of the first embodiment described above, and description thereof will thus be omitted.

Furthermore, when performing irrigation of the surgical site in the processes of the ESD, an operator, such as an operating surgeon, performs the following operation.

The operator, such as an operating surgeon, sets a state where the knife 12C has protruded from the distal end of the sheath 9C by the maximum protruding length, by performing a second operation on the slider 82. In this state, as illustrated in FIG. 25, the communicating hole 1236 is positioned at a position where the communicating hole 1236 is in contact with an inner surface of the first hole 922C. A flow channel between the communicating hole 1236 and the main flow channel M1 is thereby blocked by the inner surface of the first hole 922C as indicated by the mark, "x", in FIG. 25. That is, the inner surface of the first hole 922C corresponds to a first closing portion, the first closing portion being arranged in the sheath 9C and being capable of closing an opening of the incision portion 11C, the opening being near a proximal end of the incision portion 11C. By contrast, in this state, the first hole 922C is released from the closure near the distal end of the first hole 922C by the projecting portion 122A because the projecting portion 122A is separate from the distal end of the sheath 9C (the distal end member 92C).

Subsequently, an operator, such as an operating surgeon, causes saline solution to be supplied from the water feeding source 200 by operating an operating unit (not illustrated in the drawings), such as a foot switch, while maintaining the state where the knife 12C has protruded from the distal end of the sheath 9C by the maximum protruding length through the second operation on the slider 82. The saline solution supplied from the water feeding source 200 is thereby discharged from the distal end of the sheath 9C and supplied to the surgical site, after following a flow channel through the first hole 922C from the main flow channel M1, as indicated by arrows in FIG. 25. An opening between the inner peripheral surface of the first hole 922C and the outer peripheral surface of the knife main body 121 has an area larger than that of an opening of the second hole main body 1235. Therefore, the surgical site is irrigated with the saline solution discharged from the distal end of the sheath 9C (the distal end member 92C).

As described above, in this fourth embodiment, similarly to the above described first embodiment, the main flow channel M1 is capable of communicating with each of the first hole 922C and the second hole 120C, near the distal end of the sheath 9C (the distal end member 92C). Furthermore, in this configuration, switching between a first mode and a second mode is enabled by advancement and retraction of the incision portion 11C according to operations on the slider 82 by an operator, such as an operating surgeon. The first mode is set by movement of the incision portion 11C toward the distal end of the sheath 9C and is a mode where saline solution is passed to flow into a body cavity by the main flow channel M1 and the first hole 922C communicating with each other. More specifically, the first mode is a state where the main flow channel M1 and the first hole 922C are in communication with each other and the opening of the incision portion 11C is closed by the inner surface of the first hole 922C, the opening being near the proximal end of the incision portion 11C. The second mode is set by movement of the incision portion 11C toward a proximal end of the sheath 9C and is a mode where saline solution is passed to flow into the body cavity by the main flow channel M1 and the second hole 120C communicating with each other. More specifically, the second mode is a state where the main flow channel M1 and the second hole 120C are in communication with each other and the opening of the first hole 922C is closed by the projecting portion 122A, the opening being near the distal end of the first hole 922C.

In a case where the treatment tool insertion portion 7C according to the fourth embodiment described above is adopted also, effects similar to those of the above described first embodiment are achieved.

Fifth Embodiment

A fifth embodiment will be described next.

In the following description, any component that is the same as that of the above described first embodiment will be assigned with the same reference sign, and detailed description thereof will be omitted or simplified.

The distal end portion of the treatment tool insertion portion 7 in the endoscope treatment tool 6, described above with respect to the first embodiment, is differently configured in an endoscope treatment tool 6, according to the fifth embodiment. For convenience of explanation, a treatment tool insertion portion according to the fifth embodiment will hereinafter be referred to as a treatment tool insertion portion 7D.

Figure 26:
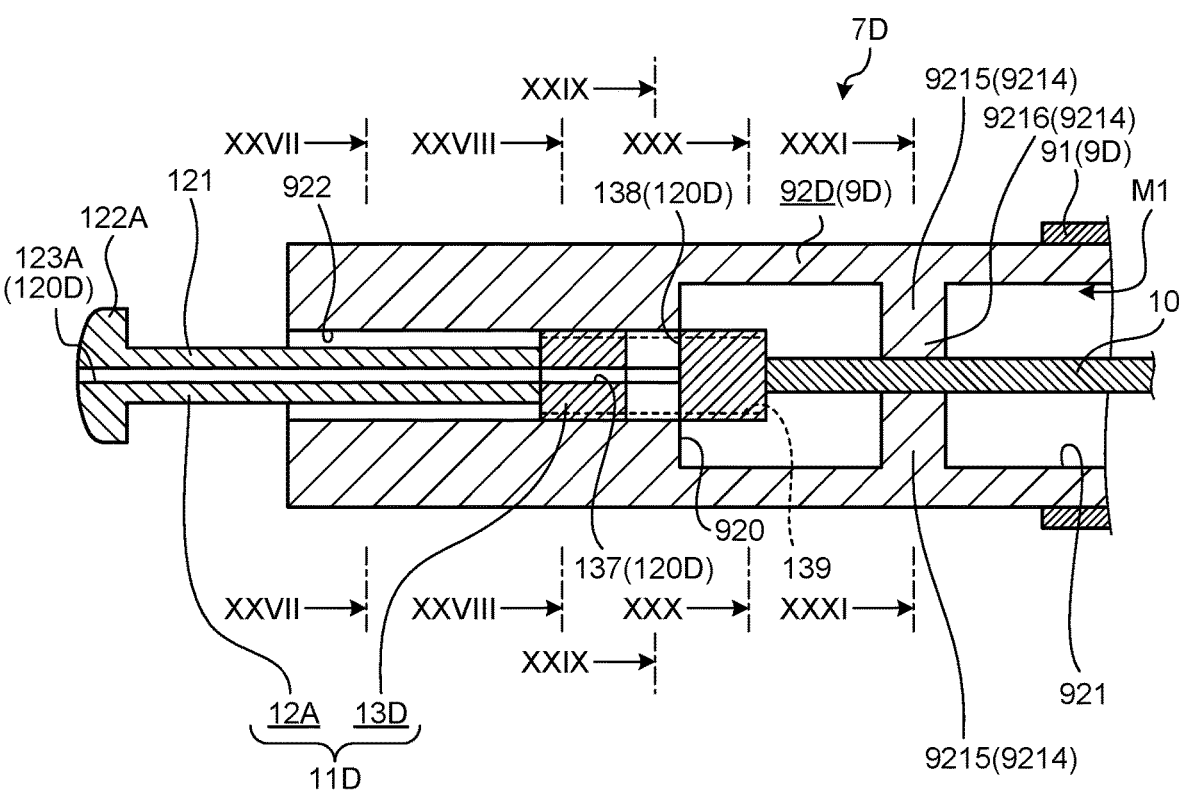
FIG. 26 is a diagram illustrating a configuration of a treatment tool insertion portion according to a fifth embodiment.
Figure 27:
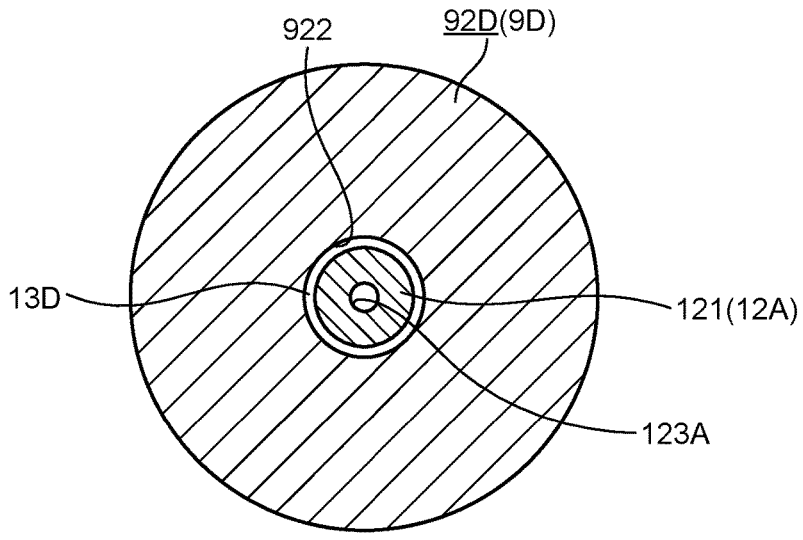
FIG. 27 is a diagram illustrating the configuration of the treatment tool insertion portion according to the fifth embodiment.
Figure 28:
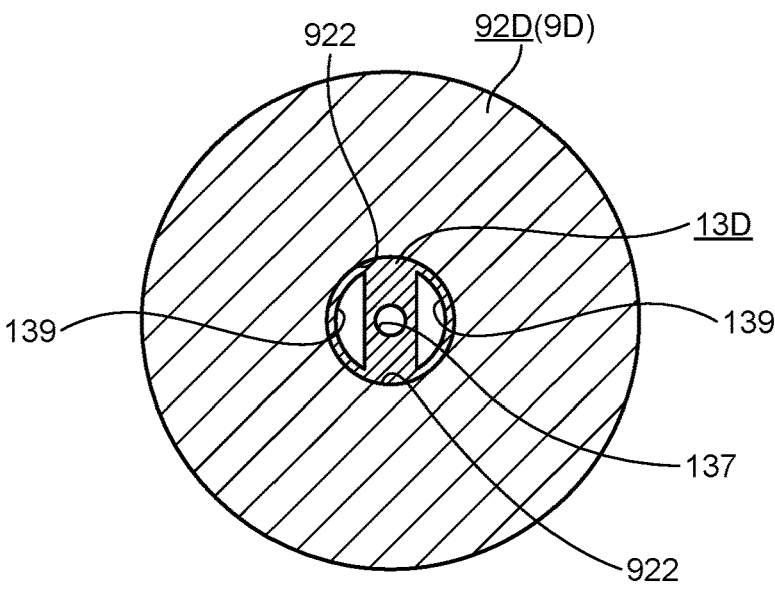
FIG. 28 is a diagram illustrating the configuration of the treatment tool insertion portion according to the fifth embodiment.
Figure 29:
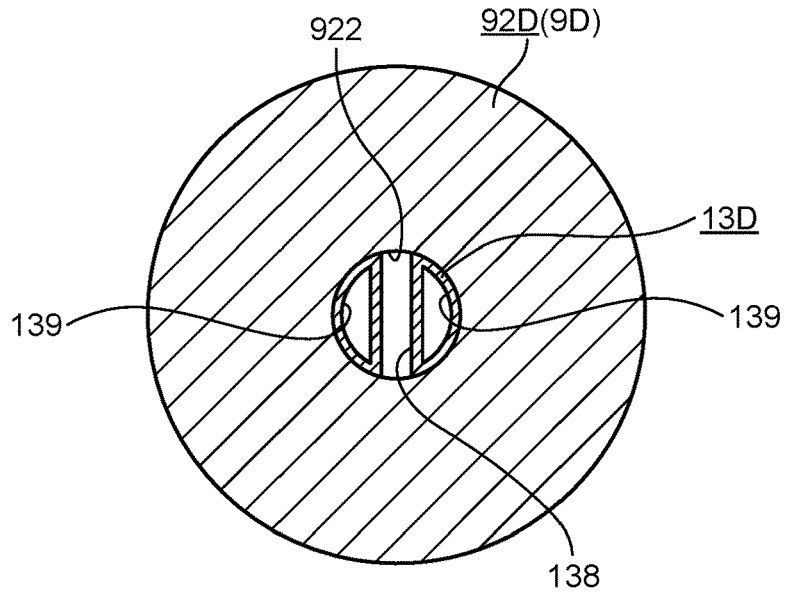
FIG. 29 is a diagram illustrating the configuration of the treatment tool insertion portion according to the fifth embodiment.
Figure 30:
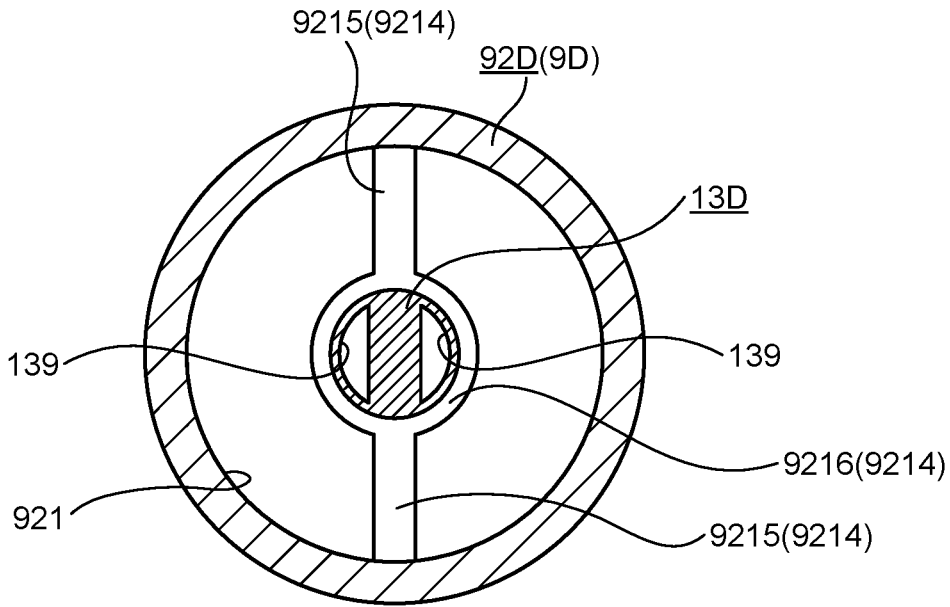
FIG. 30 is a diagram illustrating the configuration of the treatment tool insertion portion according to the fifth embodiment.
Figure 31:
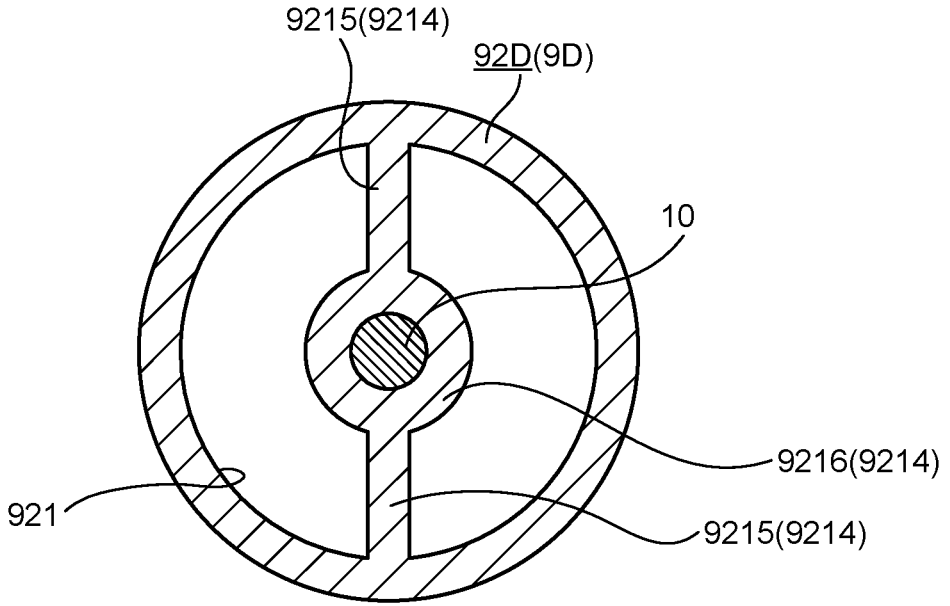
FIG. 31 is a diagram illustrating the configuration of the treatment tool insertion portion according to the fifth embodiment.

FIG. 26 to FIG. 31 are diagrams illustrating a configuration of the treatment tool insertion portion 7D according to the fifth embodiment. Specifically, FIG. 26 is a sectional view corresponding to FIG. 2. FIG. 27 is a sectional view of the treatment tool insertion portion 7D at a position of a line XXVII-XXVII illustrated in FIG. 26. FIG. 28 is a sectional view of the treatment tool insertion portion 7D at a position of a line XXVIII-XXVIII illustrated in FIG. 26. FIG. 29 is a sectional view of the treatment tool insertion portion 7D at a position of a line XXIX-XXIX illustrated in FIG. 26. FIG. 30 is a sectional view of the treatment tool insertion portion 7D at a position of a line XXX-XXX illustrated in FIG. 26. FIG. 31 is a sectional view of the treatment tool insertion portion 7D at a position of a line XXXI-XXXI illustrated in FIG. 26.

The sheath 9 and the incision portion 11 of the treatment tool insertion portion 7 described above with respect to the first embodiment are differently configured in the treatment tool insertion portion 7D, as illustrated in FIG. 26 to FIG. 31. For convenience of explanation, a sheath and an incision portion according to the fifth embodiment will hereinafter be referred to as a sheath 9D and an incision portion 11D, respectively.

As illustrated in FIG. 26 to FIG. 31, the distal end member 92 of the sheath 9 described above with respect to the first embodiment is differently shaped in the sheath 9D. For convenience of explanation, a distal end member according to the fifth embodiment will hereinafter be referred to as a distal end member 92D.

The distal end member 92D may be formed of a single part or may be formed of a combination of plural parts.

As illustrated in FIG. 26 and FIG. 31, the third wall portion 9214 described above with respect to the second embodiment is provided in the distal end member 92D, instead of the first and second wall portions 9211 and 9212 in the distal end member 92 described above with respect to the first embodiment. A wire 10 is inserted in a ring portion 9216 forming the third wall portion 9214 in this fifth embodiment, as illustrated in FIG. 31.

As illustrated in FIG. 26 to FIG. 30, the knife 12A described above with respect to the second embodiment is adopted in the incision portion 11D, instead of the knife 12 in the incision portion 11 described above with respect to the first embodiment, and the connector 13 in the incision portion 11 is also shaped differently in the incision portion 11D. For convenience of explanation, a connector according to the fifth embodiment will hereinafter be referred to as a connector 13D.

The connector 13D is formed of a cylindrical member extending linearly along a central axis of the distal end member 92D. The dimension of the outer diameter of the connector 13D is set slightly smaller than the dimension of the inner diameter of the first hole 922 and larger than the dimension of the inner diameter of the ring portion 9216. Furthermore, as illustrated in FIG. 26, FIG. 28, and FIG. 29, first and second communicating holes 137 and 138 and a pair of third communicating holes 139 are provided in the connector 13D. The connector 13D may preferably be positioned on the central axis of the distal end member 92D.

The first communicating hole 137 extends linearly along a central axis of the connector 13D from a distal end of the connector 13D toward a proximal end of the connector 13D, as illustrated in FIG. 26. In a state where the connector 13D and a knife main body 121 have been connected to each other, the first communicating hole 137 is in communication with a knife hole 123A. The first communicating hole 137 may preferably be positioned on the central axis of the connector 13D.

The second communicating hole 138 is positioned at an approximately central portion of the longitudinal length of the connector 13D, communicates with the first communicating hole 137, extends in a vertical direction (a radial direction of the connector 13D) in FIG. 26 and FIG. 29, and is an I-shaped hole that is open on an outer peripheral surface of the connector 13D.

The knife hole 123A and the first and second communicating holes 137 and 138 described above are open on an outer peripheral surface of the incision portion 11D, the outer peripheral surface being near a proximal end of the incision portion 11D, and correspond to a second hole 120D (FIG. 26).

As illustrated in FIG. 28, the pair of third communicating holes 139 are positioned on both sides of the first communicating hole 137 and are holes linearly penetrating the connector 13D along the central axis of the connector 13D from the distal end to the proximal end of the connector 13D. The pair of third communicating holes 139 do not communicate with the first and second communicating holes 137 and 138.

Operation of an endoscope treatment tool 6, according to the fifth embodiment, will be described next. For convenience of explanation, a flow of ESD will hereinafter be described as an example, similarly to the above described first embodiment.

Figure 32:
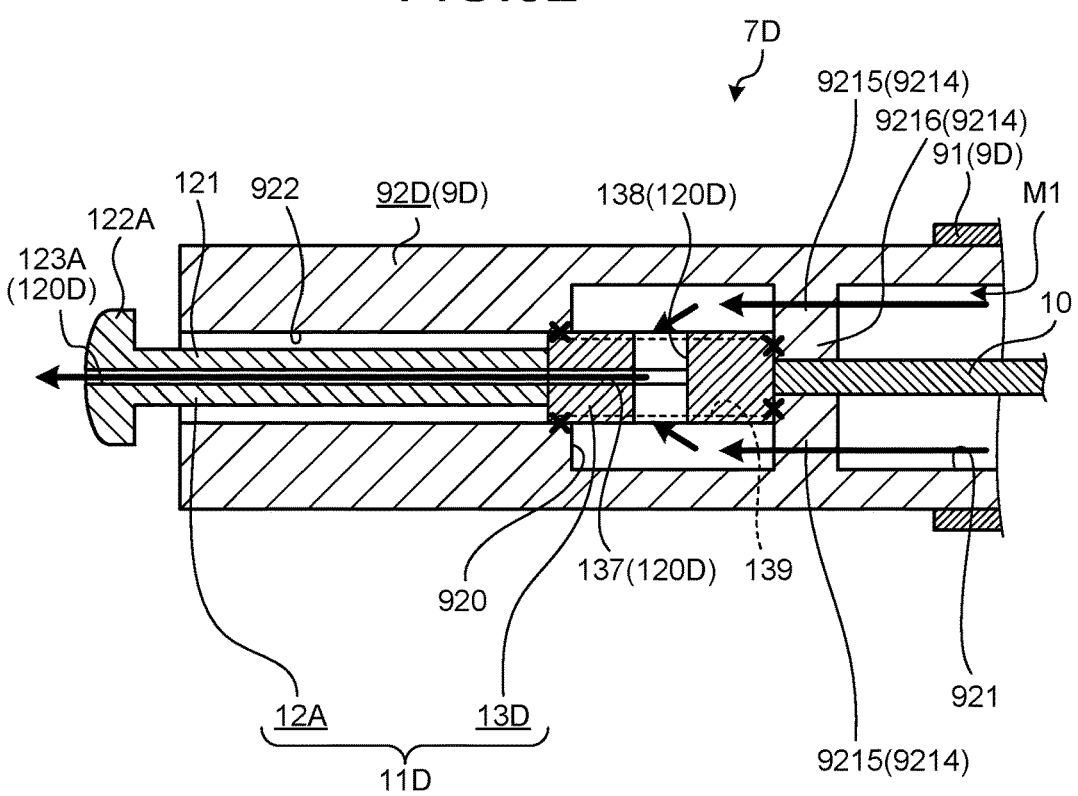
FIG. 32 is a diagram illustrating operation of an endoscope treatment tool.
Figure 33:
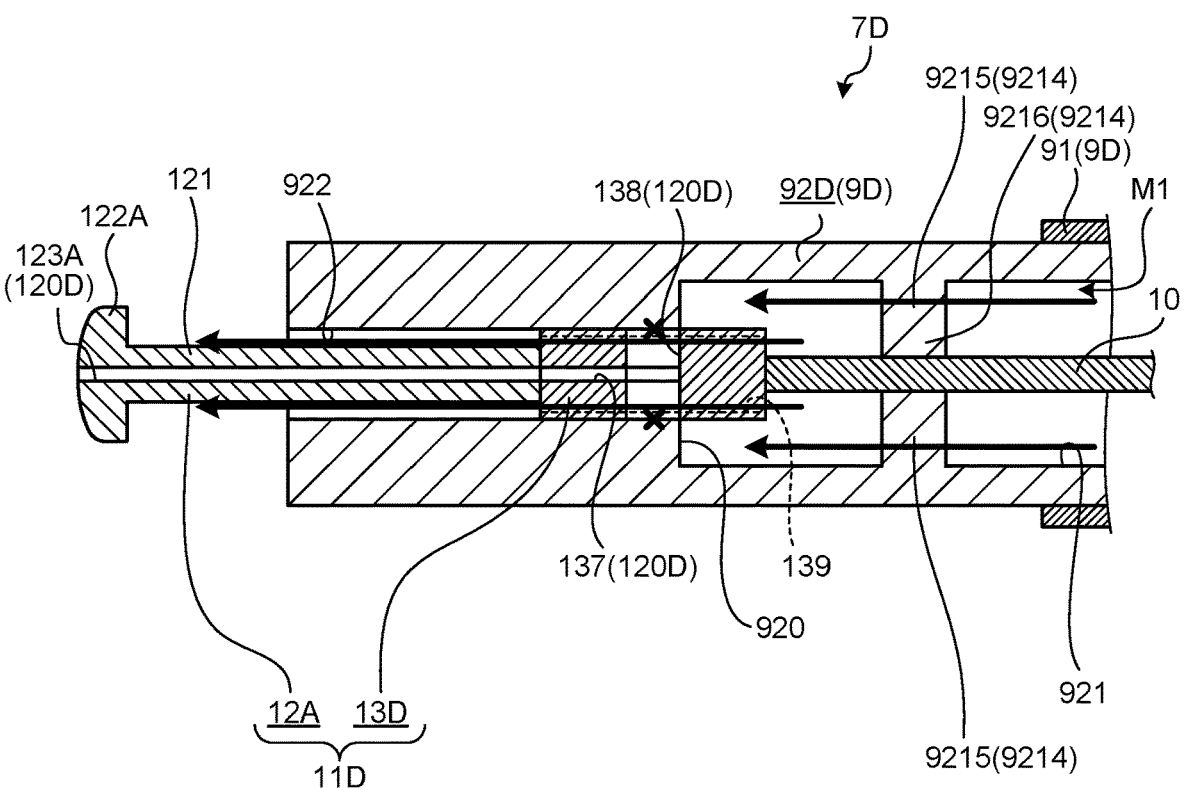
FIG. 33 is a diagram illustrating operation of the endoscope treatment tool.

FIG. 32 and FIG. 33 are diagrams illustrating the operation of the endoscope treatment tool 6. Specifically, FIG. 32 and FIG. 33 are sectional views corresponding to FIG. 26.

In this fifth embodiment, an operator, such as an operating surgeon, performs a local injection process as described below.

That is, the operator, such as an operating surgeon, sets a state where only a projecting portion 122A has protruded outside the distal end member 92D from a first hole 922, that is, a state where the projecting portion 122A has protruded from the first hole 922 and the knife main body 121 has been positioned in the first hole 922, by performing a first operation on the slider 82. In this state, as illustrated in FIG. 32, a distal end portion of the connector 13D has been inserted in the first hole 922 and the proximal end of the connector 13D is in contact with a distal end face of the ring portion 9216. In this state, the distal end portion of the connector 13D has been inserted in the first hole 922, the pair of third communicating holes 139 are closed by the ring portion 9216, and a flow channel between the first hole 922 and a main flow channel M1 is thereby blocked by the connector 13D as indicated by the marks, "x" in FIG. 32. That is, the connector 13D corresponds to a third closing portion, the third closing portion enabling an opening of the first hole 922 to be closed, the opening being near a proximal end of the first hole 922. Furthermore, a flow channel between the pair of third communicating holes 139 and the main flow channel M1 is blocked by the ring portion 9216, as indicated by the marks, "x", in FIG. 32. In contrast, the second communicating hole 138 is positioned at a position displaced from an inner surface of the first hole 922. The second communicating hole 138 is thereby in communication with the main flow channel M1.

Subsequently, an operator, such as an operating surgeon, causes saline solution to be supplied from the water feeding source 200, by operating an operating unit (not illustrated in the drawings), such as a foot switch, while maintaining the state where only the projecting portion 122A has protruded outside the distal end member 92D from the first hole 922 through the first operation on the slider 82. The saline solution supplied from the water feeding source 200 is thereby discharged from a distal end of the knife 12A after following a flow channel through the second communicating hole 138, the first communicating hole 137, and the knife hole 123A, from the main flow channel M1, as indicated by arrows in FIG. 32. The discharged saline solution is injected below a target site T1 by the force of the current of the saline solution. The target site T1 then floats up from other tissue, such as a submucosal layer below the target site T1.

A marking process and an incision process are similar to those of the first embodiment described above, and description thereof will thus be omitted.

Furthermore, when performing irrigation of the surgical site in the processes of the ESD, an operator, such as an operating surgeon, performs the following operation.

The operator, such as an operating surgeon, sets a state where the knife 12A has protruded from a distal end of the sheath 9D by the maximum protruding length, by performing a second operation on the slider 82. In this state, the proximal end of the connector 13D is separated from the ring portion 9216, as illustrated in FIG. 33. The first hole 922 communicates with the main flow channel M1 via the pair of third communicating holes 139. By contrast, the second communicating hole 138 is positioned at the position opposite to the inner surface of the first hole 922. In this state, the inner surface of the first hole 922 is in contact with the outer peripheral surface (a peripheral edge portion of an opening) of the connector 13D, and a flow channel between the second communicating hole 138 and the main flow channel M1 is thereby blocked by the inner peripheral surface of the first hole 922, as indicated by the marks, "x", in FIG. 33. That is, the inner surface of the first hole 922 corresponds to a first closing portion, the first closing portion being arranged in the sheath 9D and being capable of closing the opening of the incision portion 11D, the opening being near the proximal end of the incision portion 11D.

Subsequently, an operator, such as an operating surgeon, causes saline solution to be supplied from the water feeding source 200 by operating an operating unit (not illustrated in the drawings), such as a foot switch, while maintaining the state where the knife 12A has protruded from the distal end of the sheath 9D by the maximum protruding length through the second operation on the slider 82. The saline solution supplied from the water feeding source 200 is thereby discharged from the distal end of the sheath 9D after following a flow channel through the third communicating holes 139 and the first hole 922, from the main flow channel M1, as indicated by arrows in FIG. 33. An opening between an inner peripheral surface of the first hole 922 and an outer peripheral surface of the knife main body 121 has an area larger than that of an opening of the knife hole 123A. Therefore, the surgical site is irrigated with the saline solution discharged from the distal end of the sheath 9D (the distal end member 92D).

As described above, in this fifth embodiment, similarly to the above described first embodiment, the main flow channel M1 is capable of communicating with each of the first hole 922 and the second hole 120D, near the distal end of the sheath 9D (the distal end member 92D). Furthermore, in this configuration, switching between a first mode and a second mode is enabled by advancement and retraction of the incision portion 11D according to operations on the slider 82 by an operator, such as an operating surgeon. The first mode is set by movement of the incision portion 11D toward the distal end of the sheath 9D and is a mode where saline solution is passed to flow into a body cavity by the main flow channel M1 and the first hole 922 communicating with each other. More specifically, the first mode is a state where the main flow channel M1 and the first hole 922 are in communication with each other and the opening of the incision portion 11D is closed by the inner surface of the first hole 922, the opening being near the proximal end of the incision portion 11D. The second mode is set by movement of the incision portion 11D toward a proximal end of the sheath 9D and is a mode where saline solution is passed to flow into the body cavity by the main flow channel M1 and the second hole 120D communicating with each other. More specifically, the second mode is a state where the main flow channel M1 and the second hole 120D are in communication with each other and the opening of the first hole 922 is closed by the connector 13D, the opening being near the proximal end of the first hole 922.

In a case where the treatment tool insertion portion 7D according to the fifth embodiment described above is adopted also, effects similar to those of the above described first embodiment are achieved.

Sixth Embodiment

A sixth embodiment will be described next.

In the following description, any component that is the same as that of the above described first embodiment will be assigned with the same reference sign, and detailed description thereof will be omitted or simplified.

The distal end portion of the treatment tool insertion portion 7 in the endoscope treatment tool 6, described above with respect to the first embodiment, is differently configured in an endoscope treatment tool 6, according to the sixth embodiment. For convenience of explanation, a treatment tool insertion portion according to the sixth embodiment will hereinafter be referred to as a treatment tool insertion portion 7E.

Figure 34:
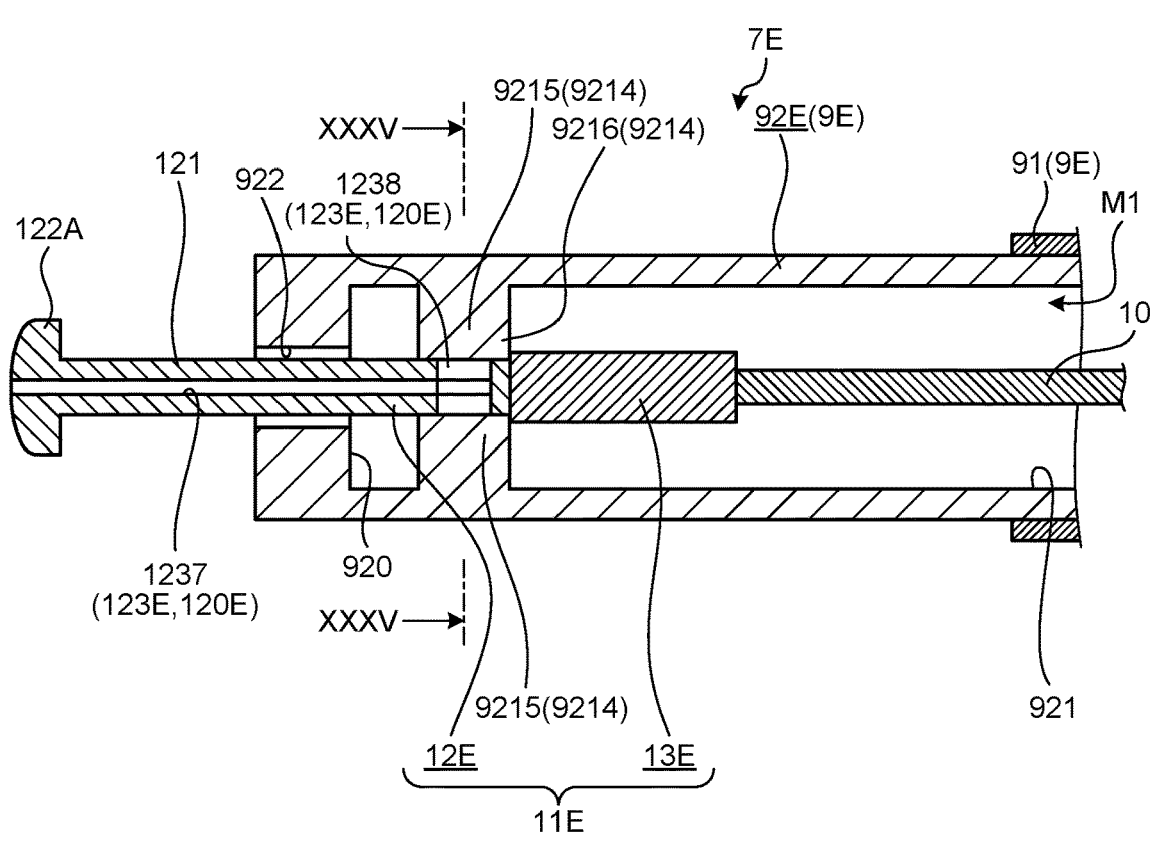
FIG. 34 is a diagram illustrating a configuration of a treatment tool insertion portion according to a sixth embodiment.
Figure 35:
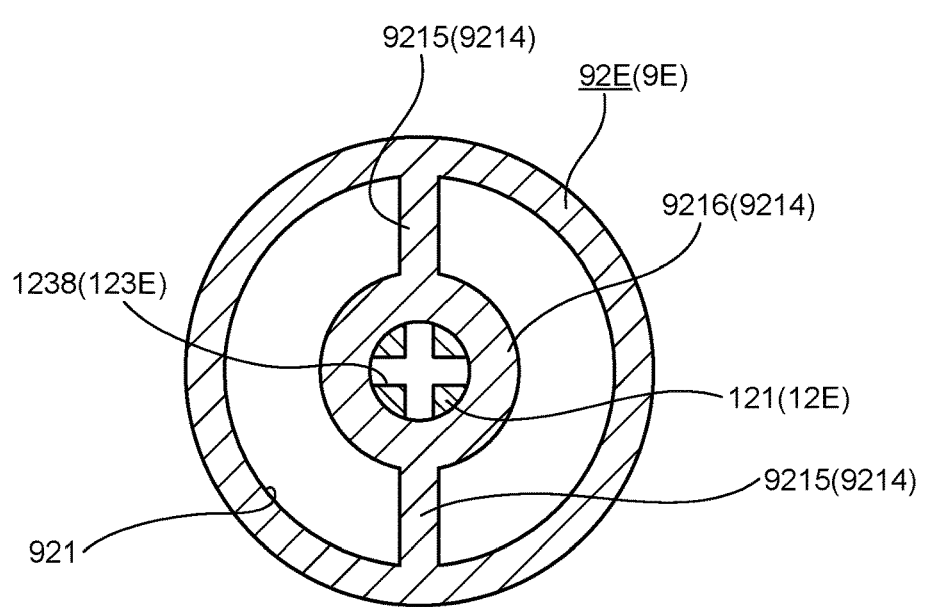
FIG. 35 is a diagram illustrating the configuration of the treatment tool insertion portion according to the sixth embodiment.

FIG. 34 and FIG. 35 are diagrams illustrating a configuration of the treatment tool insertion portion 7E according to the sixth embodiment. Specifically, FIG. 34 is a sectional view corresponding to FIG. 2. FIG. 35 is a sectional view of the treatment tool insertion portion 7E at a position of a line XXXV-XXXV illustrated in FIG. 34.

The sheath 9 and the incision portion 11 of the treatment tool insertion portion 7 described above with respect to the first embodiment are differently configured in the treatment tool insertion portion 7E, as illustrated in FIG. 34 and FIG. 35. For convenience of explanation, a sheath and an incision portion according to the sixth embodiment will hereinafter be referred to as a sheath 9E and an incision portion 11E, respectively.

As illustrated in FIG. 34 and FIG. 35, the distal end member 92 of the sheath 9 described above with respect to the first embodiment is differently configured in the sheath 9E. For convenience of explanation, a distal end member according to the sixth embodiment will hereinafter be referred to as a distal end member 92E.

The distal end member 92E may be formed of a single part or may be formed of a combination of plural parts.

As illustrated in FIG. 34 and FIG. 35, the third wall portion 9214 described above with respect to the second embodiment is provided in the distal end member 92E, instead of the first and second wall portions 9211 and 9212 in the distal end member 92 described above with respect to the first embodiment.

As illustrated in FIG. 34 and FIG. 35, the knife 12 and the connector 13 of the incision portion 11 described above with respect to the first embodiment are differently configured in the incision portion 11E. For convenience of explanation, a knife and a connector according to the sixth embodiment will hereinafter be referred to as a knife 12E and a connector 13E, respectively.

As illustrated in FIG. 34, the knife 12E has an outer shape that is the same as that of the knife 12A described above with respect to the second embodiment. That is, the knife 12E includes a knife main body 121 and a projecting portion 122A. In this sixth embodiment, the dimension of the outer diameter of the knife main body 121 is set slightly smaller than the dimension of the inner diameter of a ring portion 9216. The knife main body 121 is inserted in the ring portion 9216.

Furthermore, as illustrated in FIG. 34, the knife hole 123A in the knife 12A described above with respect to the second embodiment is differently shaped in the knife 12E. For convenience of explanation, a knife hole according to the sixth embodiment will hereinafter be referred to as a knife hole 123E.

The knife hole 123E includes a second hole main body 1237 (FIG. 34) and a communicating hole 1238 (FIG. 34 and FIG. 35).

The second hole main body 1237 extends linearly along a central axis of the knife main body 121 from a distal end face of the projecting portion 122A in a proximal direction, as illustrated in FIG. 34. The second hole main body 1237 may preferably be positioned on the central axis of the knife main body 121.

As illustrated in FIG. 34 and FIG. 35, the communicating hole 1238 is a cross-shaped hole that communicates with a proximal end portion of the second hole main body 1237 and is open on an outer peripheral surface of the knife main body 121.

The knife hole 123E described above is open on an outer peripheral surface of the incision portion 11E, the outer peripheral surface being near a proximal end of the incision portion 11E, and corresponds to a second hole 120E (FIG. 34).

The connector 13E is positioned on a central axis of the distal end member 92E and is formed of a cylindrical member extending linearly along the central axis. The dimension of the outer diameter of the connector 13E is set larger than the dimension of the inner diameter of the ring portion 9216.

Operation of an endoscope treatment tool 6, according to the sixth embodiment, will be described next. For convenience of explanation, a flow of ESD will hereinafter be described as an example, similarly to the above described first embodiment.

Figure 36:
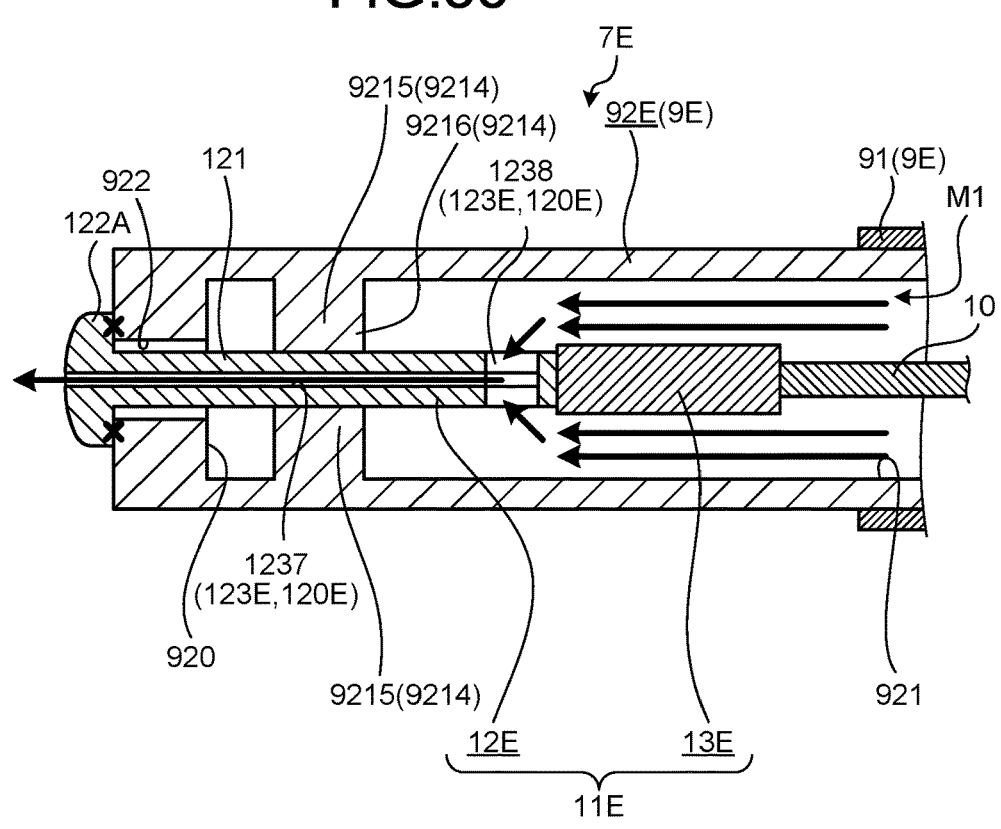
FIG. 36 is a diagram illustrating operation of an endoscope treatment tool.
Figure 37:
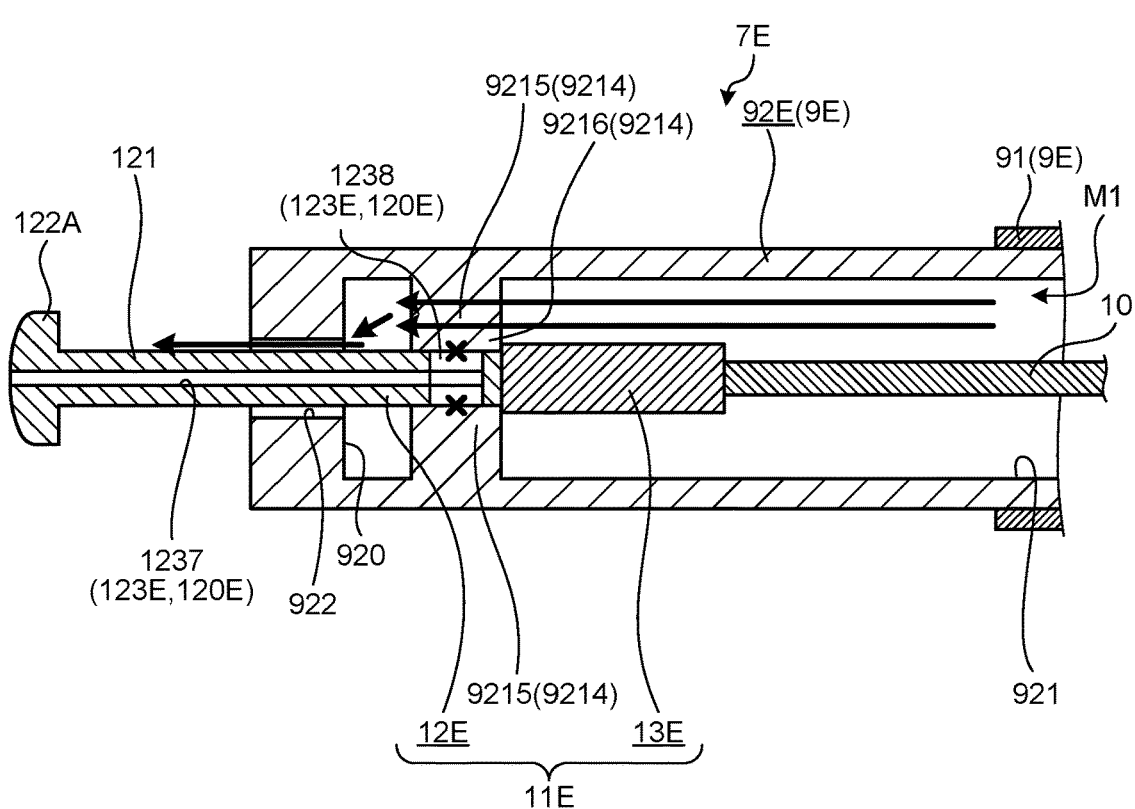
FIG. 37 is a diagram illustrating operation of the endoscope treatment tool.

FIG. 36 and FIG. 37 are diagrams illustrating the operation of the endoscope treatment tool 6. Specifically, FIG. 36 and FIG. 37 are sectional views corresponding to FIG. 34.

In this sixth embodiment, an operator, such as an operating surgeon, performs a local injection process as described below.

That is, the operator, such as an operating surgeon, sets a state where only the projecting portion 122A has protruded outside the distal end member 92E from a first hole 922, by performing a first operation on the slider 82. In this state, the communicating hole 1238 is positioned at a position displaced from an inner peripheral surface of the ring portion 9216, as illustrated in FIG. 36. The communicating hole 1238 is thereby in communication with a main flow channel M1. By contrast, as indicated by the marks, "x", in FIG. 36, the projecting portion 122A comes into contact with a distal end of the sheath 9E (the distal end member 92E) and the first hole 922 is thus closed near a distal end of the first hole 922 by the projecting portion 122A. That is, the projecting portion 122A corresponds to a second closing portion, the second closing portion enabling an opening of the first hole 922 to be closed, the opening being near the distal end of the first hole 922.

Subsequently, an operator, such as an operating surgeon, causes saline solution to be supplied from the water feeding source 200 by operating an operating unit (not illustrated in the drawings), such as a foot switch, while maintaining the state where only the projecting portion 122A has protruded outside the distal end member 92E from the first hole 922 through the first operation on the slider 82, that is, a state where the projecting portion 122A has protruded from the first hole 922 and the knife main body 121 has been positioned in the first hole 922. The saline solution supplied from the water feeding source 200 is thereby discharged from a distal end of the knife 12E after following a flow channel through the communicating hole 1238 and the second hole main body 1237, from the main flow channel M1, as indicted by arrows in FIG. 36. The discharged saline solution is injected below a target site T1 by the force of the current of the saline solution. The target site T1 then floats up from other tissue, such as a submucosal layer below the target site T1.

A marking process and an incision process are similar to those of the first embodiment described above, and description thereof will thus be omitted.

Furthermore, when performing irrigation of the surgical site in the processes of the ESD, an operator, such as an operating surgeon, performs the following operation.

The operator, such as an operating surgeon, sets a state where the knife 12E has protruded from the distal end of the sheath 9E by the maximum protruding length, by performing a second operation on the slider 82. In this state, a distal end of the connector 13E is in contact with a proximal end face of the ring portion 9216. Furthermore, as illustrated in FIG. 37, the communicating hole 1238 is positioned at a position opposite to the inner peripheral surface of the ring portion 9216. In this state, the inner peripheral surface of the ring portion 9216 is in contact with the outer peripheral surface (a peripheral edge portion of an opening) of the knife main body 121, and a flow channel between the communicating hole 1238 and the main flow channel M1 is thereby blocked by the ring portion 9216 as indicated by the marks, "x", in FIG. 37. That is, the ring portion 9216 corresponds to a first closing portion, the first closing portion being arranged in the sheath 9E and enabling an opening of the incision portion 11E to be closed, the opening being near the proximal end of the incision portion 11E. By contrast, the first hole 922 is released from the closure near the distal end of the first hole 922 by the projecting portion 122A.

Subsequently, an operator, such as an operating surgeon, causes saline solution to be supplied from the water feeding source 200 by operating an operating unit (not illustrated in the drawings), such as a foot switch, while maintaining the state where the knife 12E has protruded from the distal end of the sheath 9E by the maximum protruding length through the second operation on the slider 82. The saline solution supplied from the water feeding source 200 is thereby discharged from the distal end of the sheath 9E and supplied to the surgical site, after following a flow channel through the first hole 922 from the main flow channel M1, as indicated by arrows in FIG. 37. An opening between an inner peripheral surface of the first hole 922 and the outer peripheral surface of the knife main body 121 has an area larger than that of an opening of the second hole main body 1237. Therefore, the surgical site is irrigated with the saline solution discharged from the distal end of the sheath 9E (the distal end member 92E).

As described above, in this sixth embodiment, similarly to the above described first embodiment, the main flow channel M1 is capable of communicating with each of the first hole 922 and the second hole 120E, near the distal end of the sheath 9E (the distal end member 92E). Furthermore, in this configuration, switching between a first mode and a second mode is enabled by advancement and retraction of the incision portion 11E according to operations on the slider 82 by an operator, such as an operating surgeon. The first mode is set by movement of the incision portion 11E toward a proximal end of the sheath 9E and is a mode where saline solution is passed to flow into a body cavity by the main flow channel M1 and the first hole 922 communicating with each other. More specifically, the first mode is a state where the main flow channel M1 and the first hole 922 are in communication with each other and the opening of the incision portion 11E is closed by the ring portion 9216, the opening being near the proximal end of the incision portion 11E. The second mode is set by movement of the incision portion 11E toward the proximal end of the sheath 9E and is a mode where saline solution is passed to flow into the body cavity by the main flow channel M1 and the second hole 120E communicating with each other. More specifically, the second mode is a state where the main flow channel M1 and the second hole 120E are in communication with each other and the opening of the first hole 922 is closed by the projecting portion 122A, the opening being near the distal end of the first hole 922.

In a case where the treatment tool insertion portion 7E according to the sixth embodiment described above is adopted also, effects similar to those of the above described first embodiment are achieved.

Seventh Embodiment

A seventh embodiment will be described next.

In the following description, any component that is the same as that of the above described first embodiment will be assigned with the same reference sign, and detailed description thereof will be omitted or simplified.

The distal end portion of the treatment tool insertion portion 7 in the endoscope treatment tool 6, described above with respect to the first embodiment, is differently configured in an endoscope treatment tool 6, according to the seventh embodiment. For convenience of explanation, a treatment tool insertion portion according to the seventh embodiment will hereinafter be referred to as a treatment tool insertion portion 7F.

Figure 38:
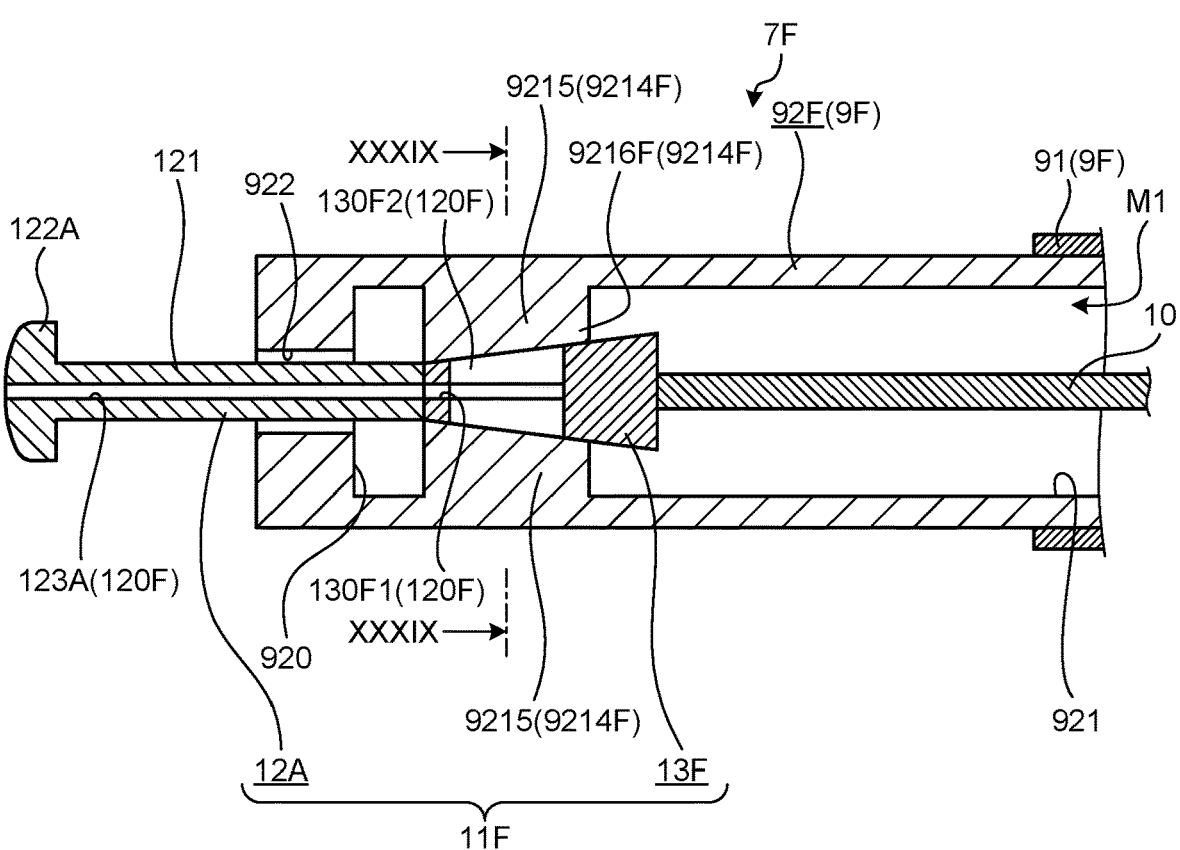
FIG. 38 is a diagram illustrating a configuration of a treatment tool insertion portion according to a seventh embodiment.
Figure 39:
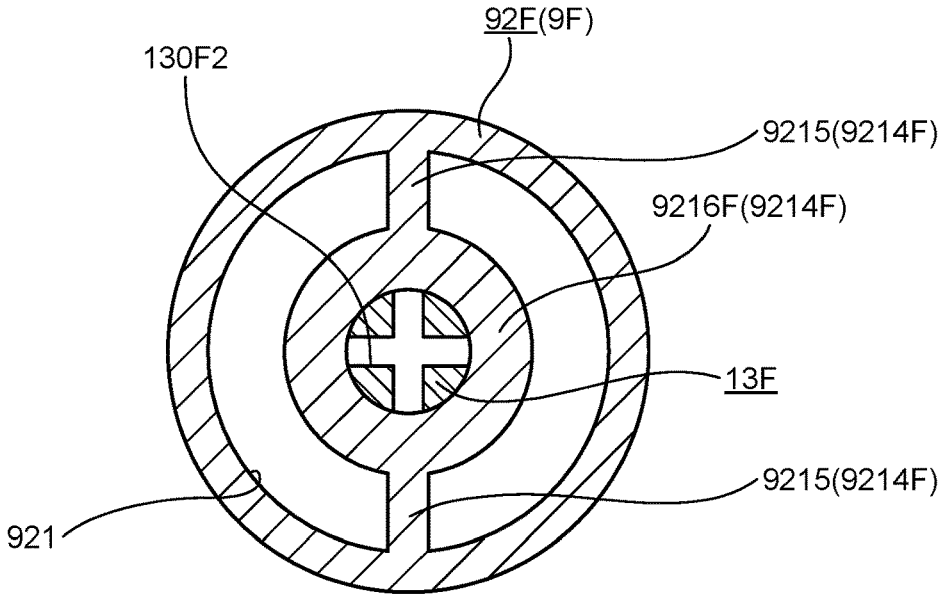
FIG. 39 is a diagram illustrating the configuration of the treatment tool insertion portion according to the seventh embodiment.

FIG. 38 and FIG. 39 are diagrams illustrating a configuration of the treatment tool insertion portion 7F according to the seventh embodiment. Specifically, FIG. 38 is a sectional view corresponding to FIG. 2. FIG. 39 is a sectional view of the treatment tool insertion portion 7F at a position of a line XXXIX-XXXIX illustrated in FIG. 38.

The sheath 9 and the incision portion 11 of the treatment tool insertion portion 7 described above with respect to the first embodiment are differently configured in the treatment tool insertion portion 7F, as illustrated in FIG. 38 and FIG. 39. For convenience of explanation, a sheath and an incision portion according to the seventh embodiment will hereinafter be referred to as a sheath 9F and an incision portion 11F, respectively.

As illustrated in FIG. 38 and FIG. 39, the distal end member 92 of the sheath 9 described above with respect to the first embodiment is differently configured in the sheath 9F. For convenience of explanation, a distal end member according to the seventh embodiment will hereinafter be referred to as a distal end member 92F.

The distal end member 92F may be formed of a single part or may be formed of a combination of plural parts.

As illustrated in FIG. 38 and FIG. 39, a third wall portion 9214F that is approximately the same as the third wall portion 9214 described above with respect to the second embodiment is provided in the distal end member 92F, instead of the first and second wall portions 9211 and 9212 in the distal end member 92 described above with respect to the first embodiment.

The inner peripheral surface of the ring portion 9216 of the third wall portion 9214 described above with respect to the second embodiment is differently shaped in the third wall portion 9214, as illustrated in FIG. 38 and FIG. 39. For convenience of explanation, a ring portion according to the seventh embodiment will hereinafter be referred to as a ring portion 9216F.

An inner peripheral surface of the ring portion 9216F has a truncated cone shape that decreases in inner diameter toward a distal end thereof, as illustrated in FIG. 38 and FIG. 39.

As illustrated in FIG. 38 to FIG. 39, the knife 12A described above with respect to the second embodiment is adopted in the incision portion 11F, instead of the knife 12 in the incision portion 11 described above with respect to the first embodiment, and the connector 13 in the incision portion 11 is also shaped differently in the incision portion 11F. For convenience of explanation, a connector according to the seventh embodiment will hereinafter be referred to as a connector 13F.

The connector 13F extends along a central axis of the distal end member 92F and has a truncated cone shape that is approximately the same as that of the inner peripheral surface of the ring portion 9216F. Furthermore, first and second communicating holes 130F1 and 130F2 are provided in the connector 13F, as illustrated in FIG. 38 and FIG. 39. The connector 13F may preferably be positioned on the central axis of the distal end member 92F.

The first communicating hole 130F1 extends linearly along a central axis of the connector 13F from a distal end to a proximal end of the connector 13F, as illustrated in FIG. 38. In a state where the connector 13F and a knife main body 121 have been connected to each other, the first communicating hole 130F1 is in communication with a knife hole 123A. The first communicating hole 130F1 may preferably be positioned on the central axis of the connector 13F.

As illustrated in FIG. 38 and FIG. 39, the second communicating hole 130F2 is a cross-shaped hole that is positioned at an approximately central portion of the longitudinal length of the connector 13F, communicates with the first communicating hole 130F1, and is open on an outer peripheral surface of the connector 13F.

The knife hole 123A and first and second communicating holes 130F1 and 130F2 described above are open on an outer peripheral surface of the incision portion 11F, the outer peripheral surface being close to a proximal end of the incision portion 11F, and correspond to a second hole 120F (FIG. 38).

Operation of an endoscope treatment tool 6, according to the seventh embodiment, will be described next. For convenience of explanation, a flow of ESD will hereinafter be described as an example, similarly to the above described first embodiment.

Figure 40:
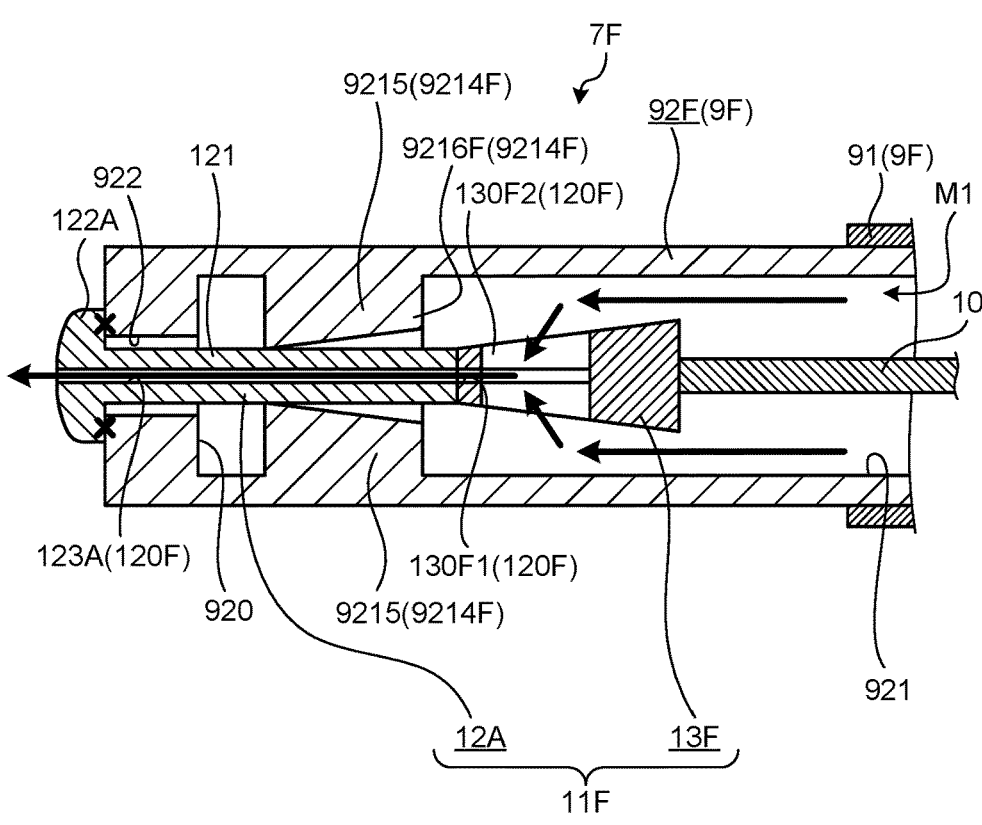
FIG. 40 is a diagram illustrating operation of an endoscope treatment tool.
Figure 41:
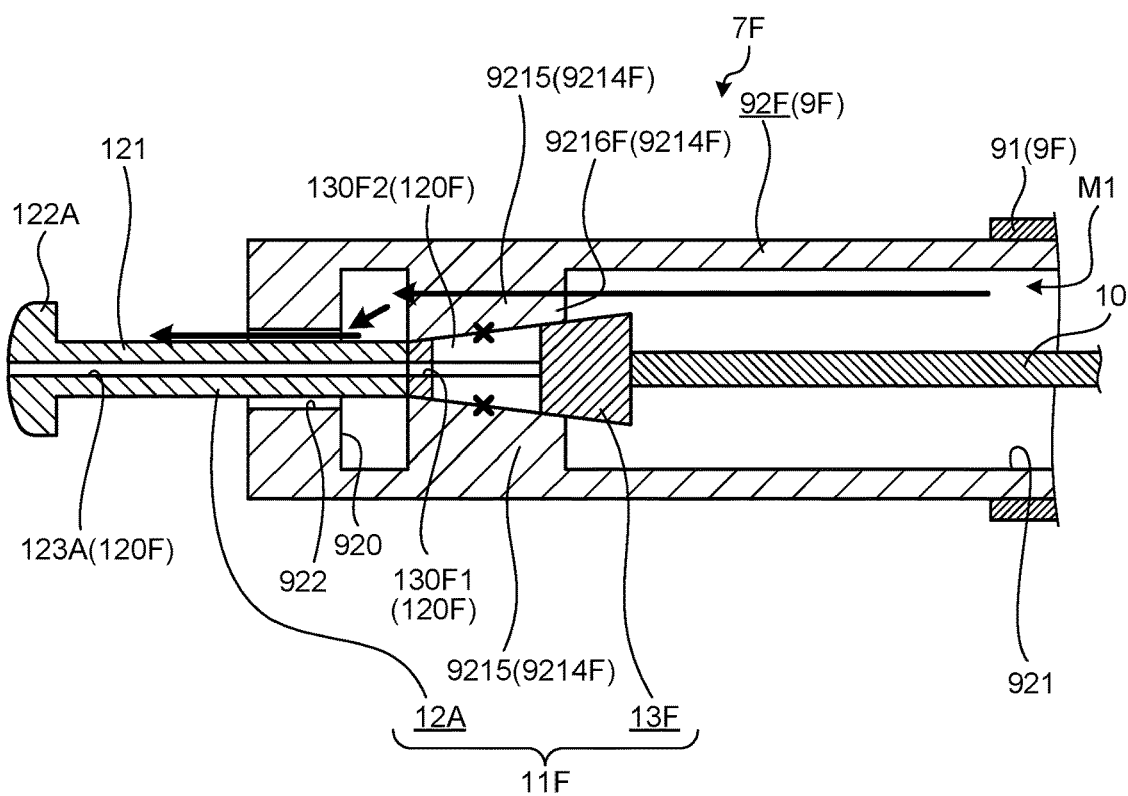
FIG. 41 is a diagram illustrating operation of the endoscope treatment tool.

FIG. 40 and FIG. 41 are diagrams illustrating the operation of the endoscope treatment tool 6. Specifically, FIG. 40 and FIG. 41 are sectional views corresponding to FIG. 38.

In this seventh embodiment, an operator, such as an operating surgeon, performs a local injection process as described below.

That is, the operator, such as an operating surgeon, sets a state where only a projecting portion 122A has protruded outside the distal end member 92F from a first hole 922, by performing a first operation on the slider 82. In this state, the connector 13F is positioned at a position separated in a proximal direction from the inner peripheral surface of the ring portion 9216F, as illustrated in FIG. 40. The second communicating hole 130F2 is thereby in communication with a main flow channel M1. By contrast, as indicated by the marks, "x", in FIG. 40, the projecting portion 122A is in contact with a distal end of the sheath 9F (the distal end member 92F) and the first hole 922 is thus closed near a distal end of the first hole 922 by the projecting portion 122A. That is, the projecting portion 122A corresponds to a second closing portion, the second closing portion enabling an opening of the first hole 922 to be closed, the opening being near the distal end of the first hole 922.

Subsequently, an operator, such as an operating surgeon, causes saline solution to be supplied from the water feeding source 200, by operating an operating unit (not illustrated in the drawings), such as a foot switch, while maintaining the state where only the projecting portion 122A has protruded outside the distal end member 92F from the first hole 922 through the first operation on the slider 82. The saline solution supplied from the water feeding source 200 is thereby discharged from a distal end of the knife 12A after following a flow channel through the second communicating hole 130F2, the first communicating hole 130F1, and the knife hole 123A, from the main flow channel M1, as indicated by arrows in FIG. 40. The discharged saline solution is injected below a target site T1 by the force of the current of the saline solution. The target site T1 then floats up from other tissue, such as a submucosal layer below the target site T1.

A marking process and an incision process are similar to those of the first embodiment described above, and description thereof will thus be omitted.

Furthermore, when performing irrigation of the surgical site in the processes of the ESD, an operator, such as an operating surgeon, performs the following operation.

The operator, such as an operating surgeon, sets a state where the knife 12A has protruded from the distal end of the sheath 9F by the maximum protruding length, by performing a second operation on the slider 82. In this state, as illustrated in FIG. 41, the connector 13F is in contact with the inner peripheral surface of the ring portion 9216F. In this state, the inner peripheral surface of the ring portion 9216F is in contact with the outer peripheral surface (a peripheral edge portion of an opening) of the connector 13F, and a flow channel between the second communicating hole 130F2 and the main flow channel M1 is blocked by the ring portion 9216F as indicated by the marks, "x", in FIG. 41. That is, the ring portion 9216F corresponds to a first closing portion, the first closing portion being arranged in the sheath 9F and enabling the opening of the incision portion 11F to be closed, the opening being near the proximal end of the incision portion 11F. By contrast, the first hole 922 is released from the closure near the distal end of the first hole 922 by the projecting portion 122A.

Subsequently, an operator, such as an operating surgeon, causes saline solution to be supplied from the water feeding source 200 by operating an operating unit (not illustrated in the drawings), such as a foot switch, while maintaining the state where the knife 12A has protruded from the distal end of the sheath 9F by the maximum protruding length through the second operation on the slider 82. The saline solution supplied from the water feeding source 200 is thereby discharged from the distal end of the sheath 9F and supplied to the surgical site, after following a flow channel through the first hole 922 from the main flow channel M1, as indicated by arrows in FIG. 41. An opening between an inner peripheral surface of the first hole 922 and an outer peripheral surface of the knife main body 121 has an area larger than that of an opening of the knife hole 123A. Therefore, the surgical site is irrigated with the saline solution discharged from the distal end of the sheath 9F (the distal end member 92F).

As described above, in this seventh embodiment, similarly to the above described first embodiment, the main flow channel M1 is capable of communicating with each of the first hole 922 and the second hole 120F, near the distal end of the sheath 9F (the distal end member 92F). Furthermore, in this configuration, switching between a first mode and a second mode is enabled by advancement and retraction of the incision portion 11F according to operations on the slider 82 by an operator, such as an operating surgeon. The first mode is set by movement of the incision portion 11F toward the distal end of the sheath 9F and is a mode where saline solution is passed to flow into a body cavity by the main flow channel M1 and the first hole 922 communicating with each other. More specifically, the first mode is a state where the main flow channel M1 and the first hole 922 are in communication with each other and the opening of the incision portion 11F is closed by the ring portion 9216F, the opening being near the proximal end of the incision portion 11F. The second mode is set by movement of the incision portion 11F toward a proximal end of the sheath 9F and is a mode where saline solution is passed to flow into the body cavity by the main flow channel M1 and the second hole 120F communicating with each other. More specifically, the second mode is a state where the main flow channel M1 and the second hole 120F are in communication with each other and the opening of the first hole 922 is closed by the projecting portion 122A, the opening being near the distal end of the first hole 922.

In a case where the treatment tool insertion portion 7F according to the seventh embodiment described above is adopted also, effects similar to those of the above described first embodiment are achieved.

In particular, the inner peripheral surface of the ring portion 9216 and the connector 13F have the truncated cone shapes and saline solution is thus prevented from leaking into the second hole 120F in the first mode.

Eighth Embodiment

An eighth embodiment will be described next.

In the following description, any component that is the same as that of the above described first embodiment will be assigned with the same reference sign, and detailed description thereof will be omitted or simplified.

The distal end portion of the treatment tool insertion portion 7 in the endoscope treatment tool 6, described above with respect to the first embodiment, is differently configured in an endoscope treatment tool 6, according to the eighth embodiment. For convenience of explanation, a treatment tool insertion portion according to the eighth embodiment will hereinafter be referred to as a treatment tool insertion portion 7G.

Figure 42:
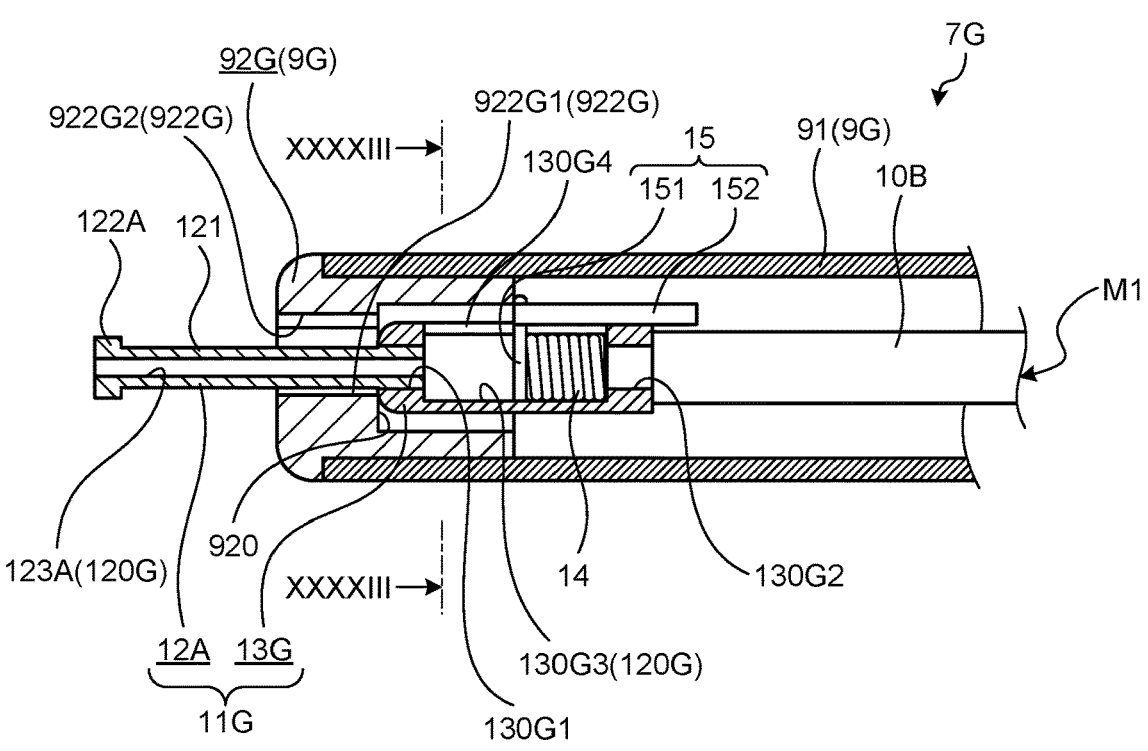
FIG. 42 is a diagram illustrating a configuration of a treatment tool insertion portion according to an eighth embodiment.
Figure 43:
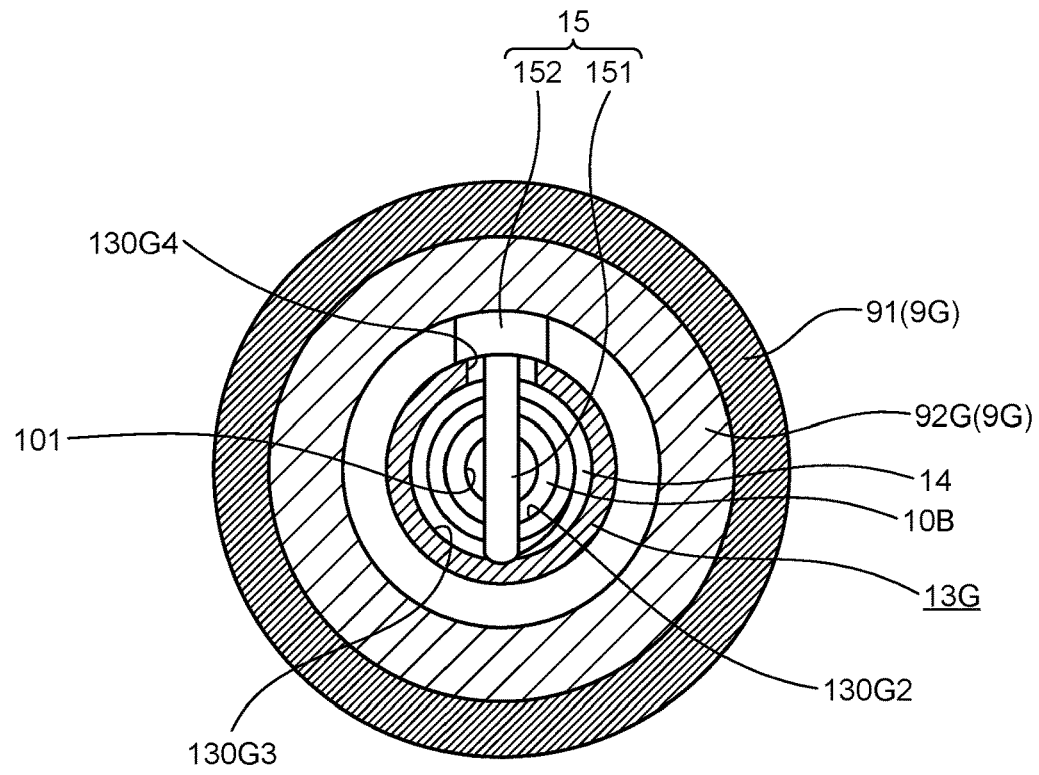
FIG. 43 is a diagram illustrating the configuration of the treatment tool insertion portion according to the eighth embodiment.

FIG. 42 and FIG. 43 are diagrams illustrating a configuration of the treatment tool insertion portion 7G according to the eighth embodiment. Specifically, FIG. 42 is a sectional view corresponding to FIG. 2. FIG. 43 is a sectional view of the treatment tool insertion portion 7G at a position of a line XXXXIII-XXXXIII illustrated in FIG. 42.

As illustrated in FIG. 42 and FIG. 43, the wire 10B described above with respect to the third embodiment is adopted in the treatment tool insertion portion 7G, instead of the wire 10 in the treatment tool insertion portion 7 described above with respect to the first embodiment, and the sheath 9 and the incision portion 11 in the treatment tool insertion portion 7 are also differently configured in the treatment tool insertion portion 7G. For convenience of explanation, a sheath and an incision portion according to the eighth embodiment will hereinafter be referred to as a sheath 9G and an incision portion 11G, respectively.

As illustrated in FIG. 42 and FIG. 43, the distal end member 92 of the sheath 9 described above with respect to the first embodiment is differently shaped in the sheath 9G. For convenience of explanation, a distal end member according to the eighth embodiment will hereinafter be referred to as a distal end member 92G.

The distal end member 92G may be formed of a single part or may be formed of a combination of plural parts.

As illustrated in FIG. 42, the first and second wall portions 9211 and 9212 of the distal end member 92 described above with respect to the first embodiment are omitted from the distal end member 92G.

Furthermore, as illustrated in FIG. 42, the first hole 922 in the distal end member 92 described above with respect to the first embodiment is differently shaped in the distal end member 92G. For convenience of explanation, a first hole according to the eighth embodiment will hereinafter be referred to as a first hole 922G.

The first hole 922G includes a hole main body 922G1 and an auxiliary hole 922G2, as illustrated in FIG. 42.

The hole main body 922G1 has a circular cross-section and extends linearly along a central axis of the distal end member 92G. The dimension of the inner diameter of the hole main body 922G1 is set smaller than the dimension of the outer diameter of a projecting portion 122A and larger than the dimension of the outer diameter of a knife main body 121. The hole main body 922G1 may preferably be positioned on the central axis of the distal end member 92G.

As illustrated in FIG. 42, the auxiliary hole 922G2 is a portion extending in a radial direction from a part of the hole main body 922G1, and extends linearly along the central axis of the distal end member 92G, similarly to the hole main body 922G1.

As illustrated in FIG. 42 and FIG. 43, the knife 12A described above with respect to the second embodiment is adopted in the incision portion 11G, instead of the knife 12 in the incision portion 11 described above with respect to the first embodiment, and the connector 13 in the incision portion 11 is also shaped differently in the incision portion 11G. For convenience of explanation, a connector according to the eighth embodiment will hereinafter be referred to as a connector 13G.

The connector 13G is formed of a cylindrical member extending linearly along the central axis of the distal end member 92G. The dimension of the outer diameter of the connector 13G is set larger than the dimension of the inner diameter of the hole main body 922G1 and smaller than the dimension of the inner diameter of the distal end member 92G. Furthermore, as illustrated in FIG. 42 and FIG. 43, first and second fitting holes 130G1 and 130G2, a receiving hole 130G3, and a communicating hole 130G4 are provided in the connector 13G. The connector 13G may preferably be positioned on the central axis of the distal end member 92G.

The first fitting hole 130G1 is a circular hole extending linearly along a central axis of the connector 13G from a distal end of the connector 13G toward a proximal end of the connector 13G. The knife main body 121 is fixed in a state of being inserted in the first fitting hole 130G1. The first fitting hole 130G1 may preferably be positioned on the central axis of the connector 13G.

The second fitting hole 130G2 is a circular hole extending linearly along the central axis of the connector 13G from the proximal end of the connector 13G toward the distal end of the connector 13G. The wire 10B is fixed in a state of being inserted in the second fitting hole 130G2. The second fitting hole 130G2 may preferably be positioned on the central axis of the connector 13G.

The receiving hole 130G3 is a circular hole extending linearly along the central axis of the connector 13G from near the distal end of the connector 13G toward the proximal end of the connector 13G, and communicates with the first and second fitting holes 130G1 and 130G2. The dimension of the inner diameter of the receiving hole 130G3 is set larger than the dimensions of the inner diameters of the first and second fitting holes 130G1 and 130G2. In a state where the knife 12A and the wire 10B have been connected to each other by the connector 13G, a main flow channel M1 is in communication with a knife hole 123A via the receiving hole 130G3. That is, the knife hole 123A and the receiving hole 130G3 correspond to a second hole 120G (FIG. 42). The receiving hole 130G3 may preferably be positioned on the central axis of the connector 13G.

The communicating hole 130G4 is an elongated hole penetrating the connector 13G from an outer peripheral surface of the connector 13G to the receiving hole 130G3 and extending along a longitudinal axis of the connector 13G.

In this eighth embodiment, a biasing member 14 and a flow channel switching member 15 are attached to the above described connector 13G, as illustrated in FIG. 42 and FIG. 43.

As illustrated in FIG. 42 and FIG. 43, the biasing member 14 is formed of a coil spring and arranged in the receiving hole 130G3. One end of the biasing member 14 is brought into contact with or fixed to a supporting portion 151 included in the flow channel switching member 15 and the other end of the biasing member 14 is brought into contact with or fixed to a peripheral edge portion of the second fitting hole 130G2. The biasing member 14 biases the flow channel switching member 15 in a distal direction.

The flow channel switching member 15 is a member that switches between flow channels for saline solution passed via the main flow channel M1. This flow channel switching member 15 includes the supporting portion 151 and a closing portion 152, as illustrated in FIG. 42 and FIG. 43.

The supporting portion 151 is inserted in the receiving hole 130G3 through the communicating hole 130G4, is orthogonal to the central axis of the connector 13G, and has a shape of a pin arranged in a posture positioned on the central axis of the connector 13G.

The closing portion 152 is fixed to an end portion of the supporting portion 151, the end portion being positioned outside the connector 13G, and has a plate shape extending along the central axis of the connector 13G. The size of this closing portion 152 is set to enable the communicating hole 130G4 to be closed.

Operation of the endoscope treatment tool 6, according to the eighth embodiment, will be described next. For convenience of explanation, a flow of ESD will hereinafter be described as an example, similarly to the above described first embodiment.

Figure 44:
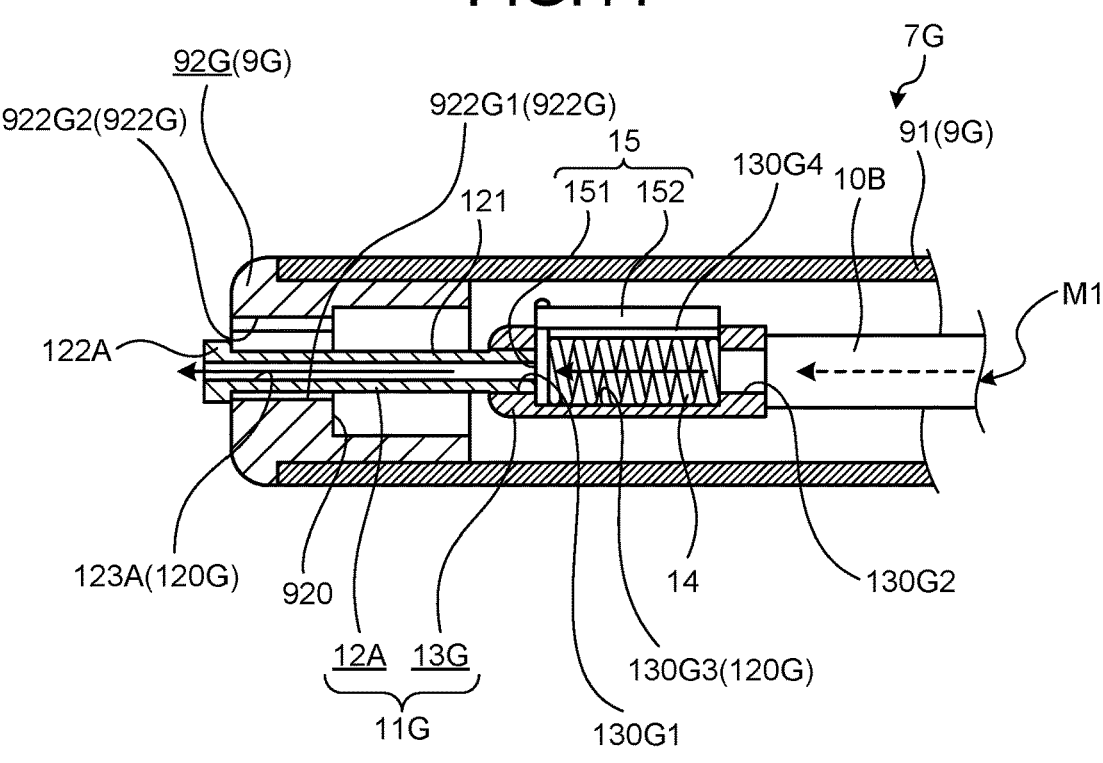
FIG. 44 is a diagram illustrating operation of an endoscope treatment tool.
Figure 45:
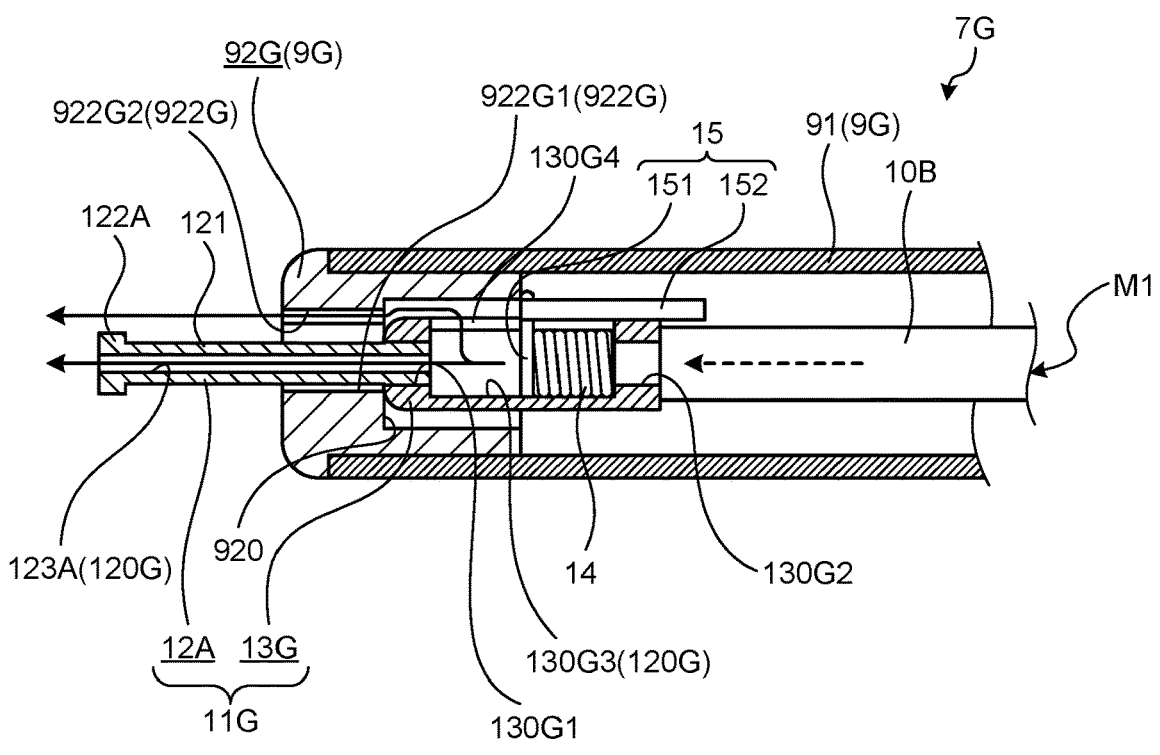
FIG. 45 is a diagram illustrating operation of the endoscope treatment tool.

FIG. 44 and FIG. 45 are diagrams illustrating the operation of the endoscope treatment tool 6. Specifically, FIG. 44 and FIG. 45 are sectional views corresponding to FIG. 42.

In this eighth embodiment, an operator, such as an operating surgeon, performs a local injection process as described below.

That is, the operator, such as an operating surgeon, sets a state where only the projecting portion 122A has protruded outside the distal end member 92G from the first hole 922G, by performing a first operation on the slider 82. In this state, the connector 13G is in a state of being positioned in a proximal direction from the distal end member 92G, as illustrated in FIG. 44. Furthermore, the flow channel switching member 15 moves in the distal direction relatively to the connector 13G, due to biasing force of the biasing member 14. In this state, the closing portion 152 is in contact with the outer peripheral surface (a peripheral edge portion of an opening) of the connector 13G and the communicating hole 130G4 is thereby closed by the closing portion 152.

Subsequently, an operator, such as an operating surgeon, causes saline solution to be supplied from the water feeding source 200, by operating an operating unit (not illustrated in the drawings), such as a foot switch, while maintaining the state where only the projecting portion 122A has protruded outside the distal end member 92G from the first hole 922G through the first operation on the slider 82. The saline solution supplied from the water feeding source 200 is thereby discharged from a distal end of the knife 12A after following a flow channel through the receiving hole 130G3 and the knife hole 123A, from the main flow channel M1, as indicated by arrows in FIG. 44. The discharged saline solution is injected below a target site T1 by the force of the current of the saline solution. The target site T1 then floats up from other tissue, such as a submucosal layer below the target site T1.

A marking process and an incision process are similar to those of the first embodiment described above, and description thereof will thus be omitted.

Furthermore, when performing irrigation of the surgical site in the processes of the ESD, an operator, such as an operating surgeon, performs the following operation.

The operator, such as an operating surgeon, sets a state where the knife 12A has protruded from a distal end of the sheath 9G by the maximum protruding length, by performing a second operation on the slider 82. During the course of the second operation, the connector 13G advances into the distal end member 92G from the proximal direction. By contrast, the flow channel switching member 15 gets caught on a proximal end of the distal end member 92G and moves in the proximal direction relatively to the connector 13G against the biasing force of the biasing member 14. The communicating hole 130G4 is thereby released from the closure by the closing portion 152, as illustrated in FIG. 45.

Subsequently, an operator, such as an operating surgeon, causes saline solution to be supplied from the water feeding source 200 by operating an operating unit (not illustrated in the drawings), such as a foot switch, while maintaining the state where the knife 12A has protruded from the distal end of the sheath 9G by the maximum protruding length through the second operation on the slider 82. The saline solution supplied from the water feeding source 200 is thereby supplied to the surgical site by being: discharged from the distal end of the knife 12A after following the flow channel through the receiving hole 130G3 and the knife hole 123A from the main flow channel M1; and discharged from the distal end of the sheath 9G after following a flow channel through the receiving hole 130G3, the communicating hole 130G4, the distal end member 92G, and the auxiliary hole 922G2, from the main flow channel M1. The saline solution that has followed the main flow channel M1 is thus discharged from both the knife hole 123A and the auxiliary hole 922G2. Therefore, the surgical site is irrigated with the saline solution discharged from both the knife hole 123A and the auxiliary hole 922G2.

As described above, similarly to the above described first embodiment, in this eighth embodiment also, the main flow channel M1 is capable of communicating with each of the first hole 922G and the second hole 120G, near the distal end of the sheath 9G (the distal end member 92G). Furthermore, in this configuration, switching between a first mode and a second mode is enabled by advancement and retraction of the incision portion 11G according to operations on the slider 82 by an operator, such as an operating surgeon. The first mode is a mode where the main flow channel M1 is in communication with the first hole 922G and second hole 120G and saline solution is thereby passed to flow into a body cavity. The second mode is a mode where the main flow channel M1 is in communication with the second hole 120G and the saline solution is thereby passed to flow into the body cavity.

In a case where the treatment tool insertion portion 7G according to the eighth embodiment described above is adopted also, effects similar to those of the above described first embodiment are achieved.

OTHER EMBODIMENTS

Modes for implementing the disclosure have been described thus far, but the disclosure is not to be limited only to the above described first to eighth embodiments.

In the above described first to eighth embodiments, the surgical site is irrigated in the first mode and the local injection process is executed in the second mode, but the disclosure is not limited to these embodiments. For example, the surgical site may be irrigated in both the first and second modes.

In all of the first to eighth embodiments described above, the rotating restricting structure (the second wall portion 9212 (the groove portion 9213) and the rotation restricting portion 132) according to the disclosure may be adopted.

In the above described first to eighth embodiments, the projecting portion 122 (122A) is not limited to the shape described above with respect to the first to eighth embodiments, and any other shape may be adopted.

Figure 46A:
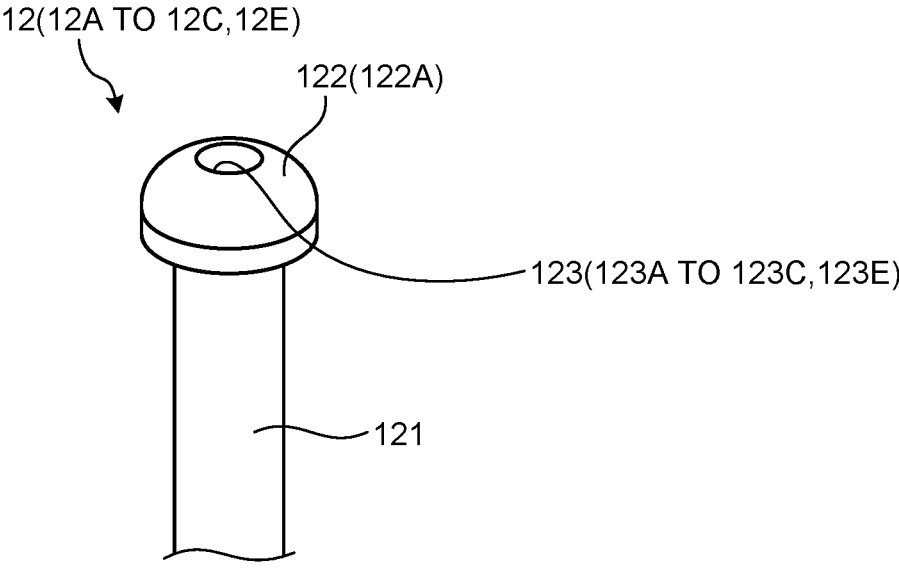
FIG. 46A is a diagram illustrating an example of a shape of a projecting portion.
Figure 46B:
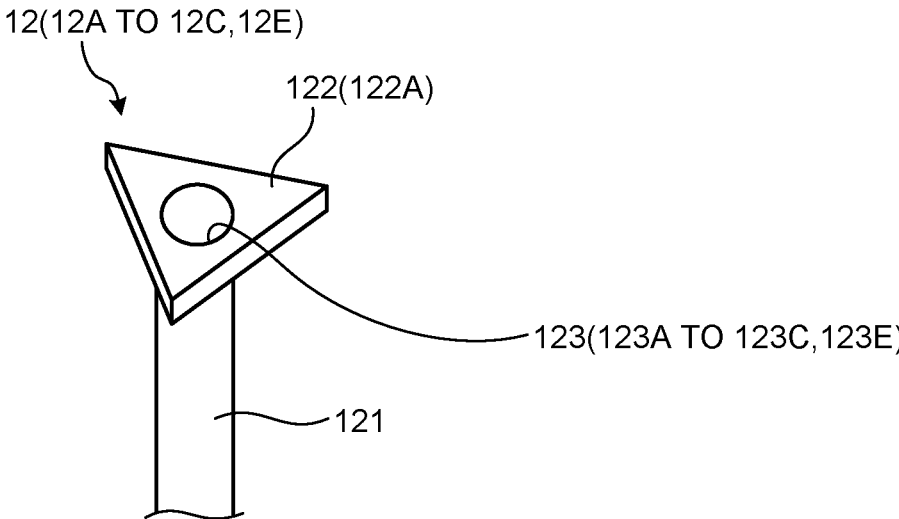
FIG. 46B is a diagram illustrating an example of the shape of the projecting portion.

FIG. 46A and FIG. 46B are diagrams illustrating examples of the shape of the projecting portion 122 (122A).

Specifically, as illustrated in FIG. 46A or FIG. 46B, the projecting portion 122 (122A) may have a flange shape that is, for example, semispherical (FIG. 46A) or triangular (FIG. 46B), or may have a needle shape without being flanged.

An endoscope treatment tool, according to the disclosure, enables improvement of user-friendliness.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope treatment tool comprising:
a sheath including a distal end portion having a first channel, wherein the sheath includes a main flow chamber extending proximally more than the distal end portion; and
an incision device inserted in the first channel, wherein the incision device is translatable in the first channel and wherein the incision device includes a second channel extending along a longitudinal axis of the incision device,
wherein the endoscope treatment tool is switchable between a first mode and a second mode,
wherein the endoscope treatment tool is in the first mode when the incision device is in a first position and the endoscope treatment tool is in the second mode when the incision device is in a second position, and
wherein, in the first mode, the first channel is in fluid communication with the main flow chamber and the second channel is closed off from the main flow chamber, and, in the second mode, the second channel is in fluid communication with the main flow chamber and the first channel is closed off from the main flow chamber.

2. The endoscope treatment tool according to claim 1, further comprising a rotation restricting structure,
wherein the rotation restricting structure is located between the incision device and the sheath and is configured to restrict rotation of the incision device about a central axis of the incision device.

3. The endoscope treatment tool according to claim 2, wherein the rotation restricting structure includes a groove provided in the sheath and a protrusion provided in the incision device.

4. The endoscope treatment tool according to claim 3, wherein the protrusion extends longitudinally along an outer surface of the incision device, and
wherein the protrusion is positioned in the groove.

5. The endoscope treatment tool according to claim 1, wherein the second position of the incision device is distal of the first position of the incision device.

6. The endoscope treatment tool according to claim 5, wherein an opening of the second channel defines a first opening,
wherein the first opening opens in an outer peripheral surface of the incision device, and
wherein, in the first mode, a portion of the sheath closes the first opening.

7. The endoscope treatment tool according to claim 5, further comprising:
a wire inserted in the sheath,
wherein the incision device includes a connector and a knife, the connector connecting the knife and the wire, and
wherein, in the second mode, a portion of the connector closes a proximal opening of the first channel.

8. The endoscope treatment tool according to claim 6, further comprising:
a wire inserted in the sheath,
wherein the incision device includes a connector and a knife, the connector connecting the knife and the wire, and
wherein, in the second mode, a portion of the connector closes a proximal opening of the first channel.

9. The endoscope treatment tool according to claim 8, wherein the first opening is formed in an outer surface of the connector.

10. An endoscope treatment tool, comprising:
a sheath including a distal end portion having a first channel, wherein the sheath includes a main flow chamber extending proximally more than the distal end portion; and
an incision device inserted in the first channel, wherein the incision device is translatable in the first channel,
wherein the incision device includes a second channel extending along a longitudinal axis of the incision device,
wherein the endoscope treatment tool is switchable between a first mode and a second mode,
wherein the endoscope treatment tool is in the first mode when the incision device is in a first position and the endoscope treatment tool is in the second mode when the incision device is in a second position, and
wherein:
in the first mode, a first path for fluid between the main flow chamber and the first channel is open and a second path for fluid between the main flow chamber and the second channel is closed, and
in the second mode, the second path for fluid between the main flow chamber and the second channel is open and the first path for fluid between the main flow chamber and the first channel is closed.

11. The endoscope treatment tool according to claim 10, wherein an opening of the second channel defines a first opening,
wherein the first opening opens in an outer peripheral surface of the incision device, and
wherein, in the first mode, a portion of the sheath closes the first opening.

12. The endoscope treatment tool according to claim 11, further comprising:

a wire inserted in the sheath, wherein the incision device includes a connector and a knife, the connector connecting the knife and the wire, and wherein, in the second mode, a portion of the connector closes a proximal opening of the first channel.

13. The endoscope treatment tool according to claim 12, wherein the first opening is formed in an outer surface of the connector.

\* \* \* \* \*